(12) United States Patent
Wähler et al.

(10) Patent No.: US 8,067,227 B2
(45) Date of Patent: Nov. 29, 2011

(54) VIRAL VECTORS AND THE USE OF THE SAME FOR GENE THERAPY

(75) Inventors: Reinhard Wähler, Hamburg (DE); Frank Schnieders, Hamburg (DE)

(73) Assignee: Universitätsklinikum Hamburg-Eppendorf, Hamburg (DE)

( * ) Notice: Subject to any disclaimer, the term of this patent is extended or adjusted under 35 U.S.C. 154(b) by 1559 days.

(21) Appl. No.: 10/530,706

(22) PCT Filed: Oct. 10, 2003

(86) PCT No.: PCT/EP03/11252
§ 371 (c)(1),
(2), (4) Date: Nov. 22, 2005

(87) PCT Pub. No.: WO2004/035799
PCT Pub. Date: Apr. 29, 2004

(65) Prior Publication Data
US 2006/0153805 A1 Jul. 13, 2006

(30) Foreign Application Priority Data
Oct. 11, 2002 (DE) .................. 102 48 141

(51) Int. Cl.
C12N 15/00 (2006.01)
A61K 48/00 (2006.01)
C07H 21/02 (2006.01)
(52) U.S. Cl. .................... 435/320.1; 514/44 R; 536/23.1
(58) Field of Classification Search ............... 435/320.1; 514/44
See application file for complete search history.

(56) References Cited

U.S. PATENT DOCUMENTS
5,756,085 A * 5/1998 Sykes et al. .................. 424/85.2
2002/0018767 A1 2/2002 Kim et al.

FOREIGN PATENT DOCUMENTS
WO WO 00/41508 7/2000
WO WO 02/27007 A2 4/2002

OTHER PUBLICATIONS

Wen et al., 2001, Cancer Gene Therapy, vol. 8, pp. 361-370.*
Wilson JM, 1996, Molecular Med., vol. 334(18), pp. 1185-1187.*
Martinet et al., 2000, J. NCI, vol. 92(11), pp. 931-936.*
Vinay et al.,1998, Seminars in Immunology, vol. 10, pp. 481-489.*
Yokota et al., 1985, PNAS, vol. 82, pp. 68-72.*
Martinez-Salas et al., Current Opinion in Biotechnology 1999, vol. 10, pp. 458-464.*
Hennecke et al., 2001, Nucleic Acid Res., vol. 29(16), pp. 3327-3334.*
Addison et al., "Intratumoral coinjection of adenoviral vectors expressing IL-2 and IL-12 results in enhanced frequency of regression of injected and untreated distal tumors", Gene Therapy, vol. 5, pp. 1400-1409 (1998).
Barajas et al., "Gene Therapy of Orthotopic Hepatocellular Carcinoma in Rats Using Adenovirus Coding for Interleukin 12", Hepatology, vol. 33, No. 1, pp. 52-61 (2001).

Brunda et al., "Antitumor and Antimetastatic Activity of Interleukin 12 against Murine Tumors", J. Exp. Med., vol. 178, pp. 1223-1230 (1993).
Carroll et al., "Construction and Characterization of a Triple-Recombinant Vaccinia Virus Encoding B7-1, Interleukin 12, and a Model Tumor Antigen", Journal of the National Cancer Institute, vol. 90, No. 24, pp. 1881-1887 (1998).
Cohen, "IL-12 Deaths: Explanation and a Puzzle", Science, vol. 270, pp. 908 (1995).
Emtage et al., "A Double Recombinant Adenovirus Expressing the Costimulatory Molecule B7-1 (Murine) and Human IL-2 Induces Complete Tumor Regression in a Murine Breast Adenocarcinoma Model", The Journal of Immunology, vol. 160, pp. 2531-2538 (1998).
Gillis et al., "T Cell Growth Factor: Parameters of Production and a Quantitative Microassay for Activity", The Journal of Immunology, vol. 120, No. 6, pp. 2027-2032 (1978).
Guinn et al., "4-1BBL Cooperates with B7-1 and B7-2 in Converting a B Cell Lymphoma Cell Line into a Long-Lasting Antitumor Vaccine", The Journal of Immunology, vol. 162, pp. 5003-5010 (1999).
Gyorffy et al., "Combined Treatment of a Murine Breast Cancer Model with Type 5 Adenovirus Vectors Expressing Murine Angiostatin and IL-12: A Role for Combined Anti-Angiogenesis and Immunotherapy", The Journal of Immunology, vol. 166, pp. 6212-6217 (2001).
Hock et al., "Mechanisms of rejection induced by tumor cell-targeted gene transfer of interleukin 2, interleukin 4, interleukin 7, tumor necrosis factor, or interferon γ", Proc. Natl. Acad. Sci. USA, vol. 90, pp. 2774-2778 (1993).
International Search Report of PCT/EP03/11252, dated Apr. 16, 2004.
Kwon et al., "4-1BB: Still in the Midst of Darkness", Mol. Cells, vol. 10, No. 2, pp. 119-126 (2000).
Lieschke et al., "Bioactive murine and human interleukin-12 fusion proteins which retain antitumor activity in vivo", Nature Biotechnology, vol. 15, pp. 35-40 (1997). Llovet et al., "Natural History of Untreated Nonsurgical Hepatocellular Carcinoma: Rationale for the Design and Evaluation of Therapeutic Trials", Hepatology, vol. 29, pp. 62-67 (1999).
Lotze et al., "Cytokine Gene Therapy of Cancer Using Interleukin-12: Murine and Clinical Trials", Annals New York Academy of Sciences, vol. 795, pp. 440-454 (1997).
Mah et al., "Virus-Based Gene Delivery Systems", Clin. Pharmacokinet, vol. 41, No. 12, pp. 901-911 (2002).
Martinet et al., "Immunomodulatory Gene Therapy with Interleukin 12 and 4-1BB Ligand: Long-Term Remission of Liver Metastases in a Mouse Model", Journal of the National Cancer Institute, vol. 92, No. 11, pp. 931-936 (2000).
Martinet et al., "T cell activation with systematic agonistic antibody versus local 4-1BB ligand gene delivery combined with interleukin-12 eradicate liver metastases of breast cancer", Gene Therapy, vol. 9, pp. 786-792 (2002).
Mazzolini et al., "Regression of cancer and induction of antitumor immunity by intratumoral injection of colon adenovirus expressing interleukin-12", Cancer Gene Therapy, vol. 6, No. 6, pp. 514-522 (1999).

(Continued)

Primary Examiner — Valarie Bertoglio
Assistant Examiner — David A Montanari
(74) Attorney, Agent, or Firm — Arnold & Porter LLP

(57) ABSTRACT

The invention relates to viral vectors comprising nucleic acid sequences coding for single chain interleukin-12 (single chain IL-12 or scIL12) and a costimulator protein, and to the use of vectors for gene therapy, especially for the treatment of tumors. The invention further relates to adenoviral vectors containing nucleic acid sequences having a sequence homology of at least 90% in relation to the sequence displayed in FIGS. 19 and 20 (IL-12), in FIG. 21 (4-1BB ligand) and in FIG. 22 (IL-2) and optionally also one of the sequences displayed in FIG. 23A (B7-1) or 23B (B7-2).

18 Claims, 57 Drawing Sheets

OTHER PUBLICATIONS

Melero et al., "IL-12 gene therapy for cancer: in synergy with other immunotherapies", *Trends in Immunology*, vol. 22, No. 3, pp. 113-115 (2001).

Nicklin and Baker, "Tropism-Modified Adenoviral and Adeno-Associated Viral Vectors for Gene Therapy", *Current Gene Therapy*, vol. 2, pp. 273-293 (2002).

Putzer et al., "Interleukin 12 and B7-1 costimulatory molecule expressed by an adenovirus vector act synergistically to facilitate tumor regression", *Proc. Natl. Acad. Sci. USA*, vol. 94, pp. 10889-10894 (1997).

Ruiz et al., "Gene Therapy of Hepatocellular Carcinoma", *Digestive Diseases*, vol. 19, pp. 324-332 (2001).

Sethi et al., "Postexposure prophylaxis against prion disease with a stimulator of innate immunity", *The Lancet*, vol. 360, pp. 229-230 (2002).

van der Meide et al., "Stimulation of both humoral and cellular immune responses to HIV-1 gp120 by interleukin-12 in *Rhesus macaques*", *Vaccine*, vol. 20, pp. 2296-2302 (2002).

van der Poel el al., "Epidermal Growth Factor Receptor Targeting of Replication Competent Adenovirus Enhances Cytotoxicity in Bladder Cancer", *The Journal of Urology*, vol. 168, pp. 266-272 (2002).

Vinay and Kwon, "Role of 4-1BB in immune responses", *Immunology*, vol. 10, pp. 481-489 (1998).

Yoon et al., "Selectively Replicating Adenoviruses for Oncolytic Therapy", *Current Cancer Drug Targets*, vol. 1, No. 2, pp. 85-107 (2001).

Anderson et al., "Construction and Biological Characterization of an Interleukin-12 Fusion Protein (Flexi-12): Delivery to Acute Myeloid Leukemic Blasts Using Adeno-Associated Virus", *Human Gene Therapy*, 8:1125-1135 (1997).

Gillies et al., "Bi-Functional Cytokine Fusion Proteins for Gene Therapy and Antibody-Targeted Treatment of Cancer", *Cancer Immunol Immunother.*, 8:449-460 (2002) (Abstract).

Tan et al., "4-1BB Ligand, a Member of the TNF Family, is Important for the Generation of Antiviral CD8 T Cell Responses", *The Journal of Immunology*, pp. 4859-4868 (1999).

\* cited by examiner

```
TAGTAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCAATA
ATGACGTATGTTCCCATAGTAACGCCAATAGGGACTTTCCATTGACGTCAATGGGTGGAG
TATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTA
TGGGACTTTCCTACTTGGCAGTACATCTACGTATTAGTCATCGCTATTACCATGGTGATG
CGGTTTTGGCAGTACATCAATGGGCGTGGATAGCGGTTTGACTCACGGGGATTTCCAAGT
CTCCACCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGGTGGGAG
GTCTATATAAGCAGAGCTGGTTTAGTGAACCGTCAGATCCGCTAGAGATCTGGATCCGAA
TTCGCCGCCACCATGGGTCCTCAGAAGCTAACCATCTCCTGGTTTGCCATCGTTTTGCTG
GTGTCTCCACTCATGGCCATGTGGGAGCTGGAGAAAGACGTTTATGTTGTAGAGGTGGAC
TGGACTCCCGATGCCCCTGGAGAAACAGTGAACCTCACCTGTGACACGCCTGAAGAAGAT
GACATCACCTGGACCTCAGACCAGAGACATGGAGTCATAGGCTCTGGAAAGACCCTGACC
ATCACTGTCAAAGAGTTTCTAGATGCTGGCCAGTACACCTGCCACAAAGGAGGCGAGACT
CTGAGCCACTCACATCTGCTGCTCCACAAGAAGGAAAATGGAATTTGGTCCACTGAAATT
TTAAAAAATTTCAAAAACAAGACTTTCCTGAAGTGTGAAGCACCAAATTACTCCGGACGG
TTCACGTGCTCATGGCTGGTGCAAAGAAACATGGACTTGAAGTTCAACATCAAGAGCAGT
AGCAGTTCCCCTGACTCTCGGGCAGTGACATGTGGAATGGCGTCTCTGTCTGCAGAGAAG
GTCACACTGGACCAAAGGGACTATGAGAAGTATTCAGTGTCCTGCCAGGAGGATGTCACC
TGCCCAACTGCCGAGGAGACCCTGCCCATTGAACTGGCGTTGGAAGCACGGCAGCAGAAT
AAATATGAGAACTACAGCACCAGCTTCTTCATCAGGGACATCATCAAACCAGACCCGCCC
AAGAACTTGCAGATGAAGCCTTTGAAGAACTCACAGGTGGAGGTCAGCTGGGAGTACCCT
GACTCCTGGAGCACTCCCCATTCCTACTTCTCCCTCAAGTTCTTTGTTCGAATCCAGCGC
AAGAAAGAAAAGATGAAGGAGACAGAGGAGGGGTGTAACCAGAAAGGTGCGTTCCTCGTA
GAGAAGACATCTACCGAAGTCCAATGCAAAGGCGGGAATGTCTGCGTGCAAGCTCAGGAT
CGCTATTACAATTCCTCATGCAGCAAGTGGGCATGTGTTCCCTGCAGGGTCCGATCCGGT
GGCGGTGGCTCGGGCGGTGGTGGGTCGGGTGGCGGCGGATCTAGGGTCATTCCAGTCTCT
GGACCTGCCAGGTGTCTTAGCCAGTCCCGAAACCTGCTGAAGACCACAGATGACATGGTG
AAGACGGCCAGAGAAAAGCTGAAACATTATTCCTGCACTGCTGAAGACATCGATCATGAA
GACATCACACGGGACCAAACCAGCACATTGAAGACCTGTTTACCACTGGAACTACACAAG
AACGAGAGTTGCCTGGCTACTAGAGAGACTTCTTCCACAACAAGAGGGAGCTGCCTGCCC
CCACAGAAGACGTCTTTGATGATGACCCTGTGCCTTGGTAGCATCTATGAGGACTTGAAG
ATGTACCAGACAGAGTTCCA
GGCCATCAACGCAGCACTTCAGAATCACAACCATCAGCAGATCATTCTAGACAAGGGCAT
GCTGGTGGCCATCGATGAGCTGATGCAGTCTCTGAATCATAATGGCGAGACTCTGCGCCA
GAAACCTCCTGTGGGAGAAGCAGACCCTTACAGAGTGAAAATGAAGCTCTGCATCCTGCT
```

Figure 18 (part 1 of 3)

```
TCACGCCTTCAGCACCCGCGTCGTGACCATCAACAGGGTGATGGGCTATCTGAGCTCCGC
CTGAGAATTGATCCGGATTAGTCCAATTTGTTAAAGACAGGATGAAGCTTAAAACAGCTC
TGGGGTTGTACCCACCCCAGAGGCCCACGTGGCGGCTAGTACTCCGGTATTGCGGTACCC
TTGTACGCCTGTTTTATACTCCCTTCCCGTAACTTAGACGCACAAAACCAAGTTCAATAG
AAGGGGGTACAAACCAGTACCACCACGAACAAGCACTTCTGTTTCCCCGGTGATGTCGTA
TAGACTGCTTGCGTGGTTGAAAGCGACGGATCCGTTATCCGCTTATGTACTTCGAGAAGC
CCAGTACCACCTCGGAATCTTCGATGCGTTGCGCTCAGCACTCAACCCCAGAGTGTAGCT
TAGGCTGATGAGTCTGGACATCCCTCACCGGTGACGGTGGTCCAGGCTGCGTTGGCGGCC
TACCTATGGCTAACGCCATGGGACGCTAGTTGTGAACAAGGTGTGAAGAGCCTATTGAGC
TACATAAGAATCCTCCGGCCCCTGAATGCGGCTAATCCCAACCTCGGAGCAGGTGGTCAC
AAACCAGTGATTGGCCTGTCGTAACGCGCAAGTCCGTGGCGGAACCGACTACTTTGGGTG
TCCGTGTTTCCTTTTATTTTATTGTGGCTGCTTATGGTGACAATCACAGATTGTTATCAT
AAAGCGAATTGGATTGCGGCCGCGCCACCATGGACCAGCACACACTTGATGTGGAGGATA
CCGCGGATGCCAGACATCCAGCAGGTACTTCGTGCCCCTCGGATGCGGCGCTCCTCAGAG
ATACCGGGCTCCTCGCGGACGCTGCGCTCCTCTCAGATACTGTGCGCCCCACAAATGCCG
CGCTCCCCACGGATGCTGCCTACCCTGCGGTTAATGTTCGGGATCGCGAGGCCGCGTGGC
CGCCTGCACTGAACTTCTGTTCCCGCCACCCAAAGCTCTATGGCCTAGTCGCTTTGGTTT
TGCTGCTTCTGATCGCCGCCTGTGTTCCTATCTTCACCCGCACCGAGCCTCGGCCAGCGC
TCACAATCACCACCTCGCCCAACCTGGGTACCCGAGAGAATAATGCAGACCAGGTCACCC
CTGTTTCCCACATTGGCTGCCCCAACACTACACAACAGGGCTCTCCTGTGTTCGCCAAGC
TACTGGCTAAAAACCAAGCATCGTTGTGCAATACAACTCTGAACTGGCACAGCCAAGATG
GAGCTGGGAGCTCATACCTATCTCAAGGTCTGAGGTACGAAGAAGACAAAAAGGAGTTGG
TGGTAGACAGTCCCGGGCTCTACTACGTATTTTTGGAACTGAAGCTCAGTCCAACATTCA
CAAACACAGGCCACAAGGTGCAGGGCTGGGTCTCTCTTGTTTTGCAAGCAAAGCCTCAGG
TAGATGACTTTGACAACTTGGCCCTGACAGTGGAACTGTTCCCTTGCTCCATGGAGAACA
AGTTAGTGGACCGTTCCTGGAGTCAACTGTTGCTCCTGAAGGCTGGCCACCGCCTCAGTG
TGGGTCTGAGGGCTTATCTGCATGGAGCCCAGGATGCATACAGAGACTGGGAGCTGTCTT
ATCCCAACACCACCAGCTTTGGACTCTTTCTTGTGAAACCCGACAACCCATGGGAATGAG
AACTATCCTTCTTGTGACTGGCGCGCCTGATCAATCGATGTTTAAACGTTATTTTCCACC
ATATTGCCGTCTTTTGGCAATGTGAGGGCCCGGAAACCTGGCCCTGTCTTCTTGACGAGC
ATTCCTAGGGGTCTTTCCCCTCTCGCCAAAGGAATGCAAGGTCTGTTGAATGTCGTGAAG
GAAGCAGTTCCTCTGGAAGCTTCTTGAAGACAAACAACGTCTGTAGCGACCCTTTGCAGG
CAGCGGAACCCCCCACCTGGCGACAGGTGCCTCTGCGGCCAAAAGCCACGTGTATAAGAT
ACACCTGCAAAGGCGGCACAACCCCAGTGCCACGTTGTGAGTTGGATAGTTGTGAAAGA
GTCAAATGGCTCTCCTCAAGCGTATTCAACAAGGGGCTGAAGGATGCCCAGAAGGTACCC
CATTGTATGGGATCTGATCTGGGGCCTCGGTGCACATGCTTTACGTGTGTTTAGTCGAGG
TTAAAAAAACGTCTAGGCCCCCGAACCACGGGGACGTGGTTTTCCTTTGAAAAACACGA
TTCTCGAGACTAGTGCCACCATGTACAGCATGCAGCTCGCATCCTGTGTCACATTGACAC
TTGTGCTCCTTGTCAACAGCGCACCCACTTCAAGCTCCACTTCAAGCTCTACAGCGGAAG
CACAGCAGCAGCAGCAGCAGCAGCAGCAGCAGCAGCAGCACCTGGAGCAGCTGTTGATGG
ACCTACAGGAGCTCCTGAGCAGGATGGAGAATTACAGGAACCTGAAACTCCCCAGGATGC
TCACCTTCAAATTTTACTTGCCCAAGCAGGCCACAGAATTGAAAGATCTTCAGTGCCTAG
```

Figure 18 (part 2 of 3)

```
AAGATGAACTTGGACCTCTGCGGCATGTTCTGGATTTGACTCAAAGCAAAAGCTTTCAAT
TGGAAGATGCTGAGAATTTCATCAGCAATATCAGAGTAACTGTTGTAAAACTAAAGGGCT
CTGACAACACATTTGAGTGCCAATTCGATGATGAGTCAGCAACTGTGGTGGACTTTCTGA
GGAGATGGATAGCCTTCTGTCAAAGCATCATCTCAACAAGCCCTCAATAACTATGTAACG
CGTGCTAGCATGGCCGGCCGCGGCCGCGGCCGCTCGAGCCTAAGCTTCTAGATAAGATAT
CCGATCCACCGGATCTAGATAACTGATCATAATCAGCCATACCACATTTGTAGAGGTTTT
ACTTGCTTTAAAAAACCTCCCACACCTCCCCCTGAACCTGAAACATAAAATGAATGCAAT
TGTTGTTGTTAACTTGTTTATTGCAGCTTATAATGGTTACAAATAAAGCAATAGCATCAC
AAATTTCACAAATAAAGCATTTTTTTCACTGCATTCTAGTTGTGGTTTGTCCAAACTCAT
CAATGTATCTTA
```

Figure 18 (part 3 of 3)

```
ATGTGTCACCAGCAGTTGGTCATCTCTTGGTTTTCCCTGGTTTTTCTGGCATCTCCCCTCGTGGCCATATGGGAA
CTGAAGAAAGATGTTTATGTCGTAGAATTGGATTGGTATCCGGATGCCCCTGGAGAAATGGTGGTCCTCACCTGT
GACACCCCTGAAGAAGATGGTATCACCTGGACCTTGGACCAGAGCAGTGAGGTCTTAGGCTCTGGCAAAACCCTG
ACCATCCAAGTCAAAGAGTTTGGAGATGCTGGCCAGTACACCTGTCACAAAGGAGGCGAGGTTCTAAGCCATTCG
CTCCTGCTGCTTCACAAAAAGGAAGATGGAATTTGGTCCACTGATATTTTAAAGGACCAGAAAGAACCCAAAAAT
AAGACCTTTCTAAGATGCGAGGCCAAGAATTATTCTGGACGTTTCACCTGCTGGTGGCTGACGACAATCAGTACT
GATTTGACATTCAGTGTCAAAAGCAGCAGAGGCTCTTCTGACCCCCAAGGGGTGACGTGCGGAGCTGCTACACTC
TCTGCAGAGAGAGTCAGAGGGGACAACAAGGAGTATGAGTACTCAGTGGAGTGCCAGGAGGACAGTGCCTGCCCA
GCTGCTGAGGAGAGTCTGCCCATTGAGGTCATGGTGGATGCCGTTCACAAGCTCAAGTATGAAAACTACACCAGC
AGCTTCTTCATCAGGGACATCATCAAACCTGACCCACCCAAGAACTTGCAGCTGAAGCCATTAAAGAATTCTCGG
CAGGTGGAGGTCAGCTGGGAGTACCCTGACACCTGGAGTACTCCACATTCCTACTTCTCCCTGACATTCTGCGTT
CAGGTCCAGGGCAAGAGCAAGAGAGAAAAGAAAGATAGAGTCTTCACGGACAAGACCTCAGCCACGGTCATCTGC
CGCAAAAAATGCCAGCATTAGCGTGCGGGCCCAGGACCGCTACTATAGCTCATCTTGGAGCGAATGGGCATCTGTG
CCCTGCAGTTAG
```

Figure 19

```
atgtggcccctgggtcagcctcccagccaccgccctcacctgccgcggccacaggtctgcatccagcggctcgc
cctgtgtccctgcagtgccggctcagcatgtgtccagcgcgcagcctcctccttgtggctaccctggtcctcctg
gaccacctcagtttggccagaaacctccccgtggccactccagacccaggaatgttcccatgccttcaccactcc
caaaacctgctgagggccgtcagcaacatgctccagaaggccagacaaactctagaatttttacccttgcacttct
gaagagattgatcatgaagatatcacaaaagataaaaccagcacagtggaggcctgtttaccattggaattaacc
aagaatgagagttgcctaaattccagagagacctctttcataactaatgggagttgcctggcctccagaaagacc
tcttttatgatggccctgtgccttagtagtatttatgaagacttgaagatgtaccaggtggagttcaagaccatg
aatgcaaagcttctgatggatcctaagaggcagatctttctagatcaaaacatgctggcagttattgatgagctg
atgcaggccctgaatttcaacagtgagactgtgccacaaaaatcctcccttgaagaaccggatttttataaaact
aaaatcaagctctgcatacttcttcatgctttcagaattcgggcagtgactattgatagagtgatgagctatctg
aatgcttcctaa
```

Figure 20

```
gtcatggaatacgcctctgacgcttcactggaccccgaagcccgtggcctcccgcgcccgcgctcgcgcctgc
cgcgtactgccttgggccctggtcgcggggctgctgctgctgctgctcgctgccgcctgcgccgtcttcctc
gcctgccctgggccgtgtccggggctcgcgcctcgcccggctccgcggccagcccgagactccgcgagggtccc
gagctttcgcccgacgatcccgccggcctcttggacctgcggcagggcatgtttgcgcagctggtggcccaaaat
gttctgctgatcgatgggcccctgagctggtacagtgacccaggcctggcaggcgtgtccctgacgggggcctg
agctacaaagaggacacgaaggagctggtggtggccaaggctggagtctactatgtcttctttcaactagagctg
cggcgcgtggtggccggcgagggctcaggctccgtttcacttgcgctgcacctgcagccactgcgctctgctgct
ggggccgccgccctggctttgaccgtggacctgccacccgcctcctccgaggctcggaactcggccttcggtttc
cagggccgcttgctgcacctgagtgcggccagcgcctgggcgtccatcttcacactgaggccagggcacgccat
gcctggcagcttacccagggcgccacagtcttgggactcttccgggtgaccccgaaatcccagccggactccct
tcaccgaggtcggaataa
```

Figure 21

```
atgtacaggatgcaactcctgtcttgcattgcactaattcttgcacttgtcacaaacagtgcacctacttcaagt
tcgacaaagaaaacaaagaaaacacagctacaactggagcattcactgctggatttacagatgattttgaatgga
attaataattacaagaatcccaaactcaccaggatgctcacatttaagttttacatgcccaagaaggccacagaa
ctgaaacagcttcagtgtctagaagaagaactcaaacctctggaggaagtgctgaatttagctcaaagcaaaaac
tttcacttaagacccagggacttaatcagcaatatcaacgtaatagttctggaactaaagggatctgaaacaaca
ttcatgtgtgaatatgcagatgagacagcaaccattgtagaatttctgaacagatggattaccttttgtcaaagc
atcatctcaacactaacttgata
```

Figure 22

Figure 23A atggg ccacacacgg aggcagggaa catcaccatc caagtgtcca tacctcaatt tctttcagct cttggtgctg gctggtcttt ctcacttctg ttcaggtgtt atccacgtga ccaaggaagt gaaagaagtg gcaacgctgt cctgtggtca caatgtttct gttgaagagc tggcacaaac tcgcatctac tggcaaaagg agaagaaaat ggtgctgact atgatgtctg gggacatgaa tatatggccc agtacaaga accggaccat ctttgatatc actaataacc tctccattgt gatcctggct ctgcgcccat ctgacgaggg cacatacgag tgtgttgttc tgaagtatga aaaagacgct ttcaagcggg aacacctggc tgaagtgacg ttatcagtca aagctgactt ccctacacct agtatatctg actttgaaat tccaacttct aatattagaa ggataaattg ctcaacctct ggaggttttc cagagcctca cctctcctgg ttggaaaatg gagaagaatt aaatgccatc aacacaacag tttcccaaga tcctgaaact gagctctatg ctgttagcag aaactggat ttcaatatga caaccaacca cagcttcatg tgtctcatca agtatggaca tttaagagtg aatcagacct tcaactggaa tacaaccaag caagagcatt ttcctgataa cctgctccca tcctgggcca ttaccttaat ctcagtaaat ggaatttttg tgatatgctg cctgacctac tgctttgccc caagatgcag agagagaagg aggaatgaga gattgagaag ggaaagtgta cgccctgtat aa

Figure 23B atg ggactgagta acattctctt tgtgatggcc ttcctgctct ctggtgctgc tcctctgaag attcaagctt atttcaatga gactgcagac ctgccatgcc aatttgcaaa ctctcaaaac caaagcctga gtgagctagt agtattttgg caggaccagg aaaacttggt tctgaatgag gtatacttag gcaaagagaa atttgacagt gttcattcca agtatatggg ccgcacaagt tttgattcgg acagttggac cctgagactt cacaatcttc agatcaagga caagggcttg tatcaatgta tcatccatca caaaaagccc acaggaatga ttcgcatcca ccagatgaat tctgaactgt cagtgcttgc taacttcagt caacctgaaa tagtaccaat ttctaatata acagaaaatg tgtacataaa tttgacctgc tcatctatac acggttaccc agaacctaag aagatgagtg ttttgctaag aaccaagaat tcaactatcg agtatgatgg tattatgcag aaatctcaag ataatgtcac agaactgtac gacgtttcca tcagcttgtc tgtttcattc cctgatgtta cgagcaatat gaccatcttc tgtattctgg aaactgacaa gacgcggctt ttatcttcac ctttctctat agagcttgag gaccctcagc ctccccccaga ccacattcct tggattacag ctgtacttcc aacagttatt atatgtgtga tggtttctg tctaattcta tggaaatgga agaagaagaa gcggcctcgc aactcttata aatgtggaac caacacaatg gagagggaag agagtgaaca gaccaagaaa agagaaaaaa tccatatacc tgaaagatct gatgaagccc agcgtgtttt taaaagttcg aagacatctt catgcgacaa aagtgataca tgttttaa

```
AATGCGCCGNNNNNNNNNNNNNNNNNNNNNNNNNNNTTAATTAANNNTCCCTTCCAGCTCTCT
GCCCCTTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGG
CGGAACACATGTAAGCGACGGATGTGGCAAAAGTGACGTTTTTGGTGTGCGCCGGTGTAC
ACAGGAAGTGACAATTTTCGCGCGGTTTTAGGCGGATGTTGTAGTAAATTTGGGCGTAAC
CGAGTAAGATTTGGCCATTTTCGCGGGAAAACTGAATAAGAGGAAGTGAAATCTGAATAA
TTTTGTGTTACTCATAGCGCGTAANNNNNTAATAGTAATCAATTACGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATGGCC
CGCCTGGCATTATGCCCAGTACATGACCTTATGGGACTTTCCTACTTGGCAGTACATCTA
CGTATTAGTCATCGCTATTACCATGGTGATGCGGTTTTGGCAGTACATCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCCATTGAC
GCAAATGGGCGGTAGGCGTGTACGGTGGGAGGTCTATATAAGCAGAGCTGGTTTAGTGAA
CCGTCAGATCCGCTAGAGATCTGGATCCGAATTCGCCGCCACCATGGGTCCTCAGAAGCT
AACCATCTCCTGGTTTGCCATCGTTTTGCTGGTGTCTCCACTCATGGCCATGTGGGAGCT
GGAGAAAGACGTTTATGTTGTAGAGGTGGACTGGACTCCCGATGCCCCTGGAGAAACAGT
GAACCTCACCTGTGACACGCCTGAAGAAGATGACATCACCTGGACCTCAGACCAGAGACA
TGGAGTCATAGGCTCTGGAAAGACCCTGACCATCACTGTCAAAGAGTTTCTAGATGCTGG
CCAGTACACCTGCCACAAAGGAGGCGAGACTCTGAGCCACTCACATCTGCTGCTCCACAA
GAAGGAAAATGGAATTTGGTCCACTGAAATTTTAAAAAATTTCAAAAACAAGACTTTCCT
GAAGTGTGAAGCACCAAATTACTCCGGACGGTTCACGTGCTCATGGCTGGTGCAAAGAAA
CATGGACTTGAAGTTCAACATCAAGAGCAGTAGCAGTTCCCCTGACTCTCGGGCAGTGAC
ATGTGGAATGGCGTCTCTGTCTGCAGAGAAGGTCACACTGGACCAAAGGGACTATGAGAA
GTATTCAGTGTCCTGCCAGGAGGATGTCACCTGCCCAACTGCCGAGGAGACCCTGCCCAT
TGAACTGGCGTTGGAAGCACGGCAGCAGAATAAATATGAGAACTACAGCACCAGCTTCTT
CATCAGGGACATCATCAAACCAGACCCGCCCAAGAACTTGCAGATGAAGCCTTTGAAGAA
CTCACAGGTGGAGGTCAGCTGGGAGTACCCTGACTCCTGGAGCACTCCCCATTCCTACTT
CTCCCTCAAGTTCTTTGTTCGAATCCAGCGCAAGAAAGAAAAGATGAAGGAGACAGAGGA
GGGGTGTAACCAGAAAGGTGCGTTCCTCGTAGAGAAGACATCTACCGAAGTCCAATGCAA
AGGCGGGAATGTCTGCGTGCAAGCTCAGGATCGCTATTACAATTCCTCATGCAGCAAGTG
GGCATGTGTTCCCTGCAGGGTCCGATCCGGTGGCGGTGGCTCGGCGGTGGTGGGTCGGG
TGGCGGCGGATCTAGGGTCATTCCAGTCTCTGGACCTGCCAGGTGTCTTAGCCAGTCCCG
AAACCTGCTGAAGACCACAGATGACATGGTGAAGACGGCCAGAGAAAAGCTGAAACATTA
TTCCTGCACTGCTGAAGACATCGATCATGAAGACATCACACGGGACCAAACCAGCACATT
GAAGACCTGTTTACCACTGGAACTACACAAGAACGAGAGTTGCCTGGCTACTAGAGAGAC
TTCTTCCACAACAAGAGGGAGCTGCCTGCCCCCACAGAAGACGTCTTTGATGATGACCCT
GTGCCTTGGTAGCATCTATGAGGACTTGAAGATGTACCAGACAGAGTTCCAGGCCATCAA
```

Figure 24 (part 1 of 5)

```
CGCAGCACTTCAGAATCACAACCATCAGCAGATCATTCTAGACAAGGGCATGCTGGTGGC
CATCGATGAGCTGATGCAGTCTCTGAATCATAATGGCGAGACTCTGCGCCAGAAACCTCC
TGTGGGAGAAGCAGACCCTTACAGAGTGAAAATGAAGCTCTGCATCCTGCTTCACGCCTT
CAGCACCCGCGTCGTGACCATCAACAGGGTGATGGGCTATCTGAGCTCCGCCTGAGAATT
GATCCGGATTAGTCCAATTTGTTAAAGACAGGATGAAGCTTAAAACAGCTCTGGGGTTGT
ACCCACCCCAGAGGCCCACGTGGCGGCTAGTACTCCGGTATTCGGTACCCTTGTACGCC
TGTTTTATACTCCCTTCCCGTAACTTAGACGCACAAAACCAAGTTCAATAGAAGGGGGTA
CAAACCAGTACCACCACGAACAAGCACTTCTGTTTCCCCGGTGATGTCGTATAGACTGCT
TGCGTGGTTGAAAGCGACGGATCCGTTATCCGCTTATGTACTTCGAGAAGCCCAGTACCA
CCTCGGAATCTTCGATGCGTTGCGCTCAGCACTCAACCCAGAGTGTAGCTTAGGCTGAT
GAGTCTGGACATCCCTCACCGGTGACGGTGGTCCAGGCTGCGTTGGCGGCCTACCTATGG
CTAACGCCATGGGACGCTAGTTGTGAACAAGGTGTGAAGAGCCTATTGAGCTACATAAGA
ATCCTCCGGCCCCTGAATGCGGCTAATCCCAACCTCGGAGCAGGTGGTCACAAACCAGTG
ATTGGCCTGTCGTAACGCGCAAGTCCGTGGCGGAACCGACTACTTTGGGTGTCCGTGTTT
CCTTTTATTTTATTGTGGCTGCTTATGGTGACAATCACAGATTGTTATCATAAAGCGAAT
TGGATTGCGGCCGCGCCACCATGGACCAGCACACACTTGATGTGGAGGATACCGCGGATG
CCAGACATCCAGCAGGTACTTCGTGCCCCTCGGATGCGGCGCTCCTCAGAGATACCGGGC
TCCTCGCGGACGCTGCGCTCCTCTCAGATACTGTGCGCCCACAAATGCCGCGCTCCCCA
CGGATGCTGCCTACCCTGCGGTTAATGTTCGGGATCGCGAGGCCGCGTGGCCGCCTGCAC
TGAACTTCTGTTCCCGCCACCCAAAGCTCTATGGCCTAGTCGCTTTGGTTTTGCTGCTTC
TGATCGCCGCCTGTGTTCCTATCTTCACCCGCACCGAGCCTCGGCCAGCGCTCACAATCA
CCACCTCGCCAACCTGGGTACCCGAGAGAATAATGCAGACCAGGTCACCCCTGTTTCCC
ACATTGGCTGCCCCAACACTACACAACAGGGCTCTCCTGTGTTCGCCAAGCTACTGGCTA
AAAACCAAGCATCGTTGTGCAATACAACTCTGAACTGGCACAGCCAAGATGGAGCTGGGA
GCTCATACCTATCTCAAGGTCTGAGGTACGAAGAAGACAAAAAGGAGTTGGTGGTAGACA
GTCCCGGGCTCTACTACGTATTTTTGGAACTGAAGCTCAGTCCAACATTCACAAACACAG
GCCACAAGGTGCAGGGCTGGGTCTCTCTTGTTTTGCAAGCAAAGCCTCAGGTAGATGACT
TTGACAACTTGGCCCTGACAGTGGAACTGTTCCCTTGCTCCATGGAGAACAAGTTAGTGG
ACCGTTCCTGGAGTCAACTGTTGCTCCTGAAGGCTGGCCACCGCCTCAGTGTGGGTCTGA
GGGCTTATCTGCATGGAGCCCAGGATGCATACAGAGACTGGGAGCTGTCTTATCCCAACA
CCACCAGCTTTGGACTCTTTCTTGTGAAACCCGACAACCCATGGGAATGAGAACTATCCT
TCTTGTGACTGGCGCGCCTGATCAATCGATGTTTAAACGTTATTTTCCACCATATTGCCG
TCTTTTGGCAATGTGAGGGCCCGGAAACCTGGCCCTGTCTTCTTGACGAGCATTCCTAGG
GGTCTTTCCCCTCTCGCCAAAGGAATGCAAGGTCTGTTGAATGTCGTGAAGGAAGCAGTT
CCTCTGGAAGCTTCTTGAAGACAAACAACGTCTGTAGCGACCCTTTGCAGGCAGCGGAAC
CCCCCACCTGGCGACAGGTGCCTCTGCGGCCAAAAGCCACGTGTATAAGATACACCTGCA
AAGGCGGCACAACCCCAGTGCCACGTTGTGAGTTGGATAGTTGTGGAAAGAGTCAAATGG
CTCTCCTCAAGCGTATTCAACAAGGGGCTGAAGGATGCCCAGAAGGTACCCATTGTATG
GGATCTGATCTGGGGCCTCGGTGCACATGCTTACCTGTGTTTAGTCGAGGTTAAAAAAA
CGTCTAGGCCCCCCGAACCACGGGACGTGGTTTTCCTTTGAAAAACACGATTCTCGAGA
CTAGTGCCACCATGTACAGCATGCAGCTCGCATCCTGTGTCACATTGACACTTGTGCTCC
TTGTCAACAGCGCACCCACTTCAAGCTCCACTTCAAGCTCTACAGCGGAAGCACAGCAGC
```

Figure 24 (part 2 of 5)

```
AGCAGCAGCAGCAGCAGCAGCAGCAGCACCTGGAGCAGCTGTTGATGGACCTACAGG
AGCTCCTGAGCAGGATGGAGAATTACAGGAACCTGAAACTCCCCAGGATGCTCACCTTCA
AATTTTACTTGCCCAAGCAGGCCACAGAATTGAAAGATCTTCAGTGCCTAGAAGATGAAC
TTGGACCTCTGCGGCATGTTCTGGATTTGACTCAAAGCAAAAGCTTTCAATTGGAAGATG
CTGAGAATTTCATCAGCAATATCAGAGTAACTGTTGTAAAACTAAAGGGCTCTGACAACA
CATTTGAGTGCCAATTCGATGATGAGTCAGCAACTGTGGTGGACTTTCTGAGGAGATGGA
TAGCCTTCTGTCAAAGCATCATCTCAACAAGCCCTCAATAACTATGTAACGCGTGCTAGC
ATGGCCGGCCGCGGCCGCGGCCGCTCGAGCCTAAGCTTCTAGATAAGATATCCGATCCAC
CGGATCTAGATAACTGATCATAATCAGCCATACCACATTTGTAGAGGTTTTACTTGCTTT
AAAAAACCTCCCACACCTCCCCCTGAACCTGAAACATAAAATGAATGCAATTGTTGTTGT
TAACTTGTTTATTGCAGCTTATAATGGTTACAAATAAAGCAATAGCATCACAAATTTCAC
AAATAAAGCATTTTTTTCACTGCATTCTAGTTGTGGTTTGTCCAAACTCATCAATGTATC
TTAACGCNNNNTAAGGGTGGGAAAGAATATATAAGGTGGGGGTCTTATGTAGTTTTGTAT
CTGTTTTGCAGCAGCCGCCGCCGCCATGAGCACCAACTCGTTTGATGGAAGCATTGTGAG
CTCATATTTGACAACGCGCATGCCCCATGGGCCGGGGTGCGTCAGAATGTGATGGCTC
CAGCATTGATGGTCGCCCCGTCCTGCCCGCAAACTCTACTACCTTGACCTACGAGACCGT
GTCTGGAACGCCGTTGGAGACTGCAGCCTCCGCCGCCGCTTCAGCCGCTGCAGCCACCGC
CCGCGGGATTGTGACTGACTTTGCTTTCCTGAGCCCGCTTGCAAGCAGTGCAGCTTCCCG
TTCATCCGCCCGCGATGACAAGTTGACGGCTCTTTTGGCACAATTGGATTCTTTGACCCG
GGAACTTAATGTCGTTTCTCAGCAGCTGTTGGATCTGCGCCAGCAGGTTTCTGCCCTGAA
GGCTTCCTCCCCTCCCAATGCGGTTTAAAACATAAATAAAAACCAGACTCTGTTTGGAT
TTGGATCAAGCAAGTGTCTTGCTGTCTTTATTTAGGGGTTTTGCGCGCGCGGTAGGCCCG
GGACCAGCGGTCTCGGTCGTTGAGGGTCCTGTGTATTTTTTCCAGGACGTGGTAAAGGTG
ACTCTGGATGTTCAGATACATGGGCATAAGCCCGTCTCTGGGGTGGAGGTAGCACCACTG
CAGAGCTTCATGCTGCGGGTGGTGTTGTAGATGATCCAGTCGTAGCAGGAGCGCTGGGC
GTGGTGCCTAAAAATGTCTTTCAGTAGCAAGCTGATTGCCAGGGGCAGGCCCTTGGTGTA
AGTGTTTACAAAGCGGTTAGCTGGGATGGGTGCATACGTGGGCATATGAGATGCATCTT
GGACTGTATTTTTAGGTTGGCTATGTTCCCAGCCATATCCCTCCGGGGATTCATGTTGTG
CAGAACCACCAGCACAGTGTATCCGGTGCACTTGGGAAATTTGTCATGTAGCTTAGAAGG
AAATGCGTGGAAGAACTTGGAGACGCCCTTGTGACCTCCAAGATTTTCCATGCATTCGTC
CATAATGATGGCAATGGGCCCACGGGCGGCGGCCTGGGCGAAGATATTTCTGGGATCACT
AACGTCATAGTTGTGTTCCAGGATGAGATCGTCATAGGCCATTTTTACAAAGCGCGGGCG
GAGGGTGCCAGACTGCGGTATAATGGTTCCATCCGGCCCAGGGGCGTAGTTACCCTCACA
GATTTGCATTTCCCACGCTTTGAGTTCAGATGGGGGGATCATGTCTACCTGCGGGGCGAT
GAAGAAAACGGTTTCCGGGGTAGGGGAGATCAGCTGGGAAGAAAGCAGGTTCCTGAGCAG
CTGCGACTTACCGCAGCCGGTGGGCCCGTAAATCACACCTATTACCGGGTGCAACTGGTA
GTTAAGAGAGCTGCAGCTGCCGTCATCCCTGAGCAGGGGGGCCACTTCGTTAAGCATGTC
CCTGACTCGCATGTTTTCCCTGACCAAATCCGCCAGAAGGCGCTCGCCGCCCAGCGATAG
CAGTTCTTGCAAGGAAGCAAAGTTTTTCAACGGTTTGAGACCGTCCGCCGTAGGCATGCT
TTTGAGCGTTTGACCAAGCAGTTCCAGGCGGTCCCACAGCTCGGTCACCTGCTCTACGGC
ATCTCGATCCAGCATATCTCCTCGTTTCGCGGGTTGGGGCGGCTTTCGCTGTACGGCAGT
AGTCGGTGCTCGTCCAGACGGGCCAGGGTCATGTCTTTCCACGGGCGCAGGGTCCTCGTC
```

Figure 24 (part 3 of 5)

```
AGCGTAGTCTGGGTCACGGTGAAGGGGTGCGCTCCGGGCTGCGCGCTGGCCAGGGTGCGC
TTGAGGCTGGTCCTGCTGGTGCTGAAGCGCTGCCGGTCTTCGCCCTGCGCGTCGGCCAGG
TAGCATTTGACCATGGTGTCATAGTCCAGCCCCTCCGCGGCGTGGCCCTTGGCGCGCAGC
TTGCCCTTGGAGGAGGCGCCGCACGAGGGGCAGTGCAGACTTTTGAGGGCGTAGAGCTTG
GGCGCGAGAAATACCGATTCCGGGGAGTAGGCATCCGCGCCGCAGGCCCCGCAGACGGTC
TCGCATTCCACGAGCCAGGTGAGCTCTGGCCGTTCGGGGTCAAAAACCAGGTTTCCCCCA
TGCTTTTTGATGCGTTTCTTACCTCTGGTTTCCATGAGCCGGTGTCCACGCTCGGTGACG
AAAAGGCTGTCCGTGTCCCCGTATACAGACTNNNGTTTAAACGAATTCNNNATATAAAAT
GCAAGGTGCTGCTCAAAAAATCAGGCAAAGCCTCGCGCAAAAAAGAAAGCACATCGTAGT
CATGCTCATGCAGATAAAGGCAGGTAAGCTCCGGAACCACCACAGAAAAAGACACCATTT
TTCTCTCAAACATGTCTGCGGGTTTCTGCATAAACACAAAATAAAATAACAAAAAAACAT
TTAAACATTAGAAGCCTGTCTTACAACAGGAAAAACAACCCTTATAAGCATAAGACGGAC
TACGGCCATGCCGGCGTGACCGTAAAAAAACTGGTCACCGTGATTAAAAAGCACCACCGA
CAGCTCCTCGGTCATGTCCGGAGTCATAATGTAAGACTCGGTAAACACATCAGGTTGATT
CATCGGTCAGTGCTAAAAAGCGACCGAAATAGCCCGGGGAATACATACCCGCAGGCGTA
GAGACAACATTACAGCCCCCATAGGAGGTATAACAAAATTAATAGGAGAGAAAAACACAT
AAACACCTGAAAAACCCTCCTGCCTAGGCAAAATAGCACCCTCCCGCTCCAGAACAACAT
ACAGCGCTTCACAGCGGCAGCCTAACAGTCAGCCTTACCAGTAAAAAAGAAAACCTATTA
AAAAAACACCACTCGACACGGCACCAGCTCAATCAGTCACAGTGTAAAAAAGGGCCAAGT
GCAGAGCGAGTATATATAGGACTAAAAAATGACGTAACGGTTAAAGTCCACAAAAAACAC
CCAGAAAACCGCACGCGAACCTACGCCCAGAAACGAAAGCCAAAAAACCCACAACTTCCT
CAAATCGTCACTTCCGTTTTCCCACGTTACGTAACTTCCCATTTTAAGAAAACTACAATT
CCCAACACATACAAGTTACTCCGCCCTAAAACCTACGTCACCCGCCCCGTTCCCACGCCC
CGCGCCACGTCACAAACTCCACCCCCTCATTATCATATTGGCTTCAATCCAAAATAAGGT
ATATTATTGATGATNNNNTTAATTAAGGATCCNNNCGGTGTGAAATACCGCACAGATGCGT
AAGGAGAAAATACCGCATCAGGCGCTCTTCCGCTTCCTCGCTCACTGACTCGCTGCGCTC
GGTCGTTCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCTGACGAGCATCA
CAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGG
TGCTACAGAGTTCTTGAAGTGGTGGCCTAACTACGGCTACACTAGAAGGACAGTATTTGG
TATCTGCGCTCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTGGTC
TGACAGTTACCAATGCTTAATCAGTGAGGCACCTATCTCAGCGATCTGTCTATTTCGTTC
```

Figure 24 (part 4 of 5)

```
ATCCATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTT
GCGCAACGTTGTTGNNNNAAAAAGGATCTTCACCTAGATCCTTTTCACGTAGAAAGCCAG
TCCGCAGAAACGGTGCTGACCCCGGATGAATGTCAGCTACTGGGCTATCTGGACAAGGGA
AAACGCAAGCGCAAAGAGAAAGCAGGTAGCTTGCAGTGGGCTTACATGGCGATAGCTAGA
CTGGGCGGTTTTATGGACAGCAAGCGAACCGGAATTGCCAGCTGGGGCGCCCTCTGGTAA
GGTTGGGAAGCCCTGCAAAGTAAACTGGATGGCTTTCTCGCCGCCAAGGATCTGATGGCG
CAGGGATCAAGCTCTGATCAAGAGACAGGATGAGGATCGTTTCGCATGATTGAACAAGA
TGGATTGCACGCAGGTTCTCCGGCCGCTTGGGTGGAGAGGCTATTCGGCTATGACTGGGC
ACAACAGACAATCGGCTGCTCTGATGCCGCCGTGTTCCGGCTGTCAGCGCAGGGGCGCCC
GGTTCTTTTTGTCAAGACCGACCTGTCCGGTGCCCTGAATGAACTGCAAGACGAGGCAGC
GCGGCTATCGTGGCTGGCCACGACGGGCGTTCCTTGCGCAGCTGTGCTCGACGTTGTCAC
TGAAGCGGGAAGGGACTGGCTGCTATTGGGCGAAGTGCCGGGGCAGGATCTCCTGTCATC
TCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACG
TACTCGGATGGAAGCCGGTCTTGTCGATCAGGATGATCTGGACGAAGAGCATCAGGGGCT
CGCGCCAGCCGAACTGTTCGCCAGGCTCAAGGCGAGCATGCCCGACGGCGAGGATCTCGT
CGTGACCCATGGCGATGCCTGCTTGCCGAATATCATGGTGGAAAATGGCCGCTTTTCTGG
ATTCATCGACTGTGGCCGGCTGGGTGTGGCGGACCGCTATCAGGACATAGCGTTGGCTAC
CCGTGATATTGCTGAAGAGCTTGGCGGCGAATGGGCTGACCGCTTCCTCGTGCTTTACGG
TATCGCCGCTCCCGATTCGCAGCGCATCGCCTTCTATCGCCTTCTTGACGAGTTCTTCTG
AATTTTGTTAAAATTTTTGTTAAATCAGCTCATTTTTTAACCAATAGGCCGAAATCGGCA
ACATCCCTTATAAATCAAAAGAATAGACCGCGATAGGGTTGAGTGTTGTTCCAGTTTGGA
ACAAGAGTCCACTATTAAAGAACGTGGACTCCAACGTCAAAGGGCGAAAAACCGTCTATC
AGGGCGATGGCCCACTACGTGAACCATCACCCAAATCAAGTTTTTTGCGGTCGAGGTGCC
GTAAAGCTCTAAATCGGAACCCTAAAGGGAGCCCCGATTTAGAGCTTGACGGGGAAAGC
CGGCGAACGTGGCGAGAAAGGAAGGGAAGAAAGCGAAAGGAGCGGGCGCTAGGGCGCTGG
CAAGTGTAGCGGTCACGCTGCGCGTAACCACCACACCCGCGCGCTT
```

Figure 24 (part 5 of 5)

```
AATGCGCCGNNNNNNNNNNNNNNNNNNNNNNNNNNNNNNTTAATTAANNNNTCCCTTCCAGCTCTCT
GCCCCTTTTGGATTGAAGCCAATATGATAATGAGGGGGTGGAGTTTGTGACGTGGCGCGG
GGCGTGGGAACGGGGCGGGTGACGTAGTAGTGTGGCGGAAGTGTGATGTTGCAAGTGTGG
CGGAACACATGTAAGCGACGGATGTGGCAAAAGTGACGTTTTTGGTGTGCGCCGGTGTAC
ACAGGAAGTGACAATTTTCGCGCGGTTTTAGGCGGATGTTGTAGTAAATTTGGGCGTAAC
CGAGTAAGATTTGGCCATTTTCGCGGGAAAACTGAATAAGAGGAAGTGAAATCTGAATAA
TTTTGTGTTACTCATAGCGCGTAANNNNNTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATGGCC
CGCCTGGCATTATGCCCAGTACATGACCTTATGGGACTTTCCTACTTGGCAGTACATCTA
CGTATTAGTCATCGCTATTACCATGGTGATGCGGTTTTGGCAGTACATCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCCATTGAC
GCAAATGGGCGGTAGGCGTGTACGGTGGGAGGTCTATATAAGCAGAGCTGGTTTAGTGAA
CCGTCAGATCCGCTAGAGATCTGGATCCGAATTCGCCGCCACCATGGGTCCTCAGAAGCT
AACCATCTCCTGGTTTGCCATCGTTTTGCTGGTGTCTCCACTCATGGCCATGTGGGAGCT
GGAGAAAGACGTTTATGTTGTAGAGGTGGACTGGACTCCCGATGCCCCTGGAGAAACAGT
GAACCTCACCTGTGACACGCCTGAAGAAGATGACATCACCTGGACCTCAGACCAGAGACA
TGGAGTCATAGGCTCTGGAAAGACCCTGACCATCACTGTCAAAGAGTTTCTAGATGCTGG
CCAGTACACCTGCCACAAAGGAGGCGAGACTCTGAGCCACTCACATCTGCTGCTCCACAA
GAAGGAAAATGGAATTTGGTCCACTGAAATTTTAAAAAATTTCAAAAACAAGACTTTCCT
GAAGTGTGAAGCACCAAATTACTCCGGACGGTTCACGTGCTCATGGCTGGTGCAAAGAAA
CATGGACTTGAAGTTCAACATCAAGAGCAGTAGCAGTTCCCCTGACTCTCGGGCAGTGAC
ATGTGGAATGGCGTCTCTGTCTGCAGAGAAGGTCACACTGGACCAAAGGGACTATGAGAA
GTATTCAGTGTCCTGCCAGGAGGATGTCACCTGCCCAACTGCCGAGGAGACCCTGCCCAT
TGAACTGGCGTTGGAAGCACGGCAGCAGAATAAATATGAGAACTACAGCACCAGCTTCTT
CATCAGGGACATCATCAAACCAGACCCGCCCAAGAACTTGCAGATGAAGCCTTTGAAGAA
CTCACAGGTGGAGGTCAGCTGGGAGTACCCTGACTCCTGGAGCACTCCCCATTCCTACTT
CTCCCTCAAGTTCTTTGTTCGAATCCAGCGCAAGAAAGAAAAGATGAAGGAGACAGAGGA
GGGGTGTAACCAGAAAGGTGCGTTCCTCGTAGAGAAGACATCTACCGAAGTCCAATGCAA
AGGCGGGAATGTCTGCGTGCAAGCTCAGGATCGCTATTACAATTCCTCATGCAGCAAGTG
GGCATGTGTTCCCTGCAGGGTCCGATCCGGTGGCGGTGGCTCGGCGGTGGTGGGTCGGG
TGGCGGCGGATCTAGGGTCATTCCAGTCTCTGGACCTGCCAGGTGTCTTAGCCAGTCCCG
AAACCTGCTGAAGACCACAGATGACATGGTGAAGACGGCCAGAGAAAAGCTGAAACATTA
TTCCTGCACTGCTGAAGACATCGATCATGAAGACATCACACGGGACCAAACCAGCACATT
GAAGACCTGTTTACCACTGGAACTACACAAGAACGAGAGTTGCCTGGCTACTAGAGAGAC
TTCTTCCACAACAAGAGGGAGCTGCCTGCCCCCACAGAAGACGTCTTTGATGATGACCCT
GTGCCTTGGTAGCATCTATGAGGACTTGAAGATGTACCAGACAGAGTTCCAGGCCATCAA
```

Figure 25 (part 1 of 5)

```
CGCAGCACTTCAGAATCACAACCATCAGCAGATCATTCTAGACAAGGGCATGCTGGTGGC
CATCGATGAGCTGATGCAGTCTCTGAATCATAATGGCGAGACTCTGCGCCAGAAACCTCC
TGTGGGAGAAGCAGACCCTTACAGAGTGAAAATGAAGCTCTGCATCCTGCTTCACGCCTT
CAGCACCCGCGTCGTGACCATCAACAGGGTGATGGGCTATCTGAGCTCCGCCTGAGAATT
GATCCGGATTAGTCCAATTTGTTAAAGACAGGATGAAGCTTAAAACAGCTCTGGGGTTGT
ACCCACCCCAGAGGCCCACGTGGCGGCTAGTACTCCGGTATTGCGGTACCCTTGTACGCC
TGTTTTATACTCCCTTCCCGTAACTTAGACGCACAAAACCAAGTTCAATAGAAGGGGGTA
CAAACCAGTACCACCACGAACAAGCACTTCTGTTTCCCCGGTGATGTCGTATAGACTGCT
TGCGTGGTTGAAAGCGACGGATCCGTTATCCGCTTATGTACTTCGAGAAGCCCAGTACCA
CCTCGGAATCTTCGATGCGTTGCGCTCAGCACTCAACCCCAGAGTGTAGCTTAGGCTGAT
GAGTCTGGACATCCCTCACCGGTGACGGTGGTCCAGGCTGCGTTGGCGGCCTACCTATGG
CTAACGCCATGGGACGCTAGTTGTGAACAAGGTGTGAAGAGCCTATTGAGCTACATAAGA
ATCCTCCGGCCCCTGAATGCGGCTAATCCCAACCTCGGAGCAGGTGGTCACAAACCAGTG
ATTGGCCTGTCGTAACGCGCAAGTCCGTGGCGGAACCGACTACTTTGGGTGTCCGTGTTT
CCTTTTATTTTATTGTGGCTGCTTATGGTGACAATCACAGATTGTTATCATAAAGCGAAT
TGGATTGCGGCCGCGCCACCATGGACCAGCACACACTTGATGTGGAGGATACCGCGGATG
CCAGACATCCAGCAGGTACTTCGTGCCCCTCGGATGCGGCGCTCCTCAGAGATACCGGGC
TCCTCGCGGACGCTGCGCTCCTCTCAGATACTGTGCGCCCCACAAATGCCGCGCTCCCCA
CGGATGCTGCCTACCCTGCGGTTAATGTTCGGGATCGCGAGGCCGCGTGGCCGCCTGCAC
TGAACTTCTGTTCCCGCCACCCAAAGCTCTATGGCCTAGTCGCTTTGGTTTTGCTGCTTC
TGATCGCCGCCTGTGTTCCTATCTTCACCCGCACCGAGCCTCGGCCAGCGCTCACAATCA
CCACCTCGCCCAACCTGGGTACCCGAGAGAATAATGCAGACCAGGTCACCCCTGTTTCCC
ACATTGGCTGCCCCAACACTACACAACAGGGCTCTCCTGTGTTCGCCAAGCTACTGGCTA
AAAACCAAGCATCGTTGTGCAATACAACTCTGAACTGGCACAGCCAAGATGGAGCTGGGA
GCTCATACCTATCTCAAGGTCTGAGGTACGAAGAAGACAAAAAGGAGTTGGTGGTAGACA
GTCCCGGGCTCTACTACGTATTTTTGGAACTGAAGCTCAGTCCAACATTCACAAACACAG
GCCACAAGGTGCAGGGCTGGGTCTCTCTTGTTTTGCAAGCAAAGCCTCAGGTAGATGACT
TTGACAACTTGGCCCTGACAGTGGAACTGTTCCCTTGCTCCATGGAGAACAAGTTAGTGG
ACCGTTCCTGGAGTCAACTGTTGCTCCTGAAGGCTGGCCACCGCCTCAGTGTGGGTCTGA
GGGCTTATCTGCATGGAGCCCAGGATGCATACAGAGACTGGGAGCTGTCTTATCCCAACA
CCACCAGCTTTGGACTCTTTCTTGTGAAACCCGACAACCCATGGGAATGAGAACTATCCT
TCTTGTGACTGGCGCGATCCGATCCACCGGATCTAGATAACTGATCATAATCAGCCATAC
CACATTTGTAGAGGTTTTACTTGCTTTAAAAAACCTCCCACACCTCCCCCTGAACCTGAA
ACATAAAATGAATGCAATTGTTGTTGTTAACTTGTTTATTGCAGCTTATAATGGTTACAA
ATAAAGCAATAGCATCACAAATTTCACAAATAAAGCATTTTTTTCACTGCATTCTAGTTG
TGGTTTGTCCAAACTCATCAATGTATCTTAACGCNNNNTAAGGGTGGGAAAGAATATATA
AGGTGGGGGTCTTATGTAGTTTTGTATCTGTTTGCAGCAGCCGCCGCCGCCATGAGCAC
CAACTCGTTTGATGGAAGCATTGTGAGCTCATATTTGACAACGCGCATGCCCCCATGGGC
CGGGGTGCGTCAGAATGTGATGGGCTCCAGCATTGATGGTCGCCCCGTCCTGCCCGCAAA
CTCTACTACCTTGACCTACGAGACCGTGTCTGGAACGCCGTTGGAGACTGCAGCCTCCGC
CGCCGCTTCAGCCGCTGCAGCCACCGCCCGCGGGATTGTGACTGACTTTGCTTTCCTGAG
CCCGCTTGCAAGCAGTGCAGCTTCCCGTTCATCCGCCCGCGATGACAAGTTGACGGCTCT
```

Figure 25 (part 2 of 5)

```
TTTGGCACAATTGGATTCTTTGACCCGGGAACTTAATGTCGTTTCTCAGCAGCTGTTGGA
TCTGCGCCAGCAGGTTTCTGCCCTGAAGGCTTCCTCCCCTCCCAATGCGGTTTAAAACAT
AAATAAAAAACCAGACTCTGTTTGGATTTGGATCAAGCAAGTGTCTTGCTGTCTTTATTT
AGGGGTTTTGCGCGCGCGGTAGGCCCGGGACCAGCGGTCTCGGTCGTTGAGGGTCCTGTG
TATTTTTTCCAGGACGTGGTAAAGGTGACTCTGGATGTTCAGATACATGGGCATAAGCCC
GTCTCTGGGGTGGAGGTAGCACCACTGCAGAGCTTCATGCTGCGGGGTGGTGTTGTAGAT
GATCCAGTCGTAGCAGGAGCGCTGGGCGTGGTGCCTAAAAATGTCTTTCAGTAGCAAGCT
GATTGCCAGGGGCAGGCCCTTGGTGTAAGTGTTTACAAAGCGGTTAAGCTGGGATGGGTG
CATACGTGGGATATGAGATGCATCTTGGACTGTATTTTTAGGTTGGCTATGTTCCCAGC
CATATCCCTCCGGGATTCATGTTGTGCAGAACCACCAGCACAGTGTATCCGGTGCACTT
GGGAAATTTGTCATGTAGCTTAGAAGGAAATGCGTGGAAGAACTTGGAGACGCCCTTGTG
ACCTCCAAGATTTTCCATGCATTCGTCCATAATGATGGCAATGGGCCCACGGGCGGCGGC
CTGGGCGAAGATATTTCTGGGATCACTAACGTCATAGTTGTGTTCCAGGATGAGATCGTC
ATAGGCCATTTTTACAAAGCGCGGGCGGAGGGTGCCAGACTGCGGTATAATGGTTCCATC
CGGCCCAGGGGCGTAGTTACCCTCACAGATTTGCATTTCCCACGCTTTGAGTTCAGATGG
GGGGATCATGTCTACCTGCGGGGCGATGAAGAAAACGGTTTCCGGGGTAGGGAGATCAG
CTGGCAAGAAAGCAGGTTCCTGAGCAGCTGCGACTTACCGCAGCCGGTGGGCCCGTAAAT
CACACCTATTACCGGGTGCAACTGGTAGTTAAGAGAGCTGCAGCTGCCGTCATCCCTGAG
CAGGGGGGCCACTTCGTTAAGCATGTCCCTGACTCGCATGTTTTCCCTGACCAAATCCGC
CAGAAGGCGCTCGCCGCCCAGCGATAGCAGTTCTTGCAAGGAAGCAAAGTTTTTCAACGG
TTTGAGACCGTCCGCCGTAGGCATGCTTTTGAGCGTTTGACCAAGCAGTTCCAGGCGGTC
CCACAGCTCGGTCACCTGCTCTACGGCATCTCGATCCAGCATATCTCCTCGTTTCGCGGG
TTGGGGCGGCTTTCGCTGTACGGCAGTAGTCGGTGCTCGTCCAGACGGGCCAGGGTCATG
TCTTTCCACGGGCGCAGGGTCCTCGTCAGCGTAGTCTGGGTCACGGTGAAGGGGTGCGCT
CCGGGCTGCGCGCTGGCCAGGGTGCGCTTGAGGCTGGTCCTGCTGGTGCTGAAGCGCTGC
CGGTCTTCGCCCTGCGCGTCGGCCAGGTAGCATTTGACCATGGTGTCATAGTCCAGCCCC
TCCGCGGCGTGGCCCTTGGCGCGCAGCTTGCCCTTGGAGGAGGCGCCGCACGAGGGGCAG
TGCAGACTTTTGAGGGCGTAGAGCTTGGGCGCGAGAAATACCGATTCCGGGGAGTAGGCA
TCCGCGCCGCAGGCCCCGCAGACGGTCTCGCATTCCACGAGCCAGGTGAGCTCTGGCCGT
TCGGGGTCAAAAACCAGGTTTCCCCCATGCTTTTTGATGCGTTTCTTACCTCTGGTTTCC
ATGAGCCGGTGTCCACGCTCGGTGACGAAAAGGCTGTCCGTGTCCCCGTATACAGACTNN
NGTTTAAACGAATTCNNNATATAAAATGCAAGGTGCTGCTCAAAAAATCAGGCAAAGCCT
CGCGCAAAAAAGAAAGCACATCGTAGTCATGCTCATGCAGATAAAGGCAGGTAAGCTCCG
GAACCACCACAGAAAAGACACCATTTTTCTCTCAAACATGTCTGCGGGTTTCTGCATAA
ACACAAAATAAAATAACAAAAAAACATTTAAACATTAGAAGCCTGTCTTACAACAGGAAA
AACAACCCTTATAAGCATAAGACGGACTACGGCCATGCCGGCGTGACCGTAAAAAAACTG
GTCACCGTGATTAAAAAGCACCACCGACAGCTCCTCGGTCATGTCCGGAGTCATAATGTA
AGACTCGGTAAACACATCAGGTTGATTCATCGGTCAGTGCTAAAAAGCGACCGAAATAGC
CCGGGGGAATACATACCCGCAGGCGTAGAGACAACATTACAGCCCCCATAGGAGGTATAA
CAAAATTAATAGGAGAGAAAAACACATAAACACCTGAAAAACCCTCCTGCCTAGGCAAAA
TAGCACCCTCCCGCTCCAGAACAACATACAGCGCTTCACAGCGGCAGCCTAACAGTCAGC
CTTACCAGTAAAAAAGAAAACCTATTAAAAAAACACCACTCGACACGGCACCAGCTCAAT
```

Figure 25 (part 3 of 5)

```
CAGTCACAGTGTAAAAAAGGGCCAAGTGCAGAGCGAGTATATATAGGACTAAAAAATGAC
GTAACGGTTAAAGTCCACAAAAAACACCCAGAAAACCGCACGCGAACCTACGCCCAGAAA
CGAAAGCCAAAAAACCCACAACTTCCTCAAATCGTCACTTCCGTTTTCCCACGTTACGTA
ACTTCCCATTTTAAGAAAACTACAATTCCCAACACATACAAGTTACTCCGCCCTAAAACC
TACGTCACCCGCCCCGTTCCCACGCCCCGCGCCACGTCACAAACTCCACCCCCTCATTAT
CATATTGGCTTCAATCCAAAATAAGGTATATTATTGATGATNNNTTAATTAAGGATCCNN
NCGGTGTGAAATACCGCACAGATGCGTAAGGAGAAAATACCGCATCAGGCGCTCTTCCGC
TTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCT
GGGCTGTGTGCACGAACCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAGAT
AACTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGNNNNNAAAAAGGATCTTCAC
CTAGATCCTTTTCACGTAGAAAGCCAGTCCGCAGAAACGGTGCTGACCCCGGATGAATGT
CAGCTACTGGGCTATCTGGACAAGGGAAAACGCAAGCGCAAAGAGAAAGCAGGTAGCTTG
CAGTGGGCTTACATGGCGATAGCTAGACTGGGCGGTTTTATGGACAGCAAGCGAACCGGA
ATTGCCAGCTGGGGCGCCCTCTGGTAAGGTTGGGAAGCCCTGCAAAGTAAACTGGATGGC
TTTCTCGCCGCCAAGGATCTGATGGCGCAGGGGATCAAGCTCTGATCAAGAGACAGGATG
AGGATCGTTTCGCATGATTGAACAAGATGGATTGCACGCAGGTTCTCCGGCCGCTTGGGT
GGAGAGGCTATTCGGCTATGACTGGGCACAACAGACAATCGGCTGCTCTGATGCCGCCGT
GTTCCGGCTGTCAGCGCAGGGGCGCCCGGTTCTTTTTGTCAAGACCGACCTGTCCGGTGC
CCTGAATGAACTGCAAGACGAGGCAGCGCGGCTATCGTGGCTGGCCACGACGGGCGTTCC
TTGCGCAGCTGTGCTCGACGTTGTCACTGAAGCGGGAAGGGACTGGCTGCTATTGGGCGA
AGTGCCGGGGCAGGATCTCCTGTCATCTCACCTTGCTCCTGCCGAGAAAGTATCCATCAT
GGCTGATGCAATGCGGCGGCTGCATACGCTTGATCCGGCTACCTGCCCATTCGACCACCA
AGCGAAACATCGCATCGAGCGAGCACGTACTCGGATGGAAGCCGGTCTTGTCGATCAGGA
TGATCTGGACGAAGAGCATCAGGGGCTCGCGCCAGCCGAACTGTTCGCCAGGCTCAAGGC
```

```
GAGCATGCCCGACGGCGAGGATCTCGTCGTGACCCATGGCGATGCCTGCTTGCCGAATAT
CATGGTGGAAAATGGCCGCTTTTCTGGATTCATCGACTGTGGCCGGCTGGGTGTGGCGGA
CCGCTATCAGGACATAGCGTTGGCTACCCGTGATATTGCTGAAGAGCTTGGCGGCGAATG
GGCTGACCGCTTCCTCGTGCTTTACGGTATCGCCGCTCCCGATTCGCAGCGCATCGCCTT
CTATCGCCTTCTTGACGAGTTCTTCTGAATTTTGTTAAAATTTTTGTTAAATCAGCTCAT
TTTTTAACCAATAGGCCGAAATCGGCAACATCCCTTATAAATCAAAAGAATAGACCGCGA
TAGGGTTGAGTGTTGTTCCAGTTTGGAACAAGAGTCCACTATTAAAGAACGTGGACTCCA
ACGTCAAAGGGCGAAAAACCGTCTATCAGGGCGATGGCCCACTACGTGAACCATCACCCA
AATCAAGTTTTTTGCGGTCGAGGTGCCGTAAAGCTCTAAATCGGAACCCTAAAGGGAGCC
CCCGATTTAGAGCTTGACGGGGAAAGCCGGCGAACGTGGCGAGAAAGGAAGGGAAGAAAG
CGAAAGGAGCGGGCGCTAGGGCGCTGGCAAGTGTAGCGGTCACGCTGCGCGTAACCACCA
CACCCGCGCGCTT
```

Figure 25 (part 5 of 5)

```
AATGCGCCGNNNNNNNNNNNNNNNNNNNNNNNNNNTTAATTAANNNNTCCCTTCCAGCTCTCT
GCCCCTTTTGGATTGAAGCCAATATGATAATGAGGGGTGGAGTTTGTGACGTGGCGCGG
GGCGTGGGAACGGGGCGGGTGACGTAGTAGTGTGGCGGAAGTGTGATGTTGCAAGTGTGG
CGGAACACATGTAAGCGACGGATGTGGCAAAAGTGACGTTTTTGGTGTGCGCCGGTGTAC
ACAGGAAGTGACAATTTTCGCGCGGTTTTAGGCGGATGTTGTAGTAAATTTGGGCGTAAC
CGAGTAAGATTTGGCCATTTTCGCGGGAAAACTGAATAAGAGGAAGTGAAATCTGAATAA
TTTTGTGTTACTCATAGCGCGTAANNNNNTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATGGCC
CGCCTGGCATTATGCCCAGTACATGACCTTATGGGACTTTCCTACTTGGCAGTACATCTA
CGTATTAGTCATCGCTATTACCATGGTGATGCGGTTTTGGCAGTACATCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCCATTGAC
GCAAATGGGCGGTAGGCGTGTACGGTGGGAGGTCTATATAAGCAGAGCTGGTTTAGTGAA
CCGTCAGATCCGCTAGAGATCTGGATCCGAATTCGCCGCCACCATGGGTCCTCAGAAGCT
AACCATCTCCTGGTTTGCCATCGTTTTGCTGGTGTCTCCACTCATGGCCATGTGGGAGCT
GGAGAAAGACTTTTATGTTGTAGAGGTGGACTGGACTCCCGATGCCCCTGGAGAAACAGT
GAACCTCACCTGTGACACGCCTGAAGAAGATGACATCACCTGGACCTCAGACCAGAGACA
TGGAGTCATAGGCTCTGGAAAGACCCTGACCATCACTGTCAAAGAGTTTCTAGATGCTGG
CCAGTACACCTGCCACAAAGGAGGCGAGACTCTGAGCCACTCACATCTGCTGCTCCACAA
GAAGGAAAATGGAATTTGGTCCACTGAAATTTTAAAAAATTTCAAAAACAAGACTTTCCT
GAAGTGTGAAGCACCAAATTACTCCGGACGGTTCACGTGCTCATGGCTGGTGCAAAGAAA
CATGGACTTGAAGTTCAACATCAAGAGCAGTAGCAGTTCCCCTGACTCTCGGGCAGTGAC
ATGTGGAATGGCGTCTCTGTCTGCAGAGAAGGTCACACTGGACCAAAGGGACTATGAGAA
GTATTCAGTGTCCTGCCAGGAGGATGTCACCTGCCCAACTGCCGAGGAGACCCTGCCCAT
TGAACTGGCGTTGGAAGCACGGCAGCAGAATAAATATGAGAACTACAGCACCAGCTTCTT
CATCAGGGACATCATCAAACCAGACCCGCCCAAGAACTTGCAGATGAAGCCTTTGAAGAA
CTCACAGGTGGAGGTCAGCTGGGAGTACCCTGACTCCTGGAGCACTCCCCATTCCTACTT
CTCCCTCAAGTTCTTTGTTCGAATCCAGCGCAAGAAAGAAAAGATGAAGGAGACAGAGGA
GGGGTGTAACCAGAAAGGTGCGTTCCTCGTAGAGAAGACATCTACCGAAGTCCAATGCAA
AGGCGGGAATGTCTGCGTGCAAGCTCAGGATCGCTATTACAATTCCTCATGCAGCAAGTG
GGCATGTGTTCCCTGCAGGGTCCGATCCGGTGGCGGTGGCTCGGGCGGTGGTGGGTCGGG
TGGCGGCGGATCTAGGGTCATTCCAGTCTCTGGACCTGCCAGGTGTCTTAGCCAGTCCCG
AAACCTGCTGAAGACCACAGATGACATGGTGAAGACGGCCAGAGAAAGCTGAAACATTA
TTCCTGCACTGCTGAAGACATCGATCATGAAGACATCACACGGGACCAAACCAGCACATT
GAAGACCTGTTTACCACTGGAACTACACAAGAACGAGAGTTGCCTGGCTACTAGAGAGAC
TTCTTCCACAACAAGAGGGAGCTGCCTGCCCCACAGAAGACGTCTTTGATGATGACCCT
GTGCCTTGGTAGCATCTATGAGGACTTGAAGATGTACCAGACAGAGTTCCAGGCCATCAA
```

Figure 26 (part 1 of 4)

```
CGCAGCACTTCAGAATCACAACCATCAGCAGATCATTCTAGACAAGGGCATGCTGGTGGC
CATCGATGAGCTGATGCAGTCTCTGAATCATAATGGCGAGACTCTGCGCCAGAAACCTCC
TGTGGGAGAAGCAGACCCTTACAGAGTGAAAATGAAGCTCTGCATCCTGCTTCACGCCTT
CAGCACCCGCGTCGTGACCATCAACAGGGTGATGGGCTATCTGAGCTCCGCCTGAGAATT
GATCCGGATTAGTCCAATTTGTTAAAGACAGGATGAAGCTTCTAGATAAGATATCCGATC
CACCGGATCTAGATAACTGATCATAATCAGCCATACCACATTTGTAGAGGTTTTACTTGC
TTTAAAAAACCTCCCACACCTCCCCCTGAACCTGAAACATAAAATGAATGCAATTGTTGT
TGTTAACTTGTTTATTGCAGCTTATAATGGTTACAAATAAAGCAATAGCATCACAAATTT
CACAAATAAAGCATTTTTTTCACTGCATTCTAGTTGTGGTTTGTCCAAACTCATCAATGT
ATCTTAACGCNNNNTAAGGGTGGGAAAGAATATATAAGGTGGGGTCTTATGTAGTTTTG
TATCTGTTTTGCAGCAGCCGCCGCCGCCATGAGCACCAACTCGTTTGATGGAAGCATTGT
GAGCTCATATTTGACAACGCGCATGCCCCATGGGCCGGGGTGCGTCAGAATGTGATGGG
CTCCAGCATTGATGGTCGCCCCGTCCTGCCCGCAAACTCTACTACCTTGACCTACGAGAC
CGTGTCTGGAACGCCGTTGGAGACTGCAGCCTCCGCCGCCGCTTCAGCCGCTGCAGCCAC
CGCCCGCGGGATTGTGACTGACTTTGCTTTCCTGAGCCCGCTTGCAAGCAGTGCAGCTTC
CCGTTCATCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTTCTGCCCT
GAAGGCTTCCTCCCCTCCCAATGCGGTTTAAAACATAAATAAAAAACCAGACTCTGTTTG
GATTTGGATCAAGCAAGT TCTTGCTGTCTTTATTTAGGGGTTTTGCGCGCGCGGTAGGC
CCGGGACCAGCGGTCTCG TCGTTGAGGGTCCTGTGTATTTTTTCCAGGACGTGGTAAAG
GTGACTCTGGATGTTCAG TACATGGGCATAAGCCCGTCTCTGGGGTGGAGGTAGCACCA
CTGCAGAGCTTCATGCTG GGGGTGGTGTTGTAGATGATCCAGTCGTAGCAGGAGCGCTG
GGCGTGGTGCCTAAAAAT TCTTTCAGTAGCAAGCTGATTGCCAGGGGCAGGCCCTTGGT
GTAAGTGTTTACAAAGCGGTTAAGCTGGGATGGGTGCATACGTGGGGATATGAGATGCAT
CTTGGACTGTATTTTTAGCTTGGCTATGTTCCCAGCCATATCCCTCCGGGGATTCATGTT
GTGCAGAACCACCAGCACAGTGTATCCGGTGCACTTGGGAAATTTGTCATGTAGCTTAGA
AGGAAATGCGTGGAAGAA TTGGAGACGCCCTTGTGACCTCCAAGATTTTCCATGCATTC
GTCCATAATGATGGCAATC GCCCACGGGCGGCGGCCTGGGCGAAGATATTTCTGGGATC
ACTAACGTCATAGTTGTGT TCCAGGATGAGATCGTCATAGGCCATTTTTACAAAGCGCGG
GCGGAGGGTGCCAGACTGCGGTATAATGGTTCCATCCGGCCCAGGGGCGTAGTTACCCTC
ACAGATTTGCATTTCCCAC CTTTGAGTTCAGATGGGGGATCATGTCTACCTGCGGGGC
GATGAAGAAAACGGTTTCCGGGGTAGGGGAGATCAGCTGGGAAGAAAGCAGGTTCCTGAG
CAGCTGCGACTTACCGCAGCCGGTGGGCCCGTAAATCACACCTATTACCGGGTGCAACTG
GTAGTTAAGAGAGCTGCAG TGCCGTCATCCCTGAGCAGGGGGCCACTTCGTTAAGCAT
GTCCCTGACTCGCATGTTTTCCCTGACCAAATCCGCCAGAAGCGCTCGCCGCCCAGCGA
TAGCAGTTCTTGCAAGGAAGCAAAGTTTTTCAACGGTTTGAGACCGTCCGCCGTAGGCAT
GCTTTTGAGCGTTTGACCAAGCAGTTCCAGGCGGTCCCACAGCTCGGTCACCTGCTCTAC
GGCATCTCGATCCAGCATATCTCCTCGTTTCGCGGGTTGGGCGGCTTTCGCTGTACGGC
AGTAGTCGGTGCTCGTCCAGACGGGCCAGGGTCATGTCTTTCCACGGGCGCAGGGTCCTC
GTCAGCGTAGTCTGGGTCACGGTGAAGGGTGCGCTCCGGGCTGCGCGCTGGCCAGGGTG
CGCTTGAGGCTGGTCCTGCTGGTGCTGAAGCGCTGCCGGTCTTCGCCCTGCGCGTCGGCC
AGGTAGCATTTGACCATGGTGTCATAGTCCAGCCCCTCCGCGGCGTGGCCCTTGGCGCGC
```

Figure 26 (part 2 of 4)

```
AGCTTGCCCTTGGAGGAGGCGCCGCACGAGGGGCAGTGCAGACTTTTGAGGGCGTAGAGC
TTGGGCGCGAGAAATACCGATTCCGGGGAGTAGGCATCCGCGCCGCAGGCCCCGCAGACG
GTCTCGCATTCCACGAGCCAGGTGAGCTCTGGCCGTTCGGGGTCAAAAACCAGGTTTCCC
CCATGCTTTTTGATGCGTTTCTTACCTCTGGTTTCCATGAGCCGGTGTCCACGCTCGGTG
ACGAAAAGGCTGTCCGTGTCCCCGTATACAGACTNNNGTTTAAACGAATTCNNNATATAA
AATGCAAGGTGCTGCTCAAAAAATCAGGCAAAGCCTCGCGCAAAAAGAAAGCACATCGT
AGTCATGCTCATGCAGATAAAGGCAGGTAAGCTCCGGAACCACCACAGAAAAGACACCA
TTTTTCTCTCAAACATGTCTGCGGGTTTCTGCATAAACACAAAATAAAATAACAAAAAA
CATTTAAACATTAGAAGCCTGTCTTACAACAGGAAAAACAACCCTTATAAGCATAAGACG
GACTACGGCCATGCCGGCGTGACCGTAAAAAAACTGGTCACCGTGATTAAAAAGCACCAC
CGACAGCTCCTCGGTCATGTCCGGAGTCATAATGTAAGACTCGGTAAACACATCAGGTTG
ATTCATCGGTCAGTGCTAAAAAGCGACCGAAATAGCCCGGGGGAATACATACCCGCAGGC
GTAGAGACAACATTACAGCCCCCATAGGAGGTATAACAAAATTAATAGGAGAGAAAAACA
CATAAACACCTGAAAAACCCTCCTGCCTAGGCAAAATAGCACCCTCCCGCTCCAGAACAA
CATACAGCGCTTCACAGCGGCAGCCTAACAGTCAGCCTTACCAGTAAAAAAGAAAACCTA
TTAAAAAAACACCACTCGACACGGCACCAGCTCAATCAGTCACAGTGTAAAAAGGGCCA
AGTGCAGAGCGAGTATATATAGGACTAAAAAATGACGTAACGGTTAAAGTCCACAAAAAA
CACCCAGAAAACCGCACGCGAACCTACGCCCAGAAACGAAAGCCAAAAAACCCACAACTT.
CCTCAAATCGTCACTTCCGTTTTCCCACGTTACGTAACTTCCCATTTTAAGAAAACTACA
ATTCCCAACACATACAAGTTACTCCGCCCTAAAACCTACGTCACCCGCCCCGTTCCCACG
CCCCGCGCCACGTCACAAACTCCACCCCCTCATTATCATATTGGCTTCAATCCAAAATAA
GGTATATTATTGATGATNNNTTAATTAAGGATCCNNNCGGTGTGAAATACCGCACAGATG
CGTAAGGAGAAAATACCGCATCAGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCTGACGAGCA
TCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGGACAGTATT
TGGTATCTGCGCTCTGCTGAAGCCAGTTACCTTCGGAAAAAGAGTTGGTAGCTCTTGATC
CGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTA
GATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCGC
```

Figure 26 (part 3 of 4)

```
CTCCATCCAGTCTATTAATTGTTGCCGGGAAGCTAGAGTAAGTAGTTCGCCAGTTAATAG
TTTGCGCAACGTTGTTGNNNNNAAAAAGGATCTTCACCTAGATCCTTTTCACGTAGAAAGC
CAGTCCGCAGAAACGGTGCTGACCCCGGATGAATGTCAGCTACTGGGCTATCTGGACAAG
GGAAAACGCAAGCGCAAAGAGAAAGCAGGTAGCTTGCAGTGGGCTTACATGGCGATAGCT
AGACTGGGCGGTTTTATGGACAGCAAGCGAACCGGAATTGCCAGCTGGGGCGCCCTCTGG
TAAGGTTGGGAAGCCCTGCAAAGTAAACTGGATGGCTTTCTCGCCGCCAAGGATCTGATG
GCGCAGGGGATCAAGCTCTGATCAAGAGACAGGATGAGGATCGTTTCGCATGATTGAACA
AGATGGATTGCACGCAGGTTCTCCGGCCGCTTGGGTGGAGAGGCTATTCGGCTATGACTG
GGCACAACAGACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGCAAGACGAGGC
AGCGCGGCTATCGTGGCTGGCCACGACGGGCGTTCCTTGCGCAGCTGTGCTCGACGTTGT
CACTGAAGCGGGAAGGGACTGGCTGCTATTGGGCGAAGTGCCGGGGCAGGATCTCCTGTC
ATCTCACCTTGCTCCTGCCGAGAAAGTATCCATCATGGCTGATGCAATGCGGCGGCTGCA
TACGCTTGATCCGGCTACCTGCCCATTCGACCACCAAGCGAAACATCGCATCGAGCGAGC
ACGTACTCGGATGGAAGCCGGTCTTGTCGATCAGGATGATCTGGACGAAGAGCATCAGGG
GCTCGCGCCAGCCGAACTGTTCGCCAGGCTCAAGGCGAGCATGCCCGACGGCGAGGATCT
CGTCGTGACCCATGGCGATGCCTGCTTGCCGAATATCATGGTGGAAAATGGCCGCTTTTC
TGGATTCATCGACTGTGGCCGGCTGGGTGTGGCGGACCGCTATCAGGACATAGCGTTGGC
TACCCGTGATATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTGACGAGTTCTT
CTGAATTTTGTTAAAATTTTTGTTAAATCAGCTCATTTTTTAACCAATAGGCCGAAATCG
GCAACATCCCTTATAAATCAAAAGAATAGACCGCGATAGGGTTGAGTGTTGTTCCAGTTT
GGAACAAGAGTCCACTATTAAAGAACGTGGACTCCAACGTCAAAGGGCGAAAAACCGTCT
ATCAGGGCGATGGCCCACTACGTGAACCATCACCCAAATCAAGTTTTTTGCGGTCGAGGT
GCCGTAAAGCTCTAAATCGGAACCCTAAAGGGAGCCCCCGATTTAGAGCTTGACGGGGAA
AGCCGGCGAACGTGGCGAGAAAGGAAGGGAAGAAAGCGAAAGGAGCGGGCGCTAGGGCGC
TGGCAAGTGTAGCGGTCACGCTGCGCGTAACCACCACACCCGCGCGCTT
```

Figure 26 (part 4 of 4)

```
NNTTAATTAAGGATCCNNNCGGTGTGAAATACCGCACAGATGCGTAAGGAGAAAATACCG
CATCAGGCGCTCTTCCGCTTCCTCGCTCACTGACTCGCTGCGCTCGGTCGTTCGGCTGCG
GCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGC
GTTGCTGGCGTTTTTCCATAGGCTCCGCCCCCTGACGAGCATCACAAAAATCGACGCTC
AAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGC
AGCAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTAAAA
ATGAAGTTTTAAATCAATCTAAAGTATATATGAGTAAACTTGGTCTGACAGTTACCAATG
CTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCAACGTTGTTGN
NNNAAAAAGGATCTTCACCTAGATCCTTTTCACGTAGAAAGCCAGTCCGCAGAAACGGTG
CTGACCCCGGATGAATGTCAGCTACTGGGCTATCTGGACAAGGGAAAACGCAAGCGCAAA
GAGAAAGCAGGTAGCTTGCAGTGGGCTTACATGGCGATAGCTAGACTGGGCGGTTTTATG
GACAGCAAGCGAACCGGAATTGCCAGCTGGGGCGCCCTCTGGTAAGGTTGGGAAGCCCTG
CAAAGTAAACTGGATGGCTTTCTCGCCGCCAAGGATCTGATGGCGCAGGGGATCAAGCTC
TGATCAAGAGACAGGATGAGGATCGTTTCGCATGATTGAACAAGATGGATTGCACGCAGG
TTCTCCGGCCGCTTGGGTGGAGAGGCTATTCGGCTATGACTGGGCACAACAGACAATCGG
CTGCTCTGATGCCGCCGTGTTCCGGCTGTCAGCGCAGGGGCGCCCGGTTCTTTTTGTCAA
GACCGACCTGTCCGGTGCCCTGAATGAACTGCAAGACGAGGCAGCGCGGCTATCGTGGCT
GGCCACGACGGGCGTTCCTTGCGCAGCTGTGCTCGACGTTGTCACTGAAGCGGGAAGGGA
CTGGCTGCTATTGGGCGAAGTGCCGGGGCAGGATCTCCTGTCATCTCACCTTGCTCCTGC
CGAGAAAGTATCCATCATGGCTGATGCAATGCGGCGGCTGCATACGCTTGATCCGGCTAC
CTGCCCATTCGACCACCAAGCGAAACATCGCATCGAGCGAGCACGTACTCGGATGGAAGC
CGGTCTTGTCGATCAGGATGATCTGGACGAAGAGCATCAGGGGCTCGCGCCAGCCGAACT
GTTCGCCAGGCTCAAGGCGAGCATGCCCGACGGCGAGGATCTCGTCGTGACCCATGGCGA
TGCCTGCTTGCCGAATATCATGGTGGAAAATGGCCGCTTTTCTGGATTCATCGACTGTGG
CCGGCTGGGTGTGGCGGACCGCTATCAGGACATAGCGTTGGCTACCCGTGATATTGCTGA
```

Figure 27 (part 1 of 16)

```
AGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAATTTTGTTAAAATT
TTTGTTAAATCAGCTCATTTTTTAACCAATAGGCCGAAATCGGCAACATCCCTTATAAAT
CAAAAGAATAGACCGCGATAGGGTTGAGTGTTGTTCCAGTTTGGAACAAGAGTCCACTAT
TAAAGAACGTGGACTCCAACGTCAAAGGGCGAAAAACCGTCTATCAGGGCGATGGCCCAC
TACGTGAACCATCACCCAAATCAAGTTTTTTGCGGTCGAGGTGCCGTAAAGCTCTAAATC
GGAACCCTAAAGGGAGCCCCCGATTTAGAGCTTGACGGGGAAAGCCGGCGAACGTGGCGA
GAAAGGAAGGGAAGAAAGCGAAAGGAGCGGGCGCTAGGGCGCTGGCAAGTGTAGCGGTCA
CGCTGCGCGTAACCACCACACCCGCGCGCTTAATGCGCCGNNNNNNNNNNNNNNNNNNNN
NNNNNTTAATTAANNNNTCCCTTCCAGCTCTCTGCCCCTTTTGGATTGAAGCCAATATGATA
ATGAGGGGGTGGAGTTTGTGACGTGGCGCGGGCGTGGGAACGGGGCGGGTGACGTAGTA
GTGTGGCGGAAGTGTGATGTTGCAAGTGTGGCGGAACACATGTAAGCGACGGATGTGGCA
AAAGTGACGTTTTTGGTGTGCGCCGGTGTACACAGGAAGTGACAATTTTCGCGCGGTTTT
AGGCGGATGTTGTAGTAAATTTGGGCGTAACCGAGTAAGATTTGGCCATTTTCGCGGGAA
AACTGAATAAGAGGAAGTGAAATCTGAATAATTTTGTGTTACTCATAGCGCGTAANNNNT
AATAGTAATCAATTACGGGGTCATTAGTTCATAGCCCATATATGGAGTTCCGCGTTACAT
AACTTACGGTAAATGGCCCGCCTGGCTGACCGCCCAACGACCCCCGCCCATTGACGTCAA
TAATGACGTATGTTCCCATAGTAACGCCAATAGGGACTTTCCATTGACGTCAATGGGTGG
AGTATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGACCT
TATGGGACTTTCCTACTTGGCAGTACATCTACGTATTAGTCATCGCTATTACCATGGTGA
TGCGGTTTTGGCAGTACATCAATGGGCGTGGATAGCGGTTTGACTCACGGGATTTCCAA
GTCTCCACCCCATTGACGTCAATGGGAGTTTGTTTTGGCACCAAAATCAACGGGACTTTC
CAAAATGTCGTAACAACTCCGCCCCATTGACGCAAATGGGCGGTAGGCGTGTACGGTGGG
AGGTCTATATAAGCAGAGCTGGTTTAGTGAACCGTCAGATCCGCTAGAGATCTGGATCCG
AATTCGCCGCCACCATGGGTCCTCAGAAGCTAACCATCTCCTGGTTTGCCATCGTTTTGC
TGGTGTCTCCACTCATGGCCATGTGGGAGCTGGAGAAAGACGTTTATGTTGTAGAGGTGG
ACTGGACTCCCGATGCCCCTGGAGAAACAGTGAACCTCACCTGTGACACGCCTGAAGAAG
ATGACATCACCTGGACCTCAGACCAGAGACATGGAGTCATAGGCTCTGGAAAGACCCTGA
CCATCACTGTCAAAGAGTTTCTAGATGCTGGCCAGTACACCTGCCACAAAGGAGGCGAGA
CTCTGAGCCACTCACATCTGCTGCTCCACAAGAAGGAAAATGGAATTTGGTCCACTGAAA
TTTTAAAAAATTTCAAAAACAAGACTTTCCTGAAGTGTGAAGCACCAAATTACTCCGGAC
GGTTCACGTGCTCATGGCTGGTGCAAAGAAACATGGACTTGAAGTTCAACATCAAGAGCA
GTAGCAGTTCCCCTGACTCTCGGGCAGTGACATGTGGAATGGCGTCTCTGTCTGCAGAGA
AGGTCACACTGGACCAAAGGGACTATGAGAAGTATTCAGTGTCCTGCCAGGAGGATGTCA
CCTGCCCAACTGCCGAGGAGACCCTGCCCATTGAACTGGCGTTGGAAGCACGGCAGCAGA
ATAAATATGAGAACTACAGCACCAGCTTCTTCATCAGGGACATCATCAAACCAGACCCGC
CCAAGAACTTGCAGATGAAGCCTTTGAAGAACTCACAGGTGGAGGTCAGCTGGGAGTACC
CTGACTCCTGGAGCACTCCCCATTCCTACTTCTCCCTCAAGTTCTTTGTTCGAATCCAGC
GCAAGAAAGAAAAGATGAAGGAGACAGAGGAGGGGTGTAACCAGAAAGGTGCGTTCCTCG
TAGAGAAGACATCTACCGAAGTCCAATGCAAAGGCGGGAATGTCTGCGTGCAAGCTCAGG
ATCGGTATTACAATTCCTCATGCAGCAAGTGGGCATGTGTTCCCTGCAGGGTCCGATCCG
```

Figure 27 (part 2 of 16)

```
GTGGCGGTGGCTCGGGCGGTGGTGGGTCGGGTGGCGGCGGATCTAGGGTCATTCCAGTCT
CTGGACCTGCCAGGTGTCTTAGCCAGTCCCGAAACCTGCTGAAGACCACAGATGACATGG
TGAAGACGGCCAGAGAAAAACTGAAACATTATTCCTGCACTGCTGAAGACATCGATCATG
AAGACATCACACGGGACCAAACCAGCACATTGAAGACCTGTTTACCACTGGAACTACACA
AGAACGAGAGTTGCCTGGCTACTAGAGAGACTTCTTCCACAACAAGAGGGAGCTGCCTGC
CCGCACAGAAGACGTCTTTGATGATGACCCTGTGCCTTGGTAGCATCTATGAGGACTTGA
AGATGTACCAGACAGAGTTCCAGGCCATCAACGCAGCACTTCAGAATCACAACCATCAGC
AGATCATTCTAGACAAGGGCATGCTGGTGGCCATCGATGAGCTGATGCAGTCTCTGAATC
ATAATGGCGAGACTCTGCGCCAGAAACCTCCTGTGGGAGAAGCAGACCCTTACAGAGTGA
AAATGAAGCTCTGCATCCTGCTTCACGCCTTCAGCACCTGCGTCGTGACCATCAACAGGG
TGATGGGCTATCTGAGCTCCGCCTGAGAATTGATCCGGATTAGTCCAATTTGTTAAAGAC
AGGATGAAGCTTTTAAAACAGCTCTGGGGTTGTACCCACCCCAGAGGCCCACGTGGCGGC
TAGTACTCCGGTATTGCGGTACCCTTGTACGCCTGTTTTATAGTCCCTTCCCGTAACTTA
GACGCACAAAACCAAGTTCAATAGAAGGGGGTACAAACCAGTACCACCACGAACAAGCAC
TTCTGTTTCCCCGGTGATGTCGTATAGACTGCTTGCGTGGTTGAAAGCGACGGATCCGTT
ATCCGCTTATGTACTTCGAGAAGCCCAGTACCACCGTCGGAATCTTCGATGCGTTGCGCTC
AGCACTCAACCCCAGAGTGTAGCTTAGGCTGATGAGTCTGGACATCCCTCACCGGTGACG
GTGGTCCAGGCTGCGTTGGCGGCCTACCTATGGCTAACGCCATGGGACGCTAGTTGTGAA
CAAGGTGTGAAGAGCCTATTGAGCTACATAAGAATCCTCCGGCCCCTGAATGCGGCTAAT
CCCAACCTCGGAGCAGGTGGTCACAAACCAGTGATTGGCCTGTCGTAACGCGCAAGTCCG
TGGCGGAACCGACTACTTTGGGTGTCCGTGTTTCCTTTTATTTTATTGTGGCTGCTTATG
GTGACAATCACAGATTGTTATCATAAAGCGAATTGGATTGCGGCCGCATGATCGACCAGC
ACACACTTGATGTGGAGGATACCGCGGATGCCAGACATCCAGCAGGTACTTCGTGCCCCT
CGGATGCGGCGCTCCTCAGAGATACCGGGCTCCTCGCGGACGCTGCGCTCCTCTCAGATA
CTGTGCGCCCCACAAATGCCGCGCTCCCCACGGATGCTGCCTACCCTGCGGTTAATGTTC
GGGATCGCGAGGCCGCGTGGCCGCCTGCACTGAACTTCTGTTCCCGCCACCCAAAGCTCT
ATGGCCTAGTCGCTTTGGTTTTGCTGCTTCTGATCGCCGCCTGTGTTCCTATCTTCACCC
GCACCGAGCCTCGGCCAGCGCTCACAATCACCACCTCGCCCAACCTGGGTACCCGAGAGA
ATAATGCAGACCAGGTCACCCCTGTTTCCCACATTGGCTGCCCAACACTACACAACAGG
GCTCTCCTGTGTTCGCCAAGCTACTGGCTAAAAACCAAGCATCGTTGTGCAATACAACTC
TGAACTGGCACAGCCAAGATGGAGCTGGGAGCTCATACCTATCTCAAGGTCTGAGGTACG
AAGAAGACAAAAAGGAGTTGGTGGTAGACAGTCCCGGGCTCTACTACGTATTTTTGGAAC
TGAAGCTCAGTCCAACATTCACAAACACAGGCCACAAGGTGCAGGGCTGGGTCTCTCTTG
TTTTGCAAGCAAAGCCTCAGGTAGATGACTTTGACAACTTGGCCCTGACAGTGGAACTGT
TCCCTTGCTCCATGGAGAACAAGTTAGTGGACCGTTCCTGGAGTCAACTGTTGCTCCTGA
AGGCTGGCCACCGCCTCAGTGTGGGTCTGAGGGCTTATCTGCATGGAGCCCAGGATGCAT
ACAGAGACTGGCAGCTGTCTTATCCCAACACCACCAGCTTTGGACTCTTTCTTGTGAAAC
CCGACAACCCATGGGAATGAGAACTATCCTTCTTGTGACTGGCGCGCCTGATCAATCGAT
GTTTAAACGTTATTTTCCACCATATTGCCGTCTTTTGGCAATGTGAGGGCCCGGAAACCT
GGCCCTGTCTTCTTGACGAGCATTCCTAGGGGTCTTTCCCCTCTCGCCAAAGGAATGCAA
GGTCTGTTGAATGTCGTGAAGGAAGCAGTTCCTCTGGAAGCTTCTTGAAGACAAACAACG
TCTGTAGCGACCCTTTGCAGGCAGCGGAACCCCCCACCTGGCGACAGGTGCCTCTGCGGC
```

Figure 27 (part 3 of 16)

```
CAAAAGCCACGTGTATAAGATACACCTGCAAAGGCGGCACAACCCCAGTGCCACGTTGTG
AGTTGGATAGTTGTGGAAAGAGTCAAATGGCTCTCCTGAAGCGTATTCAACAAGGGGCTG
AAGGATGCCCAGAAGGTACCCCATTGTATGGGATCTGATCTGGGGCCTCGGTGCACATGC
TTTACGTGTGTTTAGTCGAGGTTAAAAAACGTCTAGGCCCCCTGAACCACGGGGACGTGG
TTTTCCTTTGAAAAACACGATTCTCGAGACTAGTGCCACCATGTACAGCATGCAGCTCGC
ATCCTGTGTCACATTGACACTTGTGCTCCTTGTCAACAGCGCACCCACTTCAAGCTCCAC
TTCAAGCTCTACAGCGGAAGCACAGCAGCAGCAGCAGCAGCAGCAGCAGCAGCAGCAGCA
CCTGGAGCAGCTGTTGATGGACCTACAGGAGCTCCTGAGCAGGATGGAGAATTACAGGAA
CCTGAAACTCCCCAGGATGCTCACCTTCAAATTTTACTTGCCCAAGCAGGCCACAGAATT
GAAAGATCTTCAGTGCCTAGAAGATGAACTTGGACCTCTGCGGCATGTTCTGGATTTGAC
TCAAAGCAAAAGCTTTCAATTGGAAGATGCTGAGAATTTCATCAGCAATATCAGAGTAAC
TGTTGTAAAACTAAAGGGCTCTGACAACACATTTGAGTGCCAATTCGATGATGAGTCAGC
AACTGTGGTGGACTTTCTGAGGAGATGGATAGCCTTCTGTCAAAGCATCATCTCAACAAG
CCCTCAATAACTATGTAACGCGTGCTAGCATGGCCGGCCGCGGCCGCGGCCGCTCGAGCC
TAAGCTTCTAGATAAGATATCCGATCCACCGGATCTAGATAACTGATCATAATCAGCCAT
ACCACATTTGTAGAGGTTTTACTTGCTTTAAAAAACCTCCCACACCTCCCCCTGAACCTG
AAACATAAAATGAATGCAATTGTTGTTGTTAACTTGTTTATTGCAGCTTATAATGGTTAC
AAATAAAGCAATAGCATCACAAATTTCACAAATAAAGCATTTTTTTCACTGCATTCTAGT
TGTGGTTTGTCCAAACTCATCAATGTATCTTAACGCNNNNNTAAGGGTGGGAAAGAATATA
TAAGGTGGGGGTCTTATGTAGTTTTGTATCTGTTTTGCAGCAGCCGCCGCCGCCATGAGC
ACCAACTCGTTTGATGGAAGCATTGTGAGCTCATATTTGACAACGCGCATGCCCCCATGG
GCCGGGGTGCGTCAGAATGTGATGGGCTCCAGCATTGATGGTCGCCCCGTCCTGCCCGCA
AACTCTACTACCTTGACCTACGAGACCGTGTCTGGAACGCCGTTGGAGACTGCAGCCTCC
GCCGCCGCTTCAGCCGCTGCAGCCACCGCCCGCGGGATTGTGACTGACTTTGCTTTCCTG
AGCCCGCTTGCAAGCAGTGCAGCTTCCCGTTCATCCGCCCGCGATGACAAGTTGACGGCT
CTTTTGGCACAATTGGATTCTTTGACCCGGGAACTTAATGTCGTTTCTCAGCAGCTGTTG
GATCTGCGCCAGCAGGTTTCTGCCCTGAAGGCTTCCTCCCCTCCAATGCGGTTTAAAAC
ATAAATAAAAACCAGACTCTGTTTGGATTTGGATCAAGCAAGTGTCTTGCTGTCTTTAT
TTAGGGGTTTTGCGCGCGCGGTAGGCCCGGGACCAGCGGTCTCGGTCGTTGAGGGTCCTG
TGTATTTTTTCCAGGACGTGGTAAAGGTGACTCTGGATGTTCAGATACATGGGCATAAGC
CCGTCTCTGGGGTGGAGGTAGCACCACTGCAGAGCTTCATGCTGCGGGTGGTGTTGTAG
ATGATCCAGTCGTAGCAGGAGCGCTGGGCGTGGTGCCTAAAAATGTCTTTCAGTAGCAAG
CTGATTGCCAGGGGCAGGCCCTTGGTGTAAGTGTTTACAAAGCGGTTAAGCTGGGATGGG
TGCATACGTGGGGATATGAGATGCATCTTGGACTGTATTTTTAGGTTGGCTATGTTCCCA
GCCATATCCCTCCGGGGATTCATGTTGTGCAGAACCACCAGCACAGTGTATCCGGTGCAC
TTGGGAAATTTGTCATGTAGCTTAGAAGGAAATGCGTGGAAGAACTTGGAGACGCCCTTG
TGACCTCCAAGATTTTCCATGCATTCGTCCATAATGATGGCAATGGGCCCACGGGCGGCG
GCCTGGGCGAAGATATTTCTGGGATCACTAACGTCATAGTTGTGTTCCAGGATGAGATCG
TCATAGGCCATTTTTACAAAGCGCGGGCGGAGGGTGCCAGACTGCGGTATAATGGTTCCA
TCCGGCCCAGGGGCGTAGTTACCCTCACAGATTTGCATTTCCCACGCTTTGAGTTCAGAT
GGGGGGATCATGTCTACCTGCGGGGCGATGAAGAAAACGGTTTCCGGGGTAGGGGAGATC
AGCTGGGAAGAAAGCAGGTTCCTGAGCAGCTGCGACTTACCGCAGCCGGTGGGCCCGTAA
```

Figure 27 (part 4 of 16)

```
ATCACACCTATTACCGGGTGCAACTGGTAGTTAAGAGAGCTGCAGCTGCCGTCATCCCTG
AGCAGGGGGGCCACTTCGTTAAGCATGTCCCTGACTCGCATGTTTTCCCTGACCAAATCC
GCCAGAAGGCGCTCGCCGCCCAGCGATAGCAGTTCTTGCAAGGAAGCAAAGTTTTTCAAC
GGTTTGAGACCGTCCGCCGTAGGCATGCTTTTGAGCGTTTGACCAAGCAGTTCCAGGCGG
TCCCACAGCTCGGTCACCTGCTCTACGGCATCTCGATCCAGCATATCTCCTCGTTTCGCG
GGTTGGGGCGGCTTTCGCTGTACGGCAGTAGTCGGTGCTCGTCCAGACGGGCCAGGGTCA
TGTCTTTCCACGGGCGCAGGGTCCTCGTCAGCGTAGTCTGGGTCACGGTGAAGGGGTGCG
CTCCGGGCTGCGCGCTGGCCAGGGTGCGCTTGAGGCTGGTCCTGCTGGTGCTGAAGCGCT
GCCGGTCTTCGCCCTGCGCGTCGGCCAGGTAGCATTTGACCATGGTGTCATAGTCCAGCC
CCTCCGCGGCGTGGCCCTTGGCGCGCAGCTTGCCCTTGGAGGAGGCGCCGCACGAGGGC
AGTGCAGACTTTTGAGGGCGTAGAGCTTGGGCGCGAGAAATACCGATTCCGGGGAGTAGG
CATCCGCGCCGCAGGCCCCGCAGACGGTCTCGCATTCCACGAGCCAGGTGAGCTCTGGCC
GTTCGGGGTCAAAAACCAGGTTTCCCCCATGCTTTTTGATGCGTTTCTTACCTCTGGTTT
CCATGAGCCGGTGTCCACGCTCGGTGACGAAAAGGCTGTCCGTGTCCCCGTATACAGACT
TGAGAGGCCTGTCCTCGAGCGGTGTTCCGCGGTCCTCCTCGTATAGAAACTCGGACCACT
CTGAGACAAAGGCTCGCGTCCAGGCCAGCACGAAGGAGGCTAAGTGGGAGGGGTAGCGGT
CGTTGTCCACTAGGGGGTCCACTCGCTCCAGGGTGTGAAGACACATGTCGCCCTCTTCGG
CATCAAGGAAGGTGATTGGTTTGTAGGTGTAGGCCACGTGACCGGGTGTTCCTGAAGGGG
GGCTATAAAAGGGGGTGGGGGCGCGTTCGTCCTCACTCTCTTCCGCATCGCTGTCTGCGA
GGGCCAGCTGTTGGGGTGAGTACTCCCTCTGAAAAGCGGGCATGACTTCTGCGCTAAGAT
TGTCAGTTTCCAAAAACGAGGAGGATTTGATATTCACCTGGCCCGCGGTGATGCCTTTGA
GGGTGGCCGCATCCATCTGGTCAGAAAAGACAATCTTTTTGTTGTCAAGCTTGGTGGCAA
ACGACCCGTAGAGGGCGTTGGACAGCAACTTGGCGATGGAGCGCAGGGTTTGGTTTTTGT
CGCGATCGGCGCGCTCCTTGGCCGCGATGTTTAGCTGCACGTATTCGCGCGCAACGCACC
GCCATTCGGGAAAGACGGTGGTGCGCTCGTCGGGCACCAGGTGCACGCGCCAACCGCGGT
TGTGCAGGGTGACAAGGTCAACGCTGGTGGCTACCTCTCCGCGTAGGCGCTCGTTGGTCC
AGCAGAGGCGGCCGCCCTTGCGCGAGCAGAATGGCGGTAGGGGGTCTAGCTGCGTCTCGT
CCGGGGGGTCTGCGTCCACGGTAAAGACCCCGGGCAGCAGGCGCGCGTCGAAGTAGTCTA
TCTTGCATCCTTGCAAGTCTAGCGCCTGCTGCCATGCGCGGGCGGCAAGCGCGCGCTCGT
ATGGGTTGAGTGGGGGACCCCATGGCATGGGGTGGGTGAGCGCGGAGGCGTACATGCCGC
AAATGTCGTAAACGTAGAGGGGCTCTCTGAGTATTCCAAGATATGTAGGGTAGCATCTTC
CACCGCGGATGCTGGCGCGCACGTAATCGTATAGTTCGTGCGAGGGAGCGAGGAGGTCGG
GACCGAGGTTGCTACGGGCGGGCTGCTCTGCTCGGAAGACTATCTGCCTGAAGATGGCAT
GTGAGTTGGATGATATGGTTGGACGCTGGAAGACGTTGAAGCTGGCGTCTGTGAGACCTA
CCGCGTCACGCACGAAGGAGGCGTAGGAGTCGCGCAGCTTGTTGACCAGCTCGGCGGTGA
CCTGCACGTCTAGGGCGCAGTAGTCCAGGGTTTCCTTGATGATGTCATACTTATCCTGTC
CCTTTTTTTTCCACAGCTCGCGGTTGAGGACAAACTCTTCGCGGTCTTTCCAGTACTCTT
GGATCGGAAACCCGTCGGCCTCCGAACGGTAAGAGCCTAGCATGTAGAACTGGTTGACGG
CCTGGTAGGCGCAGCATCCCTTTTCTACGGGTAGCGCGTATGCCTGCGCGGCCTTCCGGA
GCGAGGTGTGGGTGAGCGCAAAGGTGTCCCTGACCATGACTTTGAGGTACTGGTATTTGA
AGTCAGTGTCGTCGCATCCGCCCTGCTCCCAGAGCAAAAAGTCCGTGCGCTTTTTGGAAC
GCGGATTTGGCAGGGCGAAGGTGACATCGTTGAAGAGTATCTTTCCCGCGCGAGGCATAA
```

Figure 27 (part 5 of 16)

```
AGTTGCGTGTGATGCGGAAGGGTCCCGGCACCTCGGAACGGTTGTTAATTACCTGGGCGG
CGAGCACGATCTCGTCAAAGCCGTTGATGTTGTGGCCCACAATGTAAAGTTCCAAGAAGC
GCGGGATGCCCTTGATGGAAGGCAATTTTTTAAGTTCCTCGTAGGTGAGCTCTTCAGGGG
AGCTGAGCCCGTGCTCTGAAAGGGCCCAGTCTGCAAGATGAGGGTTGGAAGCGACGAATG
AGCTCCACAGGTCACGGGCCATTAGCATTTGCAGGTGGTCGCGAAAGGTCCTAAACTGGC
GACCTATGGCCATTTTTTCTGGGGTGATGCAGTAGAAGGTAAGCGGGTCTTGTTCCCAGC
GGTCCCATCCAAGGTTCGCGGCTAGGTCTCGCGCGGCAGTCACTAGAGGCTCATCTCCGC
CGAACTTCATGACCAGCATGAAGGGCACGAGCTGCTTCCCAAAGGCCCCCATCCAAGTAT
AGGTCTCTACATCGTAGGTGACAAAGAGACGCTCGGTGCGAGGATGCGAGCCGATCGGGA
AGAACTGGATCTCCCGCCACCAATTGGAGGAGTGGCTATTGATGTGGTGAAAGTAGAAGT
CCCTGCGACGGGCCGAACACTCGTGCTGGCTTTTGTAAAAACGTGCGCAGTACTGGCAGC
GGTGCACGGGCTGTACATCCTGCACGAGGTTGACCTGACGACCGCGCACAAGGAAGCAGA
GTGGGAATTTGAGCCCCTCGCCTGGCGGGTTTGGCTGGTGGTCTTCTACTTCGGCTGCTT
GTCCTTGACCGTCTGGCTGCTCGAGGGGAGTTACGGTGGATCGGACCACCACGCCGCGCG
AGCCAAAGTCCAGATGTCCGCGCGCGGCGGTCGGAGCTTGATGACAACATCGCGCAGAT
GGGAGCTGTCCATGGTCTGGAGCTCCCGCGGCGTCAGGTCAGGCGGGAGCTCCTGCAGGT
TTACCTCGCATAGACGGGTCAGGGCGCGGGCTAGATCCAGGTGATACCTAATTTCCAGGG
GCTGGTTGGTGGCGGCGTCGATGGCTTGCAAGAGGCCGCATCCCCGCGGCGCGACTACGG
TACCGCGCGGCGGGCGGTGGGCCGCGGGGTGTCCTTGGATGATGCATCTAAAAGCGGTG
ACGCGGGCGAGCCCCGGAGGTAGGGGGGCTCCGGACCCGCCGGGAGAGGGGCAGGGG
CACGTCGGCGCCGCGCGCGGGCAGGAGCTGGTGCTGCGCGCGTAGGTTGCTGGCGAACGC
GACGACGCGGCGGTTGATCTCCTGAATCTGGCGCCTCTGCGTGAAGACGACGGGCCCGGT
GAGCTTGAGCCTGAAAGAGAGTTCGACAGAATCAATTTCGGTGTCGTTGACGGCGGCCTG
GCGCAAAATCTCCTGCACGTCTCCTGAGTTGTCTTGATAGGCGATCTCGGCCATGAACTG
CTCGATCTCTTCCTCCTGGAGATCTCCGCGTCCGGCTCGCTCCACGGTGGCGGCGAGGTC
GTTGGAAATGCGGGCCATGAGCTGCGAGAAGGCGTTGAGGCCTCCCTCGTTCCAGACGCG
GCTGTAGACCACGCCCCCTTCGGCATCGCGGGCGCGCATGACCACCTGCGCGAGATTGAG
CTCCACGTGCCGGGCGAAGACGGCGTAGTTTCGCAGGCGCTGAAAGAGGTAGTTGAGGGT
GGTGGCGGTGTGTTCTGCCACGAAGAAGTACATAACCCAGCGTCGCAACGTGGATTCGTT
GATATCCCCCAAGGCCTCAAGGCGCTCCATGGCCTCGTAGAAGTCCACGGCGAAGTTGAA
AAACTGGGAGTTGCGCGCCGACACGGTTAACTCCTCCTCCAGAAGACGGATGAGCTCGGC
GACAGTGTCGCGCACCTCGCGCTCAAAGGCTACAGGGGCCTCTTCTTCTTCTTCAATCTC
CTCTTCCATAAGGGCCTCCCCTTCTTCTTCTTCTGGCGGCGGTGGGGGAGGGGGACACG
GCGGCGACGACGGCGCACCGGAGGCGGTCGACAAAGCGCTCGATCATCTCCCCGCGGCG
ACGGCGCATGGTCTCGGTGACGGCGCGGCCGTTCTCGCGGGGGCGCAGTTGGAAGACGCC
GCCCGTCATGTCCCGGTTATGGGTTGGCGGGGGGCTGCCATGCGGCAGGGATACGGCGCT
AACGATGCATCTCAACAATTGTTGTGTAGGTACTCCGCCGCCGAGGGACCTGAGCGAGTC
CGCATCGACCGGATCGGAAAACCTCTCGAGAAAGGCGTCTAACCAGTCACAGTCGCAAGG
TAGGCTGAGCACCGTGGCGGGCGGCAGCGGGCGGCGGTCGGGGTTGTTTCTGGCGGAGGT
GCTGCTGATGATGTAATTAAAGTAGGCGGTCTTGAGACGGCGGATGGTCGACAGAAGCAC
CATGTCCTTGGGTCCGGCCTGCTGAATGCGCAGGCGGTCGGCCATGCCCCAGGCTTCGTT
TTGACATCGGCGCAGGTCTTTGTAGTAGTCTTGCATGAGCCTTTCTACCGGCACTTCTTC
```

Figure 27 (part 6 of 16)

```
TTCTCCTTCCTCTTGTCCTGCATCTCTTGCATCTATCGCTGCGGCGGCGGCGGAGTTTGG
CCGTAGGTGGCGCCCTCTTCCTCCCATGCGTGTGACCCCGAAGCCCCTCATCGGCTGAAG
CAGGGCTAGGTCGGCGACAACGCGCTCGGCTAATATGGCCTGCTGCACCTGCGTGAGGGT
AGACTGGAAGTCATCCATGTCCACAAAGCGGTGGTATGCGGCCGTGTTGATGGTGTAAGT
GCAGTTGGCCATAACGGACCAGTTAACGGTCTGGTGACCCGGCTGCGAGAGCTCGGTGTA
CCTGAGACGCGAGTAAGCCCTCGAGTCAAATACGTAGTCGTTGCAAGTCCGCACCAGGTA
CTGGTATCCCACCAAAAAGTGCGGCGGCGGCTGGCGGTAGAGGGGCCAGCGTAGGGTGGC
CGGGGCTCCGGGGCGAGATCTTCCAACATAAGGCGATGATATCCGTAGATGTACCTGGA
CATCCAGGTGATGCCGGCGGCGGTGGTGGAGGCGCGCGGAAAGTCGCGGACGCGGTTCCA
GATGTTGCGCAGCGGCAAAAAGTGCTCCATGGTCGGGACGCTCTGGCCGGTCAGGCGCGC
GCAATCGTTGACGCTCTACCGTGCAAAAGGAGAGCCTGTAAGCGGGCACTCTTCCGTGGT
CTGGTGGATAAATTCGCAAGGGTATCATGGCGGACGACCGGGGTTCGAGCCCCGTATCCG
GCCGTCCGCCGTGATCCATGCGGTTACCGCCCGCGTGTCGAACCCAGGTGTGCGACGTCA
GACAACGGGGAGTGCTCCTTTTGGCTTCCTTCCAGGCGCGGCGGCTGCTGCGCTAGCTT
TTTTGGCCACTGGCCGCGCGCAGCGTAAGCGGTTAGGCTGGAAAGCGAAAGCATTAAGTG
GCTCGCTCCCTGTAGCCGGAGGGTTATTTTCCAAGGGTTGAGTCGCGGGACCCCCGGTTC
GAGTCTCGGACCGGCCGGACTGCGGCGAACGGGGGTTTGCCTCCCCGTCATGCAAGACCC
CGCTTGCAAATTCCTCCGGAAACAGGGACGAGCCCCTTTTTTGCTTTTCCCAGATGCATC
CGGTGCTGCGGCAGATGCGCCCCCCTCCTCAGCAGCGGCAAGAGCAAGAGCAGCGGCAGA
CATGCAGGGCACCCTCCCCTCCTCCTACCGCGTCAGGAGGGGCGACATCCGCGGTTGACG
CGGCAGCAGATGGTGATTACGAACCCCGCGGCGCCGGGCCCGGCACTACCTGGACTTGG
AGGAGGGCGAGGGCCTGGCGCGGCTAGGAGCGCCCTCTCCTGAGCGGTACCCAAGGGTGC
AGCTGAAGCGTGATACGCGTGAGGCGTACGTGCCGCGGCAGAACCTGTTTCGCGACCGCG
AGGGAGAGGAGCCCGAGGAGATGCGGGATCGAAAGTTCCACGCAGGGCGCGAGCTGCGGC
ATGGCCTGAATCGCGAGCGGTTGCTGCGCGAGGAGGACTTTGAGCCCGACGCGCGAACCG
GGATTAGTCCCGCGCGCGCACACGTGGCGGCCGCCGACCTGGTAACCGCATACGAGCAGA
CGGTGAACCAGGAGATTAACTTTCAAAAAAGCTTTAACAACCACGTGCGTACGCTTGTGG
CGCGCGAGGAGGTGGCTATAGGACTGATGCATCTGTGGGACTTTGTAAGCGCGCTGGAGC
AAAACCCAAATAGCAAGCCGCTCATGGCGCAGCTGTTCCTTATAGTGCAGCACAGCAGGG
ACAACGAGGCATTCAGGGATGCGCTGCTAAACATAGTAGAGCCCGAGGGCCGCTGGCTGC
TCGATTTGATAAACATCCTGCAGAGCATAGTGGTGCAGGAGCGCAGCTTGAGCCTGGCTG
ACAAGGTGGCCGCCATCAACTATTCCATGCTTAGCCTGGGCAAGTTTTACGCCCGCAAGA
TATACCATACCCCTTACGTTCCCATAGACAAGGAGGTAAAGATCGAGGGGTTCTACATGC
GCATGGCGCTGAAGGTGCTTACCTTGAGCGACGACCTGGGCGTTTATCGCAACGAGCGCA
TCCACAAGGCCGTGAGCGTGAGCCGGCGGCGCGAGCTCAGCGACCGCGAGCTGATGCACA
GCCTGCAAAGGGCCCTGGCTGGCACGGGCAGCGGCGATAGAGAGGCCGAGTCCTACTTTG
ACGCGGGCGCTGACCTGCGCTGGGCCCAAGCCGACGCGCCCTGGAGGCAGCTGGGGCCG
GACCTGGGCTGGCGGTGGCACCCGCGCGCGCTGGCAACGTCGGCGGCGTGGAGGAATATG
ACGAGGACGATGAGTACGAGCCAGAGGACGGCGAGTACTAAGCGGTGATGTTTCTGATCA
GATGATGCAAGACGCAACGGACCCGGCGGTGCGGGCGGCGCTGCAGAGCCAGCCGTCCGG
CCTTAACTCCACGGACGACTGGCGCCAGGTCATGGACCGCATCATGTCGCTGACTGCGCG
CAATCCTGACGCGTTCCGGCAGCAGCCGCAGGCCAACCGGCTCTCCGCAATTCTGGAAGC
```

Figure 27 (part 7 of 16)

```
GGTGGTCCCGGCGCGCGCAAACCCCACGCACGAGAAGGTGCTGGCGATCGTAAACGCGCT
GGCCGAAAACAGGGCCATCCGGCCCGACGAGGCCGGCCTGGTCTACGACGCGCTGCTTCA
GCGCGTGGCTCGTTACAACAGCGGCAACGTGCAGACCAACCTGGACCGGCTGGTGGGGGA
TGTGCGCGAGGCCGTGGCGCAGCGTGAGCGCGCGCAGCAGCAGGGCAACCTGGGCTCCAT
GGTTGCACTAAACGCCTTCCTGAGTACACAGCCCGCCAACGTGCCGCGGGGACAGGAGGA
CTACACCAACTTTGTGAGCGCACTGCGGCTAATGGTGACTGAGACACCGCAAAGTGAGGT
GTACCAGTCTGGGCCAGACTATTTTTTCCAGACCAGTAGACAAGGCCTGCAGACCGTAAA
CCTGAGCCAGGCTTTCAAAAACTTGCAGGGGCTGTGGGGGTGCGGGCTCCCACAGGCGA
CCGCGCGACCGTGTCTAGCTTGCTGACGCCCAACTCGCGCCTGTTGCTGCTGCTAATAGC
GCCCTTCACGGACAGTGGCAGCGTGTCCCGGGACACATACCTAGGTCACTTGCTGACACT
GTACCGCGAGGCCATAGGTCAGGCGCATGTGGACGAGCATACTTTCCAGGAGATTACAAG
TGTCAGCCGCGCGCTGGGGCAGGAGGACACGGGCAGCCTGGAGGCAACCCTAAACTACCT
GCTGACCAACCGGCGGCAGAAGATCCCCTCGTTGCACAGTTTAAACAGCGAGGAGGAGCG
CATTTTGCGCTACGTGCAGCAGAGCGTGAGCCTTAACCTGATGCGCGACGGGGTAACGCC
CAGCGTGGCGCTGGACATGACCGCGCGCAACATGGAACCGGGCATGTATGCCTCAAACCG
GCCGTTTATCAACCGCCTAATGGACTACTTGCATCGCGCGGCCGCCGTGAACCCCGAGTA
TTTCACCAATGCCATCTTGAACCCGCACTGGCTACCGCCCCCTGGTTTCTACACCGGGGG
ATTCGAGGTGCCCGAGGGTAACGATGGATTCCTCTGGGACGACATAGACGACAGCGTGTT
TTCCCCGCAACCGCAGACCCTGCTAGAGTTGCAACAGCGCGAGCAGGCAGAGGCGGCGCT
GCGAAAGGAAAGCTTCCGCAGGCCAAGCAGCTTGTCCGATCTAGGCGCTGCGGCCCCGCG
GTCAGATGCTAGTAGCCCATTTCCAAGCTTGATAGGGTCTCTTACCAGCACTCGCACCAC
CCGCCCGCGCCTGCTGGGCGAGGAGGAGTACCTAAACAACTCGCTGCTGCAGCCGCAGCG
CGAAAAAAACCTGCCTCCGGCATTTCCCAACAACGGGATAGAGAGCCTAGTGGACAAGAT
GAGTAGATGGAAGACGTACGCGCAGGAGCACAGGGACGTGCCAGGCCCGCGCCCGCCCAC
CCGTCGTCAAAGGCACGACCGTCAGCGGGGTCTGGTGTGGGAGGACGATGACTCGGCAGA
CGACAGCAGCGTCCTGGATTTGGGAGGGAGTGGCAACCCGTTTGCGCACCTTCGCCCCAG
GCTGGGGAGAATGTTTTAAAAAAAAAAAAGCATGATGCAAAATAAAAAACTCACCAAGGC
CATGGCACCGAGCGTTGGTTTTCTTGTATTCCCCTTAGTATGCGGCGCGCGGCGATGTAT
GAGGAAGGTCCTCCTCCCTCCTACGAGAGTGTGGTGAGCGCGGCGCCAGTGGCGGCGGCG
CTGGGTTCTCCCTTCGATGCTCCCCTGGACCCGCCGTTTGTGCCTCCGCGGTACCTGCGG
CCTACCGGGGGGAGAAACAGCATCCGTTACTCTGAGTTGGCACCCCTATTCGACACCACC
CGTGTGTACCTGGTGGACAACAAGTCAACGGATGTGGCATCCCTGAACTACCAGAACGAC
CACAGCAACTTTCTGACCACGGTCATTCAAAACAATGACTACAGCCCGGGGGAGGCAAGC
ACACAGACCATCAATCTTGACGACCGGTCGCACTGGGGCGGCGACCTGAAAACCATCCTG
CATACCAACATGCCAAATGTGAACGAGTTCATGTTTACCAATAAGTTTAAGGCGCGGGTG
ATGGTGTCGCGCTTGCCTACTAAGGACAATCAGGTGGAGCTGAAATACGAGTGGGTGGAG
TTCACGCTGCCCGAGGGCAACTACTCCGAGACCATGACCATAGCCTTATGAACAACGCG
ATCGTGGAGCACTACTTGAAAGTGGGCAGACAGAACGGGGTTCTGGAAAGCGACATCGGG
GTAAAGTTTGACACCCGCAACTTCAGACTGGGGTTTGACCCCGTCACTGGTCTTGTCATG
CCTGGGGTATATACAAACGAAGCCTTCCATCCAGACATCATTTTGCTGCCAGGATGCGGG
GTGGACTTCACCCACAGCCGCCTGAGCAACTTGTTGGGCATCCGCAAGCGGCAACCCTTC
CAGGAGGGCTTTAGGATCACCTACGATGATCTGGAGGGTGGTAACATTCCCGCACTGTTG
```

Figure 27 (part 8 of 16)

```
GATGTGGACGCCTACCAGGCGAGCTTGAAAGATGACACCGAACAGGGCGGGGGTGGCGCA
GGCGGCAGCAACAGCAGTGGCAGCGGCGCGGAAGAGAACTCCAACGCGGCAGCCGCGGCA
ATGCAGCCGGTGGAGGACATGAACGATCATGCCATTCGCGGCGACACCTTTGCCACACGG
GCTGAGGAGAAGCGCGCTGAGGCCGAAGCAGCGGCCGAAGCTGCCGCCCCGCTGCGCAA
CCCGAGGTCGAGAAGCCTCAGAAGAAACCGGTGATCAAACCCCTGACAGAGGACAGCAAG
AAACGCAGTTACAACCTAATAAGCAATGACAGCACCTTCACCCAGTACCGCAGCTGGTAC
CTTGCATACAACTACGGCGACCCTCAGACCGGAATCCGCTCATGGACCCTGCTTTGCACT
CCTGACGTAACCTGCGGCTCGGAGCAGGTCTACTGGTCGTTGCCAGACATGATGCAAGAC
CCCGTGACCTTCCGCTCCACGCGCCAGATCAGCAACTTTCCGGTGGTGGGCGCCGAGCTG
TTGCCCGTGCACTCCAAGAGCTTCTACAACGACCAGGCCGTCTACTCCCAACTCATCCGC
CAGTTTACCTCTCTGACCCACGTGTTCAATCGCTTTCCGAGAACCAGATTTTGGCGCGC
CCGCCAGCCCCCACCATCACCACCGTCAGTGAAAACGTTCCTGCTCTCACAGATCACGGG
ACGCTACCGCTGCGCAACAGCATCGGAGGAGTCCAGCGAGTGACCATTACTGACGCCAGA
CGCCGCACCTGCCCCTACGTTTACAAGGCCCTGGGCATAGTCTCGCCGCGCGTCCTATCG
AGCCGCACTTTTTGAGCAAGCATGTCCATCCTTATATCGCCAGCAATAACACAGGCTGG
GGCCTGCGCTTCCCAAGCAAGATGTTTGGCGGGGCCAAGAAGCGCTCCGACCAACACCCA
GTGCGCGTGCGCGGGCACTACCGCGCGCCCTGGGGCGCGCACAAACGCGGCCGCACTGGG
CGCACCACCGTCGATGACGCCATCGACGCGGTGGTGGAGGAGGCCGCAACTACACGCCC
ACGCCGCCACCAGTGTCCACAGTGGACGCGGCCATTCAGACCGTGGTGCGCGGAGCCCGG
CGCTATGCTAAAATGAAGAGACGGCGGAGGCGCGTAGCACGTCGCCACCGCCGCCGACCC
GGCACTGCCGCCCAACGCGCGGCGGCGGCCCTGCTTAACCGCGCACGTCGCACCGGCCGA
CGGGCGGCCATGCGGGCCGCTCGAAGGCTGGCCGCGGGTATTGTCACTGTGCCCCCCAGG
TCCAGGCGACGAGCGGCCGCCGCAGCAGCCGCGGCCATTAGTGCTATGACTCAGGGTCGC
AGGGGCAACGTGTATTGGGTGCGCGACTCGGTTAGCGGCCTGCGCGTGCCCGTGCGCACC
CGCCCCCGCGCAACTAGATTGCAAGAAAAAACTACTTAGACTCGTACTGTTGTATGTAT
CCAGCGGCGGCGGCGCGCAACGAAGCTATGTCCAAGCGCAAAATCAAAGAAGAGATGCTC
CAGGTCATCGCGCCGGAGATCTATGGCCCCCCGAAGAAGGAAGAGCAGGATTACAAGCCC
CGAAAGCTAAAGCGGGTCAAAAAGAAAAAGAAAGATGATGATGATGAACTTGACGACGAG
GTGGAACTGCTGCACGCTACCGCGCCCAGGCGACGGGTACAGTGGAAAGGTCGACGCGTA
AAACGTGTTTTGCGACCCGGCACCACCGTAGTCTTTACGCCGGTGAGCGCTCCACCCGC
ACCTACAAGCGCGTGTATGATGAGGTGTACGGCGACGAGGACCTGCTTGAGCAGGCCAAC
GAGCGCCTCGGGGAGTTTGCCTACGAAAGCGGCATAAGGACATGCTGGCGTTGCCGCTG
GACGAGGGCAACCCAACACCTAGCCTAAAGCCCGTAACACTGCAGCAGGTGCTGCCCGCG
CTTGCACCGTCCGAAGAAAAGCGCGGCCTAAAGCGCGAGTCTGGTGACTTGGCACCCACC
GTGCAGCTGATGGTACCCAAGCGCCAGCGACTGGAAGATGTCTTGGAAAAAATGACCGTG
GAACCTGGGCTGGAGCCCGAGGTCCGCGTGCGGCCAATCAAGCAGGTGGCGCCGGGACTG
GGCGTGCAGACCGTGGACGTTCAGATACCCACTACCAGTAGCACCAGTATTGCCACCGCC
ACAGAGGGCATGGAGACACAAACGTCCCCGGTTGCCTCAGCGGTGGCGGATGCCGCGGTG
CAGGCGGTCGCTGCGGCCGCGTCCAAGACCTCTACGGAGGTGCAAACGGACCCGTGGATG
TTTCGCGTTTCAGCCCCCGGCGCCCGCGCGGTTCGAGGAAGTACGGCGCCGCCAGCGCG
CTACTGCCCGAATATGCCCTACATCCTTCCATTGCGCCTACCCCGGCTATCGTGGCTAC
ACCTACCGCCCCAGAAGACGAGCAACTACCCGACGCCGAACCACCACTGGAACCCGCCGC
```

Figure 27 (part 9 of 16)

```
CGCCGTCGCCGTCGCCAGCCGTGCTGGCCCCGATTTCCGTGCGCAGGGTGGCTCGCGAA
GGAGGCAGGACCCTGGTGCTGCCAACAGCGCGCTACCACCCCAGCATCGTTTAAAAGCCG
GTCTTTGTGGTTCTTGCAGATATGGCCCTCACCTGCCGCCTCCGTTTCCCGGTGCCGGGA
TTCCGAGGAAGAATGCACCGTAGGAGGGGCATGGCCGGCCACGGCCTGACGGGCGGCATG
CGTCGTGCGCACCACCGGCGGCGGCGCGCGTCGCACCGTCGCATGCGCGGCGGTATCCTG
CCCCTCCTTATTCCACTGATCGCCGCGGCGATTGGCGCCGTGCCCGGAATTGCATCCGTG
GCCTTGCAGGCGCAGAGACACTGATTAAAAACAAGTTGCATGTGGAAAAATCAAAATAAA
AAGTCTGGACTCTCACGCTCGCTTGGTCCTGTAACTATTTTGTAGAATGGAAGACATCAA
CTTTGCGTCTCTGGCCCCGCGACACGGCTCGCGCCCGTTCATGGGAAACTGGCAAGATAT
CGGCACCAGCAATATGAGCGGTGGCGCCTTCAGCTGGGGCTCGCTGTGGAGCGGCATTAA
AAATTTCGGTTCCACCGTTAAGAACTATGGCAGCAAGGCCTGGAACAGCAGCACAGGCCA
GATGCTGAGGGATAAGTTGAAAGAGCAAAATTTCCAACAAAAGGTGGTAGATGGCCTGGC
CTCTGGCATTAGCGGGGTGGTGGACCTGGCCAACCAGGCAGTGCAAAATAAGATTAACAG
TAAGCTTGATCCCCGCCCTCCCGTAGAGGAGCCTCCACCGGCCGTGGAGACAGTGTCTCC
AGAGGGGCGTGGCGAAAAGCGTCCGCGCCCCGACAGGGAAGAAACTCTGGTGACGCAAAT
AGACGAGCCTCCCTCGTACGAGGAGGCACTAAAGCAAGGCCTGCCCACCACCCGTCCCAT
CGCGCGCATGGCTACCGGAGTGCTGGCCAGCACACACCCGTAACGCTGGACCTGCCTCC
CCCCGCCGACACCCAGCAGAAACCTGTGCTGCCAGGCCCGACCGCCGTTGTTGTAACCCG
TCCTAGCCGCGCGTCCCTGCGCCGCGCCGCCAGCGGTCCGCGATCGTTGCGGCCCGTAGC
CAGTGGCAACTGGCAAAGCACACTGAACAGCATCGTGGGTCTGGGGGTGCAATCCCTGAA
GCGCCGACGATGCTTCTGAATAGCTAACGTGTCGTATGTGTGTCATGTATGCGTCCATGT
CGCCGCCAGAGGAGCTGCTGAGCCGCCGCGCGCCCGCTTTCCAAGATGGCTACCCCTTCG
ATGATGCCGCAGTGGTCTTACATGCACATCTCGGGCCAGGACGCCTCGGAGTACCTGAGC
CCCGGGCTGGTGCAGTTTGCCCGCGCCACCGAGACGTACTTCAGCCTGAATAACAAGTTT
AGAAACCCGACGGTGGCGCCTACGCACGACGTGACCACAGACCGGTCCCAGCGTTTGACG
CTGCGGTTCATCCCTGTGGACCGTGAGGATACTGCGTACTCGTACAAGGCGCGGTTCACC
CTAGCTGTGGGTGATAACCGTGTGCTGGACATGGCTTCCACGTACTTTGACATCCGCGGC
GTGCTGGACAGGGGCCCTACTTTTAAGCCCTACTCTGGCACTGCCTACAACGCCCTGGCT
CCCAAGGGTGCCCCAAATCCTTGCGAATGGGATGAAGCTGCTACTGCTCTTGAAATAAAC
CTAGAAGAAGAGGACGATGACAACGAAGACGAAGTAGACGAGCAAGCTGAGCAGCAAAAA
ACTCACGTATTTGGGCAGGCGCCTTATTCTGGTATAAATATTACAAAGGAGGGTATTCAA
ATAGGTGTCGAAGGTCAAACACCTAAATATGCCGATAAAACATTTCAACCTGAACCTCAA
ATAGGAGAATCTCAGTGGTACGAAACTGAAATTAATCATGCAGCTGGGAGAGTCCTTAAA
AAGACTACCCCAATGAAACCATGTTACGGTTCATATGCAAAACCCACAAATGAAAATGGA
GGGCAAGGCATTCTTGTAAAGCAACAAAATGGAAAGCTAGAAAGTCAAGTGGAAATGCAA
TTTTTCTCAACTACTGAGGCGACCGCAGGCAATGGTGATAACTTGACTCCTAAAGTGGTA
TTGTACAGTGAAGATGTAGATATAGAAACCCCAGACACTCATATTTCTTACATGCCCACT
ATTAAGGAAGGTAACTCACGAGAACTAATGGCCAACAATCTATGCCCAACAGGCCTAAT
TACATTGCTTTTAGGGACAATTTTATTGGTCTAATGTATTACAACAGCACGGGTAATATG
GGTGTTCTGGCGGGCCAAGCATCGCAGTTGAATGCTGTTGTAGATTTGCAAGACAGAAAC
ACAGAGCTTTCATACCAGCTTTTGCTTGATTCCATTGGTGATAGAACCAGGTACTTTTCT
ATGTGGAATCAGGCTGTTGACAGCTATGATCCAGATGTTAGAATTATTGAAAATCATGGA
```

Figure 27 (part 10 of 16)

```
ACTGAAGATGAACTTCCAAATTACTGCTTTCCACTGGGAGGTGTGATTAATACAGAGACT
CTTACCAAGGTAAAACCTAAAACAGGTCAGGAAAATGGATGGGAAAAAGATGCTACAGAA
TTTTCAGATAAAAATGAAATAAGAGTTGGAAATAATTTTGCCATGGAAATCAATCTAAAT
GCCAACCTGTGGAGAAATTTCCTGTACTCCAACATAGCGCTGTATTTGCCCGACAAGCTA
AAGTACAGTCCTTCCAACGTAAAAATTTCTGATAACCCAAACACCTACGACTACATGAAC
AAGCGAGTGGTGGCTCCCGGGTTAGTGGACTGCTACATTAACCTTGGAGCACGCTGGTCC
CTTGACTATATGGACAACGTCAACCCATTTAACCACCACCGCAATGCTGGCCTGCGCTAC
CGCTCAATGTTGCTGGGCAATGGTCGCTATGTGCCCTTCCACATCCAGGTGCCTCAGAAG
TTCTTTGCCATTAAAAACCTCCTTCTCCTGCCGGGCTCATACACCTACGAGTGGAACTTC
AGGAAGGATGTTAACATGGTTCTGCAGAGCTCCCTAGGAAATGACCTAAGGGTTGACGGA
GCCAGCATTAAGTTTGATAGGATTTGCCTTTACGCCACCTTCTTCCCCATGGCCCACAAC
ACCGCCTCCACGCTTGAGGCCATGCTTAGAAACGACACCAACGACCAGTCCTTTAACGAC
TATCTCTCCGCCGCCAACATGCTCTACCCTATACCCGCCAACGCTACCAACGTGCCCATA
TCCATCCCCTCCCGCAACTGGGCGGCTTTCGCGGCTGGGCCTTCACGCGCCTTAAGACT
AAGGAAACCCCATCACTGGGCTCGGGCTACGACCCTTATTACACCTACTCTGGCTCTATA
CCCTACCTAGATGGAACCTTTTACCTCAACCACACCTTTAAGAAGGTGGCCATTACCTTT
GACTCTTCTGTCAGCTGGCCTGGCAATGACCGCCTGCTTACCCCCAACGAGTTTGAAATT
AAGCGCTCAGTTGACGGGGAGGGTTACAACGTTGCCCAGTGTAACATGACCAAAGACTGG
TTCCTGGTACAAATGCTAGCTAACTACAACATTGGCTACCAGGGCTTCTATATCCCAGAG
AGCTACAAGGACCGCATGTACTCCTTCTTTAGAAACTTCCAGCCCATGAGCCGTCAGGTG
GTGGATGATACTAAATACAAGGACTACCAACAGGTGGGCATCCTACACCAACACAACAAC
TCTGGATTTGTTGGCTACCTTGCCCCCACCATGCGCGAAGGACAGGCCTACCCTGCTAAC
TTCCCCTATCCGCTTATAGGCAAGACCGCAGTTGACAGCATTACCCAGAAAAAGTTTCTT
TGCGATCGCACCCTTTGGCGCATCCCATTCTCCAGTAACTTTATGTCCATGGGCGCACTC
ACAGACCTGGGCCAAAACCTTCTCTACGCCAACTCCGCCCACGCGCTAGACATGACTTTT
GAGGTGGATCCCATGGACGAGCCCACCCTTCTTTATGTTTTGTTTGAAGTCTTTGACGTG
GTCCGTGTGCACCGGCCGCACCGCGGCGTCATCGAAACCGTGTACCTGCGCACGCCCTTC
TCGGCCGGCAACGCCACAACATAAAGAAGCAAGCAACATCAACAACAGCTGCCGCCATGG
GCTCCAGTGAGCAGGAACTGAAAGCCATTGTCAAAGATCTTGGTTGTGGGCCATATTTTT
TGGGCACCTATGACAAGCGCTTTCCAGGCTTTGTTTCTCCACACAAGCTCGCCTGCGCCA
TAGTCAATACGGCCGGTCGCGAGACTGGGGGCGTACACTGGATGGCCTTTGCCTGGAACC
CGCACTCAAAAACATGCTACCTCTTTGAGCCCTTTGGCTTTTCTGACCAGCGACTCAAGC
AGGTTTACCAGTTTGAGTACGAGTCACTCCTGCGCCGTAGCGCCATTGCTTCTTCCCCCG
ACCGCTGTATAACGCTGGAAAAGTCCACCCAAAGCGTACAGGGGCCCAACTCGGCCGCCT
GTGGACTATTCTGCTGCATGTTTCTCCACGCCTTTGCCAACTGGCCCCAAAACTCCCATGG
ATCACAACCCCACCATGAACCTTATTACCGGGGTACCCAACTCCATGCTCAACAGTCCCC
AGGTACAGCCCACCCTGCGTCGCAACCAGGAACAGCTCTACAGCTTCCTGGAGCGCCACT
CGCCCTACTTCCGCAGCCACAGTGCGCAGATTAGGAGCGCCACTTCTTTTTGTCACTTGA
AAAACATGTAAAAATAATGTACTAGAGACACTTTCAATAAAGGCAAATGCTTTTATTTGT
ACACTCTCGGGTGATTATTTACCCCCACCCTTGCCGTCTGCGCCGTTTAAAAATCAAAGG
GGTTCTGCCGCGCATCGCTATGCGCCACTGGCAGGGACACGTTGCGATACTGGTGTTTAG
TGCTCCACTTAAACTCAGGCACAACCATCCGCGGCAGCTCGGTGAAGTTTTCACTCCACA
```

Figure 27 (part 11 of 16)

```
GGCTGCGCACCATCACCAACGCGTTTAGCAGGTCGGGCGCCGATATCTTGAAGTCGCAGT
TGGGGCCTCCGCCCTGCGCGCGAGTTGCGATACACAGGGTTGCAGCACTGGAACACTA
TCAGCGCCGGGTGGTGCACGCTGGCCAGCACGCTCTTGTCGGAGATCAGATCCGCGTCCA
GGTCCTCCGCGTTGCTCAGGGCGAACGGAGTCAACTTTGGTAGCTGCCTTCCCAAAAAGG
GCGCGTGCCCAGGCTTTGAGTTGCACTCGCACCGTAGTGGCATCAAAAGGTGACCGTGCC
CGGTCTGGGCGTTAGGATACAGCGCCTGCATAAAAGCCTTGATCTGCTTAAAAGCCACCT
GAGCCTTTGCGCCTTCAGAGAAGAACATGCCGCAAGACTTGCCGGAAAACTGATTGGCCG
GACAGGCCGCGTCGTGCACGCAGCACCTTGCGTCGGTGTTGGAGATCTGCACCACATTTC
GGCCCCACCGGTTCTTCACGATCTTGGCCTTGCTAGACTGCTCCTTCAGCGCGCGCTGCC
CGTTTTCGCTCGTCACATCCATTTCAATCACGTGCTCCTTATTTATCATAATGCTTCCGT
GTAGACACTTAAGCTCGCCTTCGATCTCAGCGCAGCGGTGCAGCCACAACGCGCAGCCCG
TGGGCTCGTGATGCTTGTAGGTCACCTCTGCAAACGACTGCAGGTACGCCTGCAGGAATC
GCCCCATCATCGTCACAAAGGTCTTGTTGCTGGTGAAGGTCAGCTGCAACCCGCGGTGCT
CCTCGTTCAGCCAGGTCTTGCATACGGCCGCCAGAGCTTCCACTTGGTCAGGCAGTAGTT
TGAAGTTCGCCTTTAGATCGTTATCCACGTGGTACTTGTCCATCAGCGCGCGCGCAGCCT
CCATGCCCTTCTCCCACGCAGACACGATCGGCACACTCAGCGGGTTCATCACCGTAATTT
CACTTTCCGCTTCGCTGGGCTCTTCCTCTTCCTCTTGCGTCCGCATACCACGCGCCACTG
GGTCGTCTTCATTCAGCCGCCGCACTGTGCGCTTACCTCCTTTGCCATGCTTGATTAGCA
CCGGTGGGTTGCTGAAACCCACCATTTGTAGCGCCACATCTTCTCTTTCTTCCTCGCTGT
CCACGATTACCTCTGGTGATGGCGGGCGCTCGGGCTTGGGAGAAGGGCGCTTCTTTTTCT
TCTTGGGCGCAATGGCCAAATCCGCCGCCGAGGTCGATGGCCGCGGGCTGGGTGTGCGCG
GCACCAGCGCGTCTTGTGATGAGTCTTCCTCGTCCTCGGACTCGATACGCCGCCTCATCC
GCTTTTTTGGGGGCGCCCGGGGAGGCGGCGGCGACGGGGACGGGGACGACACGTCCTCCA
TGGTTGGGGGACGTCGCGCCGCACCGCGTCCGCGCTCGGGGGTGGTTTCGCGCTGCTCCT
CTTCCCGACTGGCCATTTCCTTCTCCTATAGGCAGAAAAAGATCATGGAGTCAGTCGAGA
AGAAGGACAGCCTAACCGCCCCCTCTGAGTTCGCCACCACCGCCTCCACCGATGCCGCCA
ACGCGCCTACCACCTTCCCCGTCGAGGCACCCCGCTTGAGGAGGAGGAAGTGATTATCG
AGCAGGACCCAGGTTTTGTAAGCGAAGACGACGAGGACCGCTCAGTACCAACAGAGGATA
AAAAGCAAGACCAGGACAACGCAGAGGCAAACGAGGAACAAGTCGGGCGGGGGGACGAAA
GGCATGGCGACTACCTAGATGTGGGAGACGACGTGCTGTTGAAGCATCTGCAGCGCCAGT
GCGCCATTATCTGCGACGCGTTGCAAGAGCGCAGCGATGTGCCCCTCGCCATAGCGGATG
TCAGCCTTGCCTACGAACGCCACCTATTCTCACCGCGCGTACCCCCAAACGCCAAGAAA
ACGGCACATGCGAGCCCAACCCGCGCCTCAACTTCTACCCCGTATTTGCCGTGCCAGAGG
TGCTTGCCACCTATCACATCTTTTTTCCAAAACTGCAAGATACCCCTATCCTGCCGTGCCA
ACCGCAGCCGAGCGGACAAGCAGCTGGCCTTGCGGCAGGGCGCTGTCATACCTGATATCG
CCTCGCTCAACGAAGTGCCAAAAATCTTTGAGGGTCTTGGACGCGACGAGAAGCGCGCGG
CAAACGCTCTGCAACAGGAAAACAGCGAAAATGAAAGTCACTCTGGAGTGTTGGTGGAAC
TCGAGGGTGACAACGCGCGCCTAGCCGTACTAAAACGCAGCATCGAGGTCACCCACTTTG
CCTACCCGGCACTTAACCTACCCCCAAGGTCATGAGCACAGTCATGAGTGAGCTGATCG
TGCGCCGTGCGCAGCCCCTGGAGAGGGATGCAAATTTGCAAGAACAAACAGAGGAGGGCC
TACCCGCAGTTGGCGACGAGCAGCTAGCGCGCTGGCTTCAAACGCGCGAGCCTGCCGACT
TGGAGGAGCGACGCAAACTAATGATGGCCGCAGTGCTCGTTACCGTGGAGCTTGAGTGCA
```

Figure 27 (part 12 of 16)

TGCAGCGGTTCTTTGCTGACCCGGAGATGCAGCGCAAGCTAGAGGAAACATTGCACTACA
CCTTTCGACAGGGCTACGTACGCCAGGCCTGCAAGATCTCCAACGTGGAGCTCTGCAACC
TGGTCTCCTACCTTGGAATTTTGCACGAAAACCGCCTTGGGCAAACGTGCTTCATTCCA
CGCTCAAGGGCGAGGCGCGCCGCGACTACGTCCGCGACTGCGTTTACTTATTTCTATGCT
ACACCTGGCAGACGGCCATGGGCGTTTGGCAGCAGTGCTTGGAGGAGTGCAACCTCAAGG
AGCTGCAGAAACTGCTAAAGCAAAACTTGAAGGACCTATGGACGGCCTTCAACGAGCGCT
CCGTGGCCGCGCACCTGGCGGACATCATTTTCCCCGAACGCCTGCTTAAAACCCTGCAAC
AGGGTCTGCCAGACTTCACCAGTCAAAGCATGTTGCAGAACTTTAGGAACTTTATCCTAG
AGCGCTCAGGAATCTTGCCCGCCACCTGCTGTGCACTTCCTAGCGACTTTGTGCCCATTA
AGTACCGCGAATGCCCTCCGCCGCTTTGGGGCCACTGCTACCTTCTGCAGCTAGCCAACT
ACCTTGCCTACCACTCTGACATAATGGAAGACGTGAGCGGTGACGGTCTACTGGAGTGTC
ACTGTCGCTGCAACCTATGCACCCCGCACCGCTCCCTGGTTTGCAATTCGCAGCTGCTTA
ACGAAAGTCAAATTATCGGTACCTTTGAGCTGCAGGGTCCCTCGCCTGACGAAAAGTCCG
CGGCTCCGGGGTTGAAACTCACTCCGGGGCTGTGGACGTCGGCTTACCTTCGCAAATTTG
TACCTGAGGACTACCACGCCCACGAGATTAGGTTCTACGAAGACCAATCCCGCCCGCCAA
ATGCGGAGCTTACCGCCTGCGTCATTACCCAGGGCCACATTCTTGGCCAATTGCAAGCCA
TCAACAAAGCCCGCCAAGAGTTTCTGCTACGAAAGGGACGGGGGGTTTACTTGGACCCCC
AGTCCGGCGAGGAGCTCAACCCAATCCCCCCGCCGCCGCAGCCCTATCAGCAGCAGCCGC
GGGCCCTTGCTTCCCAGGATGGCACCCAAAAAGAAGCTGCAGCTGCCGCCGCCACCCACG
GACGAGGAGGAATACTGGGACAGTCAGGCAGAGGAGGTTTTGGACGAGGAGGAGGAGGAC
ATGATGGAAGACTGGGAGAGCCTAGACGAGGAAGCTTCCGAGGTCGAAGAGGTGTCAGAC
GAAACACCGTCACCCTCGGTCGCATTCCCCTCGCCGGCGCCCAGAAATCGGCAACCGGT
TCCAGCATGGCTACAACCTCCGCTCCTCAGGCGCCGCCGGCACTGCCCGTTCGCCGACCC
AACCGTAGATGGGACACCACTGGAACCAGGGCCGGTAAGTCCAAGCAGCCGCCGCCGTTA
GCCCAAGAGCAACAACAGCGCCAAGGCTACCGCTCATGGCGCGGGCACAAGAACGCCATA
GTTGCTTGCTTGCAAGACTGTGGGGGCAACATCTCCTTCGCCCGCCGCTTTCTTCTCTAC
CATCACGGCGTGGCCTTCCCCCGTAACATCCTGCATTACTACCGTCATCTCTACAGCCCA
TACTGCACCGGCGGCAGCGGCAGCGGCAGCAACAGCAGCGGCCACACAGAAGCAAAGGCG
ACCGGATAGCAAGACTCTGACAAAGCCCAAGAAATCCACAGCGGCGGCAGCAGCAGGAGG
AGGAGCGCTGCGTCTGGCGCCCAACGAACCCGTATCGACCCGCGAGCTTAGAAACAGGAT
TTTTCCCACTCTGTATGCTATATTTCAACAGAGCAGGGGCCAAGAACAAGAGCTGAAAAT
AAAAAACAGGTCTCTGCGATCCCTCACCCGCAGCTGCCTGTATCACAAAAGCGAAGATCA
GCTTCGGCGCACGCTGGAAGACGCGGAGGCTCTCTTCAGTAAATACTGCGCGCTGACTCT
TAAGGACTAGTTTCGCGCCCTTTCTCAAATTTAAGCGCGAAAACTACGTCATCTCCAGCG
GCCACACCCGGCGCCAGCACCTGTCGTCAGCGCCATTATGAGCAAGGAAATTCCCACGCC
CTACATGTGGAGTTACCAGCCACAAATGGGACTTGCGGCTGGAGCTGCCCAAGACTACTC
AACCCGAATAAACTACATGAGCGCGGGACCCCACATGATATCCCGGGTCAACGGAATCCG
CGCCCACCGAAACCGAATTCTCTTGGAACAGGCGGCTATTACCACCACACCTCGTAATAA
CCTTAATCCCCGTAGTTGGCCCGCTGCCCTGGTGTACCAGGAAAGTCCCGCTCCCACCAC
TGTGGTACTTCCCAGAGACGCCCAGGCCGAAGTTCAGATGACTAACTCAGGGGCGCAGCT
TGCGGGCGGCTTTCGTCACAGGGTGCGGTCGCCCGGGCAGGGTATAACTCACCTGACAAT
CAGAGGGCGAGGTATTCAGCTCAACGACGAGTCGGTGAGCTCCTCGCTTGGTCTCCGTCC

Figure 27 (part 13 of 16)

```
GGACGGGACATTTCAGATCGGCGGCGCCGGCCGTCCTTCATTCACGCCTCGTCAGGCAAT
CCTAACTCTGCAGACCTCGTCCTCTGAGCCGCGCTCTGGAGGCATTGGAACTCTGCAATT
TATTGAGGAGTTTGTGCCATCGGTCTACTTTAACCCCTTCTCGGGACCTCCCGGCCACTA
TCCGGATCAATTTATTCCTAACTTTGACGCGGTAAAGGACTCGGCGGACGGCTACGACTG
AATGTTAAGTGGAGAGGCAGAGCAACTGCGCCTGAAACACCTGGTCCACTGTCGCCGCCA
CAAGTGCTTTGCCCGCGACTCCGGTGAGTTTTGCTACTTTGAATTGCCCGAGGATCATAT
CGAGGGCCCGGCGCACGGCGTCCGGCTTACCGCCCAGGGAGAGCTTGCCCGTAGCCTGAT
TCGGGAGTTTACCCAGCGCCCCCTGCTAGTTGAGCGGGACAGGGGACCCTGTGTTCTCAC
TGTGATTTGCAACTGTCCTAACCTTGGATTACATCAAGATCCTCTAGTTATAACTAGAGT
ACCCGGGGATCTTATTCCCTTTAACTAATAAAAAAAATAATAAAGCATCACTTACTTAA
AATCAGTTAGCAAATTTCTGTCCAGTTTATTCAGCAGCACCTCCTTGCCCTCCTCCCAGC
TCTGGTATTGCAGCTTCCTCCTGGCTGCAAACTTTCTCCACAATCTAAATGGAATGTCAG
TTTCCTCCTGTTCCTGTCCATCCGCACCCACTATCTTCATGTTGTTGCAGATGAAGCGCG
CAAGACCGTCTGAAGATACCTTCAACCCCGTGTATCCATATGACACGGAAACCGGTCCTC
CAACTGTGCCTTTTCTTACTCCTCCCTTTGTATCCCCCAATGGGTTTCAAGAGAGTCCCC
CTGGGGTACTCTCTTTGCGCCTATCCGAACCTCTAGTTACCTCCAATGGCATGCTTGCGC
TCAAAATGGGCAACGGCCTCTCTCTGGACGAGGCCGGCAACCTTACCTCCCAAAATGTAA
CCACTGTGAGCCCACCTCTCAAAAAAACCAAGTCAAACATAAACCTGGAAATATCTGCAC
CCCTCACAGTTACCTCAGAAGCCCTAACTGTGGCTGCCGCCGCACCTCTAATGGTCGCGG
GCAACACACTCACCATGCAATCACAGGCCCCGCTAACCGTGCACGACTCCAAACTTAGCA
TTGCCACCCAAGGACCCCTCACAGTGTCAGAAGGAAAGCTAGCCCTGCAAACATCAGGCC
CCCTCACCACCACCGATAGCAGTACCCTTACTATCACTGCCTCACCCCCTCTAACTACTG
CCACTGGTAGCTTGGGCATTGACTTGAAAGAGCCCATTTATACACAAAATGGAAAACTAG
GACTAAAGTACGGGGCTCCTTTGCATGTAACAGACGACCTAAACACTTTGACCGTAGCAA
CTGGTCCAGGTGTGACTATTAATAATACTTCCTTGCAAACTAAAGTTACTGGAGCCTTGG
GTTTTGATTCACAAGGCAATATGCAACTTAATGTAGCAGGAGGACTAAGGATTGATTCTC
AAAACAGACGCCTTATACTTGATGTTAGTTATCCGTTTGATGCTCAAAACCAACTAAATC
TAAGACTAGGACAGGGCCCTCTTTTTATAAACTCAGCCCACAACTTGGATATTAACTACA
ACAAAGGCCTTTACTTGTTTACAGCTTCAAACAATTCCAAAAAGCTTGAGGTTAACCTAA
GCACTGCCAAGGGGTTGATGTTTGACGCTACAGCCATAGCCATTAATGCAGGAGATGGGC
TTGAATTTGGTTCACCTAATGCACCAAACACAAATCCCCTCAAAACAAAAATTGGCCATG
GCCTAGAATTTGATTCAAACAAGGCTATGGTTCCTAAACTAGGAACTGGCCTTAGTTTTG
ACAGCACAGGTGCCATTACAGTAGGAAACAAAAATAATGATAAGCTAACTTTGTGGACCA
CACCAGCTCCATCTCCTAACTGTAGACTAAATGCAGAGAAAGATGCTAAACTCACTTTGG
TCTTAACAAAATGTGGCAGTCAAATACTTGCTACAGTTTCAGTTTTGGCTGTTAAAGGCA
GTTTGGCTCCAATATCTGGAACAGTTCAAAGTGCTCATCTTATTATAAGATTTGACGAAA
ATGGAGTGCTACTAAACAATTCCTTCCTGGACCCAGAATATTGGAACTTTAGAAATGGAG
ATCTTACTGAAGGCACAGCCTATACAAACGCTGTTGGATTTATGCCTAACCTATCAGCTT
ATCCAAAATCTCACGGTAAAACTGCCAAAAGTAACATTGTCAGTCAAGTTTACTTAAACG
GAGACAAAACTAAACCTGTAACACTAACCATTACACTAAACGGTACACAGGAAACAGGAG
ACACAACTCCAAGTGCATACTCTATGTCATTTTCATGGGACTGGTCTGGCCACAACTACA
TTAATGAAATATTTGCCACATCCTCTTACACTTTTTCATACATTGCCCAAGAATAAAGAA
```

Figure 27 (part 14 of 16)

```
TCGTTTGTGTTATGTTTCAACGTGTTTATTTTTCAATTGCAGAAAATTTCAAGTCATTTT
TCATTCAGTAGTATAGCCCCACCACCACATAGCTTATACAGATCACCGTACCTTAATCAA
ACTCACAGAACCCTAGTATTCAACCTGCCACCTCCCTCCCAACACACAGAGTACACAGTC
CTTTCTCCCCGGCTGGCCTTAAAAAGCATCATATCATGGGTAACAGACATATTCTTAGGT
GTTATATTCCACACGGTTTCCTGTCGAGCCAAACGCTCATCAGTGATATTAATAAACTCC
CCGGGCAGCTCACTTAAGTTCATGTCGCTGTCCAGCTGCTGAGCCACAGGCTGCTGTCCA
ACTTGCGGTTGCTTAACGGGCGGCGAAGGAGAAGTCCACGCCTACATGGGGGTAGAGTCA
TAATCGTGCATCAGGATAGGCGGTGGTGCTGCAGCAGCGCGCGAATAAACTGCTGCCGC
CGCCGCTCCGTCCTGCAGGAATACAACATGGCAGTGGTCTCCTCAGCGATGATTCGCACC
GCCCGCAGCATAAGGCGCCTTGTCCTCCGGGCACAGCAGCGCACCCTGATCTCACTTAAA
TCAGCACAGTAACTGCAGCACAGCACCACAATATTGTTCAAAATCCCACAGTGCAAGGCG
CTGTATCCAAAGCTCATGGCGGGGACCACAGAACCCACGTGGCCATCATACCACAAGCGC
AGGTAGATTAAGTGGCGACCCCTCATAAACACGCTGGACATAAACATTACCTCTTTTGGC
ATGTTGTAATTCACCACCTCCCGGTACCATATAAACCTCTGATTAAACATGGCGCCATCC
ACCACCATCCTAAACCAGCTGGCCAAAACCTGCCCGCCGGCTATACACTGCAGGGAACCG
GGACTGGAACAATGACAGTGGAGAGCCCAGGACTCGTAACCATGGATCATCATGCTCGTC
ATGATATCAATGTTGGCACAACACAGGCACACGTGCATACACTTCCTCAGGATTACAAGC
TCCTCCCGCGTTAGAACCATATCCCAGGGAACAACCCATTCCTGAATCAGCGTAAATCCC
ACACTGCAGGGAAGACCTCGCACGTAACTCACGTTGTGCATTGTCAAAGTGTTACATTCG
GGCAGCAGCGGATGATCCTCCAGTATGGTAGCGCGGGTTTCTGTCTCAAAAGGAGGTAGA
CGATCCCTACTGTACGGAGTGCGCCGAGACAACCGAGATCGTGTTGGTCGTAGTGTCATG
CCAAATGGAACGCCGGACGTAGTCATATTTCCTGAAGCAAAACCAGGTGCGGGCGTGACA
AACAGATCTGCGTCTCCGGTCTCGCCGCTTAGATCGCTCTGTGTAGTAGTTGTAGTATAT
CCACTCTCTCAAAGCATCCAGGCGCCCCTGGCTTCGGGTTCTATGTAAACTCCTTCATG
CGCCGCTGCCCTGATAACATCCACCACCGCAGAATAAGCCACACCCAGCCAACCTACACA
TTCGTTCTGCGAGTCACACACGGGAGGAGCGGGAAGAGCTGGAAGAACCATGTTTTTTTT
TTTATTCCAAAAGATTATCCAAAACCTCAAAATGAAGATCTATTAAGTGAACGCGCTCCC
CTCCGGTGGCGTGGTCAAACTCTACAGCCAAAGAACAGATAATGGCATTTGTAAGATGTT
GCACAATGGCTTCCAAAAGGCAAACGGCCCTCACGTCCAAGTGGACGTAAAGGCTAAACC
CTTCAGGGTGAATCTCCTCTATAAACATTCCAGCACCTTCAACCATGCCCAAATAATTCT
CATCTCGCCACCTTCTCAATATATCTCTAAGCAAATCCCGAATATTAAGTCCGGCCATTG
TAAAAATCTGCTCCAGAGCGCCCTCCACCTTCAGCCTCAAGCAGCGAATCATGATTGCAA
AAATTCAGGTTCCTCACAGACCTGTATAAGATTCAAAAGCGGAACATTAACAAAAATACC
GCGATCCCGTAGGTCCCTTCGCAGGGCCAGCTGAACATAATCGTGCAGGTCTGCACGGAC
CAGCGCGGCCACTTCCCCGCCAGGAACCTTGACAAAAGAACCCACACTGATTATGACACG
CATACTCGGAGCTATGCTAACCAGCGTAGCCCCGATGTAAGCTTTGTTGCATGGGCGGCG
ATATAAAATGCAAGGTGCTGCTCAAAAAATCAGGCAAAGCCTCGCGCAAAAAAGAAAGCA
CATCGTAGTCATGCTCATGCAGATAAAGGCAGGTAAGCTCCGGAACCACCACAGAAAAAG
ACACCATTTTTCTCTCAAACATGTCTGCGGGTTTCTGCATAAACACAAAATAAAATAACA
AAAAAACATTTAAACATTAGAAGCCTGTCTTACAACAGGAAAAACAACCCTTATAAGCAT
AAGACGGACTACGGCCATGCCGGCGTGACCGTAAAAAAACTGGTCACCGTGATTAAAAAG
CACCACCGACAGCTCCTCGGTCATGTCCGGAGTCATAATGTAAGACTCGGTAAACACATC
```

Figure 27 (part 15 of 16)

```
AGGTTGATTCATCGGTCAGTGCTAAAAAGCGACCGAAATAGCCCGGGGGAATACATACCC
GCAGGCGTAGAGACAACATTACAGCCCCCATAGGAGGTATAACAAAATTAATAGGAGAGA
AAAACACATAAACACCTGAAAAACCCTCCTGCCTAGGCAAAATAGCACCCTCCCGCTCCA
GAACAACATACAGCGCTTCACAGCGGCAGCCTAACAGTCAGCCTTACCAGTAAAAAAGAA
AACCTATTAAAAAAACACCACTCGACACGGCACCAGCTCAATCAGTCACAGTGTAAAAAA
GGGCCAAGTGCAGAGCGAGTATATATAGGACTAAAAAATGACGTAACGGTTAAAGTCCAC
AAAAAACACCCAGAAAACCGCACGCGAACCTACGCCCAGAAACGAAAGCCAAAAAACCCA
CAACTTCCTCAAATCGTCACTTCCGTTTTCCCACGTTACGTAACTTCCCATTTTAAGAAA
ACTACAATTCCCAACACATACAAGTTACTCCGCCCTAAAACCTACGTCACCCGCCCCGTT
CCCACGCCCCGCGCCACGTCACAAACTCCACCCCCTCATTATCATATTGGCTTCAATCCA
AAATAAGGTATATTATTGATGATNNN
```

Figure 27 (part 16 of 16)

SEQUENCE LISTING

```
<160> NUMBER OF SEQ ID NOS: 11

<210> SEQ ID NO 1
<211> LENGTH: 5252
<212> TYPE: DNA
<213> ORGANISM: Artificial Sequence
<220> FEATURE:
<223> OTHER INFORMATION: Vector comprising a tricistronic expression
      cassette as insert

<400> SEQUENCE: 1
tagtaatcaa ttacggggtc attagttcat agcccatata tggagttccg cgttacataa      60
cttacggtaa atggcccgcc tggctgaccg cccaacgacc cccgcccatt gacgtcaata     120
atgacgtatg ttcccatagt aacgccaata gggactttcc attgacgtca atgggtggag     180
tatttacggt aaactgccca cttggcagta catcaagtgt atcatatgcc aagtacgccc     240
cctattgacg tcaatgacgg taaatggccc gcctggcatt atgcccagta catgacctta     300
tgggactttc ctacttggca gtacatctac gtattagtca tcgctattac catggtgatg     360
cggttttggc agtacatcaa tgggcgtgga tagcggtttg actcacgggg atttccaagt     420
```

```
ctccacccca ttgacgtcaa tgggagtttg ttttggcacc aaaatcaacg ggactttcca    480
aaatgtcgta acaactccgc cccattgacg caaatgggcg gtaggcgtgt acggtgggag    540
gtctatataa gcagagctgg tttagtgaac cgtcagatcc gctagagatc tggatccgaa    600
ttcgccgcca ccatgggtcc tcagaagcta accatctcct ggtttgccat cgttttgctg    660
gtgtctccac tcatggccat gtgggagctg gagaagacg tttatgttgt agaggtggac     720
tggactcccg atgcccctgg agaaacagtg aacctcacct gtgacacgcc tgaagaagat    780
gacatcacct ggacctcaga ccagagacat ggagtcatag gctctggaaa gaccctgacc    840
atcactgtca aagagtttct agatgctggc cagtacacct gccacaaagg aggcgagact    900
ctgagccact cacatctgct gctccacaag aaggaaaatg gaatttggtc cactgaaatt    960
ttaaaaaatt tcaaaaacaa gactttcctg aagtgtgaag caccaaatta ctccggacgg   1020
ttcacgtgct catggctggt gcaaagaaac atggacttga agttcaacat caagagcagt   1080
agcagttccc ctgactctcg ggcagtgaca tgtggaatgg cgtctctgtc tgcagagaag   1140
gtcacactgg accaaaggga ctatgagaag tattcagtgt cctgccagga ggatgtcacc   1200
tgcccaactg ccgaggagac cctgcccatt gaactggcgt tggaagcacg gcagcagaat   1260
aaatatgaga actacagcac cagcttcttc atcagggaca tcatcaaacc agaccgccc    1320
aagaacttgc agatgaagcc tttgaagaac tcacaggtgg aggtcagctg ggagtaccct   1380
gactcctgga gcactcccca ttcctacttc tccctcaagt tctttgttcg aatccagcgc   1440
aagaaagaaa agatgaagga gacagaggag gggtgtaacc agaaaggtgc gttcctcgta   1500
gagaagacat ctaccgaagt ccaatgcaaa ggcgggaatg tctgcgtgca agctcaggat   1560
cgctattaca attcctcatg cagcaagtgg gcatgtgttc cctgcagggt ccgatccggt   1620
ggcggtggct cgggcggtgg tgggtcgggt ggcggcggat ctagggtcat tccagtctct   1680
ggacctgcca ggtgtcttag ccagtcccga aacctgctga gaccacaga tgacatggtg   1740
aagacggcca gagaaaagct gaaacattat tcctgcactg ctgaagacat cgatcatgaa   1800
gacatcacac gggaccaaac cagcacattg aagacctgtt taccactgga actcacaag   1860
aacgagagtt gcctggctac tagagagact cttccacaa caagagggag ctgcctgccc   1920
ccacagaaga cgtctttgat gatgaccctg tgccttggta gcatctatga ggacttgaag   1980
atgtaccaga cagagttcca ggccatcaac gcagcacttc agaatcacaa ccatcagcag   2040
atcattctag acaagggcat gctggtggcc atcgatgagc tgatgcagtc tctgaatcat   2100
aatggcgaga ctctgcgcca gaaacctcct gtgggagaag cagacccta cagagtgaaa   2160
atgaagctct gcatcctgct tcacgccttc agcacccgcg tcgtgaccat caacagggtg   2220
atgggctatc tgagctccgc ctgagaattg atccggatta gtccaatttg ttaaagacag   2280
gatgaagctt aaaacagctc tggggttgta cccacccag aggcccacgt ggcggctagt    2340
actccggtat tgcggtaccc ttgtacgcct gttttatact cccttcccgt aacttagacg   2400
cacaaaacca agttcaatag aaggggtac aaaccagtac caccacgaac aagcacttct    2460
gtttccccgg tgatgtcgta tagactgctt gcgtggttga aagcgacgga tccgttatcc   2520
gcttatgtac ttcgagaagc ccagtaccac ctcggaatct tcgatgcgtt gcgctcagca   2580
ctcaaccccca gagtgtagct taggctgatg agtctggaca tccctcaccg gtgacggtgg   2640
tccaggctgc gttggcggcc tacctatggc taacgccatg ggacgctagt tgtgaacaag   2700
gtgtgaagag cctattgagc tacataagaa tcctccggcc cctgaatgcg gctaatccca   2760
acctcggagc aggtggtcac aaaccagtga ttggcctgtc gtaacgcgca agtccgtggc   2820
```

```
ggaaccgact actttgggtg tccgtgtttc cttttatttt attgtggctg cttatggtga    2880
caatcacaga ttgttatcat aaagcgaatt ggattgcggc cgcgccacca tggaccagca    2940
cacacttgat gtggaggata ccgcggatgc cagacatcca gcaggtactt cgtgcccctc    3000
ggatgcggcg ctcctcagag ataccgggct cctcgcggac gctgcgctcc tctcagatac    3060
tgtgcgcccc acaaatgccg cgctccccac ggatgctgcc taccctgcgg ttaatgttcg    3120
ggatcgcgag gccgcgtggc cgcctgcact gaacttctgt tcccgccacc caaagctcta    3180
tggcctagtc gctttggttt tgctgcttct gatcgccgcc tgtgttccta tcttcacccg    3240
caccgagcct cggccagcgc tcacaatcac cacctcgccc aacctgggta cccgagagaa    3300
taatgcagac caggtcaccc ctgtttccca cattggctgc cccaacacta cacaacaggg    3360
ctctcctgtg ttcgccaagc tactggctaa aaaccaagca tcgttgtgca atacaactct    3420
gaactggcac agccaagatg gagctggagc tcataccta tctcaaggtc tgaggtacga    3480
agaagacaaa aaggagttgg tggtagacag tcccgggctc tactacgtat ttttggaact    3540
gaagctcagt ccaacattca caaacacagg ccacaaggtg cagggctggg tctctcttgt    3600
tttgcaagca aagcctcagg tagatgactt tgacaacttg gccctgacag tggaactgtt    3660
cccttgctcc atggagaaca gttagtggaa ccgttcctgg agtcaactgt tgctcctgaa    3720
ggctggccac cgcctcagtg tgggtctgag ggcttatctg catggagccc aggatgcata    3780
cagagactgg gagctgtctt atcccaacac caccagcttt ggactctttc ttgtgaaacc    3840
cgacaaccca tgggaatgag aactatcctt cttgtgactg gcgcgcctga tcaatcgatg    3900
tttaaacgtt attttccacc atattgccgt cttttggcaa tgtgagggcc cggaaacctg    3960
gccctgtctt cttgacgagc attcctaggg gtctttcccc tctcgccaaa ggaatgcaag    4020
gtctgttgaa tgtcgtgaag gaagcagttc ctctggaagc ttcttgaaga caaacaacgt    4080
ctgtagcgac cctttgcagg cagcggaacc ccccacctgg cgacaggtgc ctctgcggcc    4140
aaaagccacg tgtataagat acacctgcaa aggcggcaca accccagtgc cacgttgtga    4200
gttggatagt tgtggaaaga gtcaaatggc tctcctcaag cgtattcaac aaggggctga    4260
aggatgccca gaaggtaccc cattgtatgg gatctgatct ggggcctcgg tgcacatgct    4320
ttacgtgtgt ttagtcgagg ttaaaaaaac gtctaggccc cccgaaccac ggggacgtgg    4380
ttttcctttg aaaacacga ttctcgagac tagtgccacc atgtacagca tgcagctcgc    4440
atcctgtgtc acattgacac ttgtgctcct tgtcaacagc gcacccactt caagctccac    4500
ttcaagctct acagcggaag cacagcagca gcagcagcag cagcagcagc agcagcagca    4560
cctggagcag ctgttgatgg acctacagga gctcctgagc aggatggaga attacaggaa    4620
cctgaaactc cccaggatgc tcaccttcaa attttacttg cccaagcagg ccacagaatt    4680
gaaagatctt cagtgcctag aagatgaact tggacctctg cggcatgttc tggatttgac    4740
tcaaagcaaa agctttcaat tggaagatgc tgagaatttc atcagcaata tcagagtaac    4800
tgttgtaaaa ctaaagggct ctgacaacac atttgagtgc caattcgatg atgagtcagc    4860
aactgtggtg gactttctga ggagatggat agccttctgt caaagcatca tctcaacaag    4920
ccctcaataa ctatgtaacg cgtgctagca tggccggccg cggccgcggc cgctcgagcc    4980
taagcttcta gataagatat ccgatccacc ggatctagat aactgatcat aatcagccat    5040
accacatttg tagaggtttt acttgcttta aaaaacctcc cacacctccc cctgaacctg    5100
aaacataaaa tgaatgcaat tgttgttgtt aacttgttta ttgcagctta taatggttac    5160
aaataaagca atagcatcac aaatttcaca aataaagcat ttttttcact gcattctagt    5220
```

```
tgtggtttgt ccaaactcat caatgtatct ta                                   5252

<210> SEQ ID NO 2
<211> LENGTH: 987
<212> TYPE: DNA
<213> ORGANISM: Homo sapiens

<400> SEQUENCE: 2
atgtgtcacc agcagttggt catctcttgg ttttccctgg tttttctggc atctcccctc       60
gtggccatat gggaactgaa gaaagatgtt tatgtcgtag aattggattg gtatccggat      120
gcccctggag aaatggtggt cctcacctgt gacacccctg aagaagatgg tatcacctgg      180
accttggacc agagcagtga ggtcttaggc tctggcaaaa ccctgaccat ccaagtcaaa      240
gagtttggag atgctggcca gtacacctgt cacaaaggag gcgaggttct aagccattcg      300
ctcctgctgc ttcacaaaaa ggaagatgga atttggtcca ctgatatttt aaaggaccag      360
aaagaaccca aaaataagac ctttctaaga tgcgaggcca agaattattc tggacgtttc      420
acctgctggt ggctgacgac aatcagtact gatttgacat tcagtgtcaa aagcagcaga      480
ggctcttctg accccaagg ggtgacgtgc ggagctgcta cactctctgc agagagagtc       540
agaggggaca acaaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca aacctgaccc acccaagaac      720
ttgcagctga gccattaaa gaattctcgg caggtggagg tcagctggga gtaccctgac       780
acctggagta ctccacattc ctacttctcc ctgacattct gcgttcaggt ccagggcaag      840
agcaagagag aaaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagttag                                         987

<210> SEQ ID NO 3
<211> LENGTH: 762
<212> TYPE: DNA
<213> ORGANISM: Homo sapiens

<400> SEQUENCE: 3
atgtggcccc ctgggtcagc ctcccagcca ccgccctcac ctgccgcggc cacaggtctg       60
catccagcgg ctcgccctgt gtccctgcag tgccggctca gcatgtgtcc agcgcgcagc      120
ctcctccttg tggctaccct ggtcctcctg gaccacctca gtttggccag aaacctcccc      180
gtggccactc cagacccagg aatgttccca tgccttcacc actcccaaaa cctgctgagg      240
gccgtcagca acatgctcca gaaggccaga caaactctag aattttaccc ttgcacttct      300
gaagagattg atcatgaaga tatcacaaaa gataaaacca gcacagtgga ggcctgttta      360
ccattggaat taaccaagaa tgagagttgc ctaaattcca gagagacctc tttcataact      420
aatgggagtt gcctggcctc agaaagacc tcttttatga tggccctgtg ccttagtagt       480
atttatgaag acttgaagat gtaccaggtg gagttcaaga ccatgaatgc aaagcttctg      540
atggatccta agaggcagat cttttctagat caaaacatgc tggcagttat tgatgagctg      600
atgcaggccc tgaattttca cagtgagact gtgccacaaa atcctcccct tgaagaaccg      660 gattttata aaactaaaat caagctctgc atacttcttc atgctttcag aattcgggca      720
gtgactattg atagagtgat gagctatctg aatgcttcct aa                        762

<210> SEQ ID NO 4
```

<211> LENGTH: 768
<212> TYPE: DNA
<213> ORGANISM: Homo sapiens

<400> SEQUENCE: 4

| | | | | | |
|---|---|---|---|---|---|
| gtcatggaat | acgcctctga | cgcttcactg | gaccccgaag | ccccgtggcc | tcccgcgccc | 60 |
| cgcgctcgcg | cctgccgcgt | actgccttgg | gccctggtcg | cggggctgct | gctgctgctg | 120 |
| ctgctcgctg | ccgcctgcgc | cgtcttcctc | gcctgcccct | gggccgtgtc | cggggctcgc | 180 |
| gcctcgcccg | gctccgcggc | cagcccgaga | ctccgcgagg | gtcccgagct | tcgcccgac | 240 |
| gatcccgccg | gcctcttgga | cctgcggcag | ggcatgtttg | cgcagctggt | ggcccaaaat | 300 |
| gttctgctga | tcgatgggcc | cctgagctgg | tacagtgacc | caggcctggc | aggcgtgtcc | 360 |
| ctgacggggg | gcctgagcta | caaagaggac | acgaaggagc | tggtggtggc | caaggctgga | 420 |
| gtctactatg | tcttctttca | actagagctg | cggcgcgtgg | tggccggcga | gggctcaggc | 480 |
| tccgtttcac | ttgcgctgca | cctgcagcca | ctgcgctctg | ctgctgggc | cgccgccctg | 540 |
| gctttgaccg | tggacctgcc | accgcctcc | tccgaggctc | ggaactcggc | cttcggtttc | 600 |
| cagggccgct | tgctgcacct | gagtgccggc | cagcgcctgg | gcgtccatct | tcacactgag | 660 |
| gccagggcac | gccatgcctg | gcagcttacc | cagggcgcca | cagtcttggg | actcttccgg | 720 |
| gtgaccccg | aaatcccagc | cggactccct | tcaccgaggt | cggaataa | | 768 |

<210> SEQ ID NO 5
<211> LENGTH: 473
<212> TYPE: DNA
<213> ORGANISM: Homo sapiens

<400> SEQUENCE: 5

| | | | | | |
|---|---|---|---|---|---|
| atgtacagga | tgcaactcct | gtcttgcatt | gcactaattc | ttgcacttgt | cacaaacagt | 60 |
| gcacctactt | caagttcgac | aaagaaaaca | aagaaaacac | agctacaact | ggagcattta | 120 |
| ctgctggatt | tacagatgat | tttgaatgga | attaataatt | acaagaatcc | caaactcacc | 180 |
| aggatgctca | catttaagtt | ttacatgccc | aagaaggcca | cagaactgaa | acagcttcag | 240 |
| tgtctagaag | aagaactcaa | acctctggag | gaagtgctga | atttagctca | aagcaaaaac | 300 |
| tttcacttaa | gacccaggga | cttaatcagc | aatatcaacg | taatagttct | ggaactaaag | 360 |
| ggatctgaaa | caacattcat | gtgtgaatat | gcagatgaga | cagcaaccat | tgtagaattt | 420 |
| ctgaacagat | ggattaccct | ttgtcaaagc | atcatctcaa | cactaacttg | ata | 473 |

<210> SEQ ID NO 6
<211> LENGTH: 865
<212> TYPE: DNA
<213> ORGANISM: Homo sapiens

<400> SEQUENCE: 6

| | | | | | |
|---|---|---|---|---|---|
| atgggccaca | cacggaggca | gggaacatca | ccatccaagt | gtccatacct | caatttcttt | 60 |
| cagctcttgg | tgctggctgg | tctttctcac | ttctgttcag | gtgttatcca | cgtgaccaag | 120 |
| gaagtgaaag | aagtggcaac | gctgtcctgt | ggtcacaatg | tttctgttga | agagctggca | 180 |
| caaactcgca | tctactggca | aaaggagaag | aaaatggtgc | tgactatgat | gtctgggac | 240 |
| atgaatatat | ggcccagtac | aagaaccgga | ccatctttga | tatcactaat | aacctctcca | 300 |
| ttgtgatcct | ggctctgcgc | ccatctgacg | agggcacata | cgagtgtgtt | gttctgaagt | 360 |
| atgaaaaaga | cgctttcaag | cgggaacacc | tggctgaagt | gacgttatca | gtcaaagctg | 420 |
| acttccctac | acctagtata | tctgactttg | aaattccaac | ttctaatatt | agaaggataa | 480 |

| | |
|---|---|
| tttgctcaac ctctggaggt tttccagagc ctcacctctc ctggttggaa aatggagaag | 540 |
| aattaaatgc catcaacaca acagtttccc aagatcctga aactgagctc tatgctgtta | 600 |
| gcagaaactg gatttcaata tgacaaccaa ccacagcttc atgtgtctca tcaagtatgg | 660 |
| acatttaaga gtgaatcaga ccttcaactg gaatacaacc aagcaagagc attttcctga | 720 |
| taacctgctc ccatcctggg ccattacctt aatctcagta aatggaattt tgtgatatg | 780 |
| ctgcctgacc tactgctttg ccccaagatg cagagagaga aggaggaatg agagattgag | 840 |
| aagggaaagt gtacgccctg tataa | 865 |

<210> SEQ ID NO 7
<211> LENGTH: 972
<212> TYPE: DNA
<213> ORGANISM: Homo sapiens

<400> SEQUENCE: 7

| | |
|---|---|
| atgggactga gtaacattct ctttgtgatg gccttcctgc tctctggtgc tgctcctctg | 60 |
| aagattcaag cttatttcaa tgagactgca gacctgccat gccaatttgc aaactctcaa | 120 |
| aaccaaagcc tgagtgagct agtagtattt tggcaggacc aggaaaactt ggttctgaat | 180 |
| gaggtatact taggcaaaga gaaatttgac agtgttcatt ccaagtatat gggccgcaca | 240 |
| agttttgatt cggacagttg gaccctgaga cttcacaatc ttcagatcaa ggacaagggc | 300 |
| ttgtatcaat gtatcatcca tcacaaaaag cccacaggaa tgattcgcat ccaccagatg | 360 |
| aattctgaac tgtcagtgct tgctaacttc agtcaacctg aaatagtacc aatttctaat | 420 |
| ataacagaaa atgtgtacat aaatttgacc tgctcatcta tacacggtta cccagaacct | 480 |
| aagaagatga gtgttttgct aagaaccaag aattcaacta tcgagtatga tggtattatg | 540 |
| cagaaatctc aagataatgt cacagaactg tacgacgttt ccatcagctt gtctgtttca | 600 |
| ttccctgatg ttacgagcaa tatgaccatc ttctgtattc tggaaactga caagacgcgg | 660 |
| cttttatctt caccttttctc tatagagctt gaggaccctc agcctccccc agaccacatt | 720 |
| ccttggatta cagctgtact tccaacagtt attatatgtg tgatggtttt ctgtctaatt | 780 |
| ctatggaaat ggaagaagaa gaagcggcct cgcaactctt ataaatgtgg aaccaacaca | 840 |
| atggagaggg aagagagtga acagaccaag aaaagagaaa aaatccatat acctgaaaga | 900 |
| tctgatgaag cccagcgtgt tttttaaaagt tcgaagacat cttcatgcga caaaagtgat | 960 |
| acatgttttt aa | 972 |

<210> SEQ ID NO 8
<211> LENGTH: 11746
<212> TYPE: DNA
<213> ORGANISM: Artificial Sequence
<220> FEATURE:
<223> OTHER INFORMATION: Shuttle for Ad-3
<220> FEATURE:
<221> NAME/KEY: misc_feature
<222> LOCATION: (1)..(11746)
<223> OTHER INFORMATION: "N" = "A", "G", "C" or "T"

<400> SEQUENCE: 8

| | |
|---|---|
| aatgcgccgn nnnnnnnnn nnnnnnnnnn nnnttaatta annntcccctt ccagctctct | 60 |
| gccccttttg gattgaagcc aatatgataa tgagggggtg gagtttgtga cgtgcgcgg | 120 |
| ggcgtgggaa cggggcgggt gacgtagtag tgtggcggaa gtgtgatgtt gcaagtgtgg | 180 |
| cggaacacat gtaagcgacg gatgtggcaa aagtgacgtt tttggtgtgc gccggtgtac | 240 |
| acaggaagtg acaattttcg cgcggtttta ggcggatgtt gtagtaaatt tgggcgtaac | 300 |

-continued

```
cgagtaagat ttggccattt tcgcgggaaa actgaataag aggaagtgaa atctgaataa    360
ttttgtgtta ctcatagcgc gtaannnnta atagtaatca attacggggt cattagttca    420
tagcccatat atggagttcc gcgttacata acttacggta aatggcccgc ctggctgacc    480
gcccaacgac ccccgcccat tgacgtcaat aatgacgtat gttcccatag taacgccaat    540
agggactttc cattgacgtc aatgggtgga gtatttacgg taaactgccc acttggcagt    600
acatcaagtg tatcatatgc caagtacgcc ccctattgac gtcaatgacg gtaaatggcc    660
cgcctggcat tatgcccagt acatgacctt atgggacttt cctacttggc agtacatcta    720
cgtattagtc atcgctatta ccatggtgat gcggttttgg cagtacatca atgggcgtgg    780
atagcggttt gactcacggg gatttccaag tctccacccc attgacgtca atgggagttt    840
gttttggcac caaaatcaac gggactttcc aaaatgtcgt aacaactccg ccccattgac    900
gcaaatgggc ggtaggcgtg tacggtggga ggtctatata agcagagctg gtttagtgaa    960
ccgtcagatc cgctagagat ctggatccga attcgccgcc accatgggtc tcagaagct   1020
aaccatctcc tggtttgcca tcgttttgct ggtgtctcca ctcatggcca tgtgggagct   1080
ggagaaagac gtttatgttg tagaggtgga ctggactccc gatgcccctg agaaacagt   1140
gaacctcacc tgtgacacgc ctgaagaaga tgacatcacc tggaccctcag accagagaca   1200
tggagtcata ggctctggaa agaccctgac catcactgtc aaagagtttc tagatgctgg   1260
ccagtacacc tgccacaaag gaggcgagac tctgagccac tcacatctgc tgctccacaa   1320
gaaggaaaat ggaattggt ccactgaaat tttaaaaaat ttcaaaaaca agactttcct   1380
gaagtgtgaa gcaccaaatt actccggacg gttcacgtgc tcatggctgg tgcaaagaaa   1440
catggacttg aagttcaaca tcaagagcag tagcagttcc cctgactctc gggcagtgac   1500
atgtggaatg gcgtctctgt ctgcagagaa ggtcacactg gaccaaaggg actatgagaa   1560
gtattcagtg tcctgccagg aggatgtcac ctgcccaact gccgaggaga ccctgccat   1620
tgaactggcg ttggaagcac ggcagcagaa taaatatgag aactacagca ccagcttctt   1680
catcagggac atcatcaaac cagacccgcc caagaacttg cagatgaagc ctttgaagaa   1740
ctcacaggtg gaggtcagct gggagtaccc tgactcctgg agcactcccc attcctactt   1800
ctccctcaag ttctttgttc gaatccagcg caagaaagaa aagatgaagg agacagagga   1860
ggggtgtaac cagaaaggtg cgttcctcgt agagaagaca tctaccgaag tccaatgcaa   1920
aggcgggaat gtctgcgtgc aagctcagga tcgctattac aattcctcat gcagcaagtg   1980
ggcatgtgtt ccctgcaggg tccgatccgg tggcggtggc tcgggcggtg gtgggtcggg   2040
tggcggcgga tctagggtca ttccagtctc tggacctgcc aggtgtctta gccagtccg   2100
aaacctgctg aagaccacag atgacatggt gaagacggcc agagaaaagc tgaaacatta   2160
ttcctgcact gctgaagaca tcgatcatga agacatcaca cgggaccaaa ccagcacatt   2220
gaagacctgt ttaccactgg aactacacaa gaacgagagt tgcctggcta ctagagagac   2280
ttcttccaca acaagaggga gctgcctgcc cccacagaag acgtctttga tgatgaccct   2340
gtgccttggt agcatctatg aggacttgaa gatgtaccag acagagttcc aggccatcaa   2400
cgcagcactt cagaatcaca accatcagca gatcattcta gacaagggca tgctggtggc   2460
catcgatgag ctgatgcagt ctctgaatca taatggcgag actctgcgcc agaaacctcc   2520
tgtgggagaa gcagaccctt acagagtgaa aatgaagctc tgcatcctgc ttcacgcctt   2580
cagcacccgc gtcgtgacca tcaacagggg gatgggctat ctgagctccg cctgagaatt   2640
gatccggatt agtccaattt gttaaagaca ggatgaagct taaaacagct ctggggttgt   2700
```

```
acccacccca gaggcccacg tggcggctag tactccggta ttgcggtacc cttgtacgcc    2760
tgttttatac tcccttcccg taacttagac gcacaaaacc aagttcaata gaaggggta     2820 caaaccagta ccaccacgaa caagcacttc tgtttccccg gtgatgtcgt atagactgct    2880
tgcgtggttg aaagcgacgg atccgttatc cgcttatgta cttcgagaag cccagtacca    2940
cctcggaatc ttcgatgcgt tgcgctcagc actcaacccc agagtgtagc ttaggctgat    3000
gagtctggac atccctcacc ggtgacggtg gtccaggctg cgttggcggc ctacctatgg    3060
ctaacgccat gggacgctag ttgtgaacaa ggtgtgaaga gcctattgag ctacataaga    3120
atcctccggc ccctgaatgc ggctaatccc aacctcggag caggtggtca caaaccagtg    3180
attggcctgt cgtaacgcgc aagtccgtgg cggaaccgac tactttgggt gtccgtgttt    3240
ccttttattt tattgtggct gcttatggtg acaatcacag attgttatca taaagcgaat    3300
tggattgcgg ccgcgccacc atggaccagc acacacttga tgtggaggat accgcggatg    3360
ccagacatcc agcaggtact tcgtgcccct cggatgcggc gctcctcaga gatacgggc     3420 tcctcgcgga cgctgcgctc ctctcagata ctgtgcgccc cacaaatgcc gcgctcccca    3480
cggatgctgc ctaccctgcg gttaatgttc gggatcgcga ggccgcgtgg ccgcctgcac    3540
tgaacttctg ttcccgccac ccaaagctct atggcctagt cgctttggtt ttgctgcttc    3600
tgatcgccgc ctgtgttcct atcttcaccc gcaccgagcc tcggccagcg ctcacaatca    3660
ccacctcgcc caacctgggt acccgagaga ataatgcaga ccaggtcacc cctgtttccc    3720
acattggctg ccccaacact acacaacagg gctctcctgt gttcgccaag ctactggcta    3780
aaaaccaagc atcgttgtgc aatacaactc tgaactggca cagccaagat ggagctggga    3840
gctcatacct atctcaaggt ctgaggtacg aagaagacaa aaaggagttg gtggtagaca    3900
gtcccgggct ctactacgta tttttggaac tgaagctcag tccaacattc acaaacacag    3960
gccacaaggt gcagggctgg gtctctcttg ttttgcaagc aaagcctcag gtagatgact    4020
ttgacaactt ggccctgaca gtggaactgt tcccttgctc catggagaac aagttagtgg    4080
accgttcctg gagtcaactg ttgctcctga aggctggcca ccgcctcagt gtgggtctga    4140
gggcttatct gcatggagcc caggatgcat acagagactg ggagctgtct tatcccaaca    4200
ccaccagctt tggactcttt cttgtgaaac ccgacaaccc atgggaatga aactatcct    4260 tcttgtgact ggcgcgcctg atcaatcgat gtttaaacgt tattttccac catattgccg    4320
tcttttggca atgtgagggc ccggaaacct ggccctgtct tcttgacgag cattcctagg    4380
ggtctttccc ctctcgccaa aggaatgcaa ggtctgttga atgtcgtgaa ggaagcagtt    4440
cctctggaag cttcttgaag acaaacaacg tctgtagcga ccctttgcag gcagcggaac    4500
cccccacctg gcgacaggtg cctctgcggc caaaagccac gtgtataaga tacacctgca    4560
aaggcggcac aaccccagtg ccacgttgtg agttggatag ttgtggaaag agtcaaatgg    4620
ctctcctcaa gcgtattcaa caaggggctg aaggatgccc agaaggtacc ccattgtatg    4680
ggatctgatc tggggcctcg gtgcacatgc tttacgtgtg tttagtcgag gttaaaaaaa    4740
cgtctaggcc ccccgaacca cggggacgtg gttttccttt gaaaaacacg attctcgaga    4800
ctagtgccac catgtacagc atgcagctcg catcctgtgt cacattgaca cttgtgctcc    4860
ttgtcaacag cgcaccccact tcaagctcca cttcaagctc tacagcggaa gcacagcagc    4920
agcagcagca gcagcagcag cagcagcagc acctggagca gctgttgatg gacctacagg    4980
agctcctgag caggatggag aattacagga acctgaaact ccccaggatg ctcaccttca    5040
aattttactt gcccaagcag gccacagaat tgaaagatct tcagtgccta gaagatgaac    5100
```

```
ttggacctct gcggcatgtt ctggatttga ctcaaagcaa aagctttcaa ttggaagatg    5160
ctgagaattt catcagcaat atcagagtaa ctgttgtaaa actaaagggc tctgacaaca    5220
catttgagtg ccaattcgat gatgagtcag caactgtggt ggactttctg aggagatgga    5280
tagccttctg tcaaagcatc atctcaacaa gccctcaata actatgtaac gcgtgctagc    5340
atggccggcc gcggccgcgg ccgctcgagc ctaagcttct agataagata tccgatccac    5400
cggatctaga taactgatca taatcagcca taccacattt gtagaggttt tacttgcttt    5460
aaaaaacctc ccacacctcc ccctgaacct gaaacataaa atgaatgcaa ttgttgttgt    5520
taacttgttt attgcagctt ataatggtta caaataaagc aatagcatca caaatttcac    5580
aaataaagca ttttttttcac tgcattctag ttgtggtttg tccaaactca tcaatgtatc    5640
ttaacgcnnn ntaagggtgg gaaagaatat ataaggtggg ggtcttatgt agttttgtat    5700
ctgttttgca gcagccgccg ccgccatgag caccaactcg tttgatggaa gcattgtgag    5760
ctcatatttg acaacgcgca tgcccccatg ggccggggtg cgtcagaatg tgatgggctc    5820
cagcattgat ggtcgccccg tcctgcccgc aaactctact accttgacct acgagaccgt    5880
gtctggaacg ccgttggaga ctgcagcctc cgccgccgct tcagccgctg cagccaccgc    5940
ccgcgggatt gtgactgact ttgctttcct gagcccgctt gcaagcagtg cagcttcccg    6000
ttcatccgcc cgcgatgaca agttgacggc tcttttggca caattggatt ctttgacccg    6060
ggaacttaat gtcgtttctc agcagctgtt ggatctgcgc cagcaggttt ctgccctgaa    6120
ggcttcctcc cctcccaatg cggtttaaaa cataaataaa aaaccagact ctgtttggat    6180
ttggatcaag caagtgtctt gctgtctta tttaggggtt ttgcgcgcgc ggtaggcccg    6240
ggaccagcgg tctcggtcgt tgagggtcct gtgtatttttt tccaggacgt ggtaaaggtg    6300
actctggatg ttcagataca tgggcataag cccgtctctg gggtggaggt agcaccactg    6360
cagagcttca tgctgcgggg tggtgttgta gatgatccag tcgtagcagg agcgctgggc    6420
gtggtgccta aaaatgtctt tcagtagcaa gctgattgcc aggggcaggc ccttggtgta    6480
agtgtttaca aagcggttaa gctgggatgg gtgcatacgt ggggatatga gatgcatctt    6540
ggactgtatt tttaggttgg ctatgttccc agccatatcc ctccggggat tcatgttgtg    6600
cagaaccacc agcacagtgt atccggtgca cttgggaaat ttgtcatgta gcttagaagg    6660
aaatgcgtgg aagaacttgg agacgccctt gtgacctcca agattttcca tgcattcgtc    6720
cataatgatg gcaatgggcc cacgggcggc ggcctgggcg aagatatttc tgggatcact    6780
aacgtcatag ttgtgttcca ggatgagatc gtcataggcc attttttacaa agcgcgggcg    6840 gagggtgcca gactgcggta taatggttcc atccggccca ggggcgtagt taccctcaca    6900
gatttgcatt tccacgcctt tgagttcaga tgggggatc atgtctacct gcggggcgat    6960
gaagaaaacg gtttccgggg taggggagat cagctgggaa gaaagcaggt tcctgagcag    7020
ctgcgactta ccgcagccgg tgggcccgta aatcacacct attaccgggt gcaactggta    7080
gttaagagag ctgcagctgc cgtcatccct gagcaggggg gccacttcgt taagcatgtc    7140
cctgactcgc atgttttccc tgaccaaatc cgccagaagg cgctcgccgc ccagcgatag    7200
cagttcttgc aaggaagcaa agttttttcaa cggtttgaga ccgtccgccg taggcatgct    7260
tttgagcgtt tgaccaagca gttccaggcg gtcccacagc tcggtcacct gctctacggc    7320
atctcgatcc agcatatctc ctcgtttcgc gggttggggc ggctttcgct gtacggcagt    7380
agtcggtgct cgtccagacg ggccagggtc atgtctttcc acgggcgcag gtcctcgtc    7440 agcgtagtct gggtcacggt gaaggggtgc gctccgggct gcgcgctggc cagggtgcgc    7500
```

```
ttgaggctgg tcctgctggt gctgaagcgc tgccggtctt cgccctgcgc gtcggccagg    7560
tagcatttga ccatggtgtc atagtccagc ccctccgcgg cgtggccctt ggcgcgcagc    7620
ttgcccttgg aggaggcgcc gcacgagggg cagtgcagac ttttgagggc gtagagcttg    7680
ggcgcgagaa ataccgattc cggggagtag gcatccgcgc cgcaggcccc gcagacggtc    7740
tcgcattcca cgagccaggt gagctctggc cgttcggggt caaaaaccag gtttccccca    7800 tgcttttga tgcgtttctt acctctggtt tccatgagcc ggtgtccacg ctcggtgacg      7860
aaaaggctgt ccgtgtcccc gtatacagac tnnngtttaa acgaattcnn natataaaat    7920
gcaaggtgct gctcaaaaaa tcaggcaaag cctcgcgcaa aaagaaagc acatcgtagt    7980 catgctcatg cagataaagg caggtaagct ccggaaccac cacagaaaaa gacaccattt    8040
ttctctcaaa catgtctgcg ggtttctgca taaacacaaa ataaaataac aaaaaaacat    8100
ttaaacatta gaagcctgtc ttacaacagg aaaaacaacc cttataagca taagacggac    8160 tacgccatg ccggcgtgac cgtaaaaaaa ctggtcaccg tgattaaaaa gcaccaccga      8220
cagctcctcg gtcatgtccg gagtcataat gtaagactcg gtaaacacat caggttgatt    8280
catcggtcag tgctaaaaag cgaccgaaat agcccggggg aatacatacc cgcaggcgta    8340
gagacaacat tacagccccc ataggaggta taacaaaatt aataggagag aaaaacacat    8400
aaacacctga aaaaccctcc tgcctaggca aaatagcacc ctcccgctcc agaacaacat    8460
acagcgcttc acagcggcag cctaacagtc agccttacca gtaaaaaaga aaacctatta    8520
aaaaaacacc actcgacacg gcaccagctc aatcagtcac agtgtaaaaa agggccaagt    8580
gcagagcgag tatatatagg actaaaaaat gacgtaacgg ttaaagtcca caaaaaacac    8640
ccagaaaacc gcacgcgaac ctacgcccag aaacgaaagc caaaaaaccc acaacttcct    8700
caaatcgtca cttccgtttt cccacgttac gtaacttccc attttaagaa aactacaatt    8760
cccaacacat acaagttact ccgccctaaa acctacgtca cccgccccgt tcccacgccc    8820
cgcgccacgt cacaaactcc acccccctcat tatcatattg gcttcaatcc aaaataaggt    8880
atattattga tgatnnntta attaaggatc cnnncggtgt gaaataccgc acagatgcgt    8940
aaggagaaaa taccgcatca ggcgctcttc cgcttcctcg ctcactgact cgctgcgctc    9000
ggtcgttcgg ctgcggcgag cggtatcagc tcactcaaag gcggtaatac ggttatccac    9060
agaatcaggg gataacgcag gaaagaacat gtgagcaaaa ggccagcaaa aggccaggaa    9120
ccgtaaaaag gccgcgttgc tggcgttttt ccataggctc cgcccccctg acgagcatca    9180
caaaaatcga cgctcaagtc agaggtggcg aaacccgaca ggactataaa gataccaggc    9240
gtttccccct ggaagctccc tcgtgcgctc tcctgttccg accctgccgc ttaccggata    9300
cctgtccgcc tttctccctt cgggaagcgt ggcgctttct catagctcac gctgtaggta    9360
tctcagttcg gtgtaggtcg ttcgctccaa gctgggctgt gtgcacgaac cccccgttca    9420
gcccgaccgc tgcgccttat ccggtaacta tcgtcttgag tccaacccgg taagacacga    9480
cttatcgcca ctggcagcag ccactggtaa caggattagc agagcgaggt atgtaggcgg    9540
tgctacagag ttcttgaagt ggtggcctaa ctacggctac actagaagga cagtatttgg    9600
tatctgcgct ctgctgaagc cagttacctt cggaaaaaga gttggtagct cttgatccgg    9660
caaacaaacc accgctggta gcggtggttt ttttgtttgc aagcagcaga ttacgcgcag    9720
aaaaaaagga tctcaagaag atcctttgat cttttctacg gggtctgacg ctcagtggaa    9780
cgaaaactca cgttaaggga ttttggtcat gagattatca aaaaggatct tcacctagat    9840 cctttttaaat taaaaatgaa gttttaaatc aatctaaagt atatatgagt aaacttggtc    9900
```

```
tgacagttac caatgcttaa tcagtgaggc acctatctca gcgatctgtc tatttcgttc    9960
atccatagtt gcctgactcc ccgtcgtgta gataactacg atacgggagg gcttaccatc   10020
tggcccccagt gctgcaatga taccgcgaga cccacgctca ccggctccag atttatcagc  10080
aataaaccag ccagccggaa gggccgagcg cagaagtggt cctgcaactt tatccgcctc   10140
catccagtct attaattgtt gccgggaagc tagagtaagt agttcgccag ttaatagttt   10200
gcgcaacgtt gttgnnnnaa aaaggatctt cacctagatc cttttcacgt agaaagccag   10260
tccgcagaaa cggtgctgac cccggatgaa tgtcagctac tgggctatct ggacaaggga   10320
aaacgcaagc gcaaagagaa agcaggtagc ttgcagtggg cttacatggc gatagctaga   10380
ctgggcggtt ttatggacag caagcgaacc ggaattgcca gctggggcgc cctctggtaa   10440
ggttgggaag ccctgcaaag taaactggat ggctttctcg ccgccaagga tctgatggcg   10500
caggggatca agctctgatc aagagacagg atgaggatcg tttcgcatga ttgaacaaga   10560
tggattgcac gcaggttctc cggccgcttg ggtggagagg ctattcggct atgactgggc   10620
acaacagaca atcggctgct ctgatgccgc cgtgttccgg ctgtcagcgc aggggcgccc   10680
ggttcttttt gtcaagaccg acctgtccgg tgccctgaat gaactgcaag acgaggcagc   10740
gcggctatcg tggctggcca cgacgggcgt tccttgcgca gctgtgctcg acgttgtcac   10800
tgaagcggga agggactggc tgctattggg cgaagtgccg gggcaggatc tcctgtcatc   10860
tcaccttgct cctgccgaga agtatccat catggctgat gcaatgcggc ggctgcatac   10920
gcttgatccg gctacctgcc cattcgacca ccaagcgaaa catcgcatcg agcgagcacg   10980
tactcggatg gaagccggtc ttgtcgatca ggatgatctg gacgaagagc atcagggct    11040
cgcgccagcc gaactgttcg ccaggctcaa ggcgagcatg cccgacgcg aggatctcgt    11100
cgtgacccat ggcgatgcct gcttgccgaa tatcatggtg gaaaatggcc gcttttctgg   11160
attcatcgac tgtggccggc tgggtgtggc ggaccgctat caggacatag cgttggctac   11220
ccgtgatatt gctgaagagc ttggcggcga atgggctgac cgcttcctcg tgctttacgg   11280
tatcgccgct cccgattcgc agcgcatcgc cttctatcgc cttcttgacg agttcttctg   11340
aattttgtta aattttttgt taaatcagct cattttttaa ccaataggcc gaaatcggca   11400
acatccctta taaatcaaaa gaatagaccg cgatagggtt gagtgttgtt ccagtttgga   11460
acaagagtcc actattaaag aacgtggact ccaacgtcaa agggcgaaaa accgtctatc   11520
agggcgatgg cccactacgt gaaccatcac ccaaatcaag ttttttgcgg tcgaggtgcc   11580
gtaaagctct aaatcggaac cctaaaggga gcccccgatt tagagcttga cggggaaagc   11640
cggcgaacgt ggcgagaaag gaagggaaga agcgaaagg agcgggcgct agggcgctgg   11700
caagtgtagc ggtcacgctg cgcgtaacca ccacacccgc gcgctt                  11746
```

<210> SEQ ID NO 9  
<211> LENGTH: 10633  
<212> TYPE: DNA  
<213> ORGANISM: Artificial Sequence  
<220> FEATURE:  
<223> OTHER INFORMATION: Shuttle for Ad-2  
<220> FEATURE:  
<221> NAME/KEY: misc_feature  
<222> LOCATION: (1)..(10633)  
<223> OTHER INFORMATION: "N" = "A", "C", "G" or "T"

<400> SEQUENCE: 9

```
aatgcgccgn nnnnnnnnn nnnnnnnnnn nnnttaatta annntcccttt ccagctctct    60
gcccctttg gattgaagcc aatatgataa tgaggggtg gagtttgtga cgtggcgcgg    120
```

-continued

| | |
|---|---|
| ggcgtgggaa cggggcgggt gacgtagtag tgtggcggaa gtgtgatgtt gcaagtgtgg | 180 |
| cggaacacat gtaagcgacg gatgtggcaa aagtgacgtt tttggtgtgc gccggtgtac | 240 |
| acaggaagtg acaattttcg cgcggtttta ggcggatgtt gtagtaaatt tgggcgtaac | 300 |
| cgagtaagat ttggccattt tcgcgggaaa actgaataag aggaagtgaa atctgaataa | 360 |
| ttttgtgtta ctcatagcgc gtaannnnta atagtaatca attacggggt cattagttca | 420 |
| tagcccatat atggagttcc gcgttacata acttacggta aatggcccgc ctggctgacc | 480 |
| gcccaacgac ccccgcccat tgacgtcaat aatgacgtat gttcccatag taacgccaat | 540 |
| agggactttc cattgacgtc aatgggtgga gtatttacgg taaactgccc acttggcagt | 600 |
| acatcaagtg tatcatatgc caagtacgcc ccctattgac gtcaatgacg gtaaatggcc | 660 |
| cgcctggcat tatgcccagt acatgacctt atgggacttt cctacttggc agtacatcta | 720 |
| cgtattagtc atcgctatta ccatggtgat gcggttttgg cagtacatca atgggcgtgg | 780 |
| atagcggttt gactcacggg gatttccaag tctccacccc attgacgtca atgggagttt | 840 |
| gttttggcac caaaatcaac gggactttcc aaaatgtcgt aacaactccg ccccattgac | 900 |
| gcaaatgggc ggtaggcgtg tacggtggga ggtctatata agcagagctg tttagtgaa | 960 |
| ccgtcagatc cgctagagat ctggatccga attcgccgcc accatgggtc ctcagaagct | 1020 |
| aaccatctcc tggtttgcca tcgttttgct ggtgtctcca ctcatggcca tgtgggagct | 1080 |
| ggagaaagac gtttatgttg tagaggtgga ctggactccc gatgcccctg agaaacagt | 1140 |
| gaacctcacc tgtgacacgc ctgaagaaga tgacatcacc tggaccctcag accagagaca | 1200 |
| tggagtcata ggctctggaa agaccctgac catcactgtc aaagagtttc tagatgctgg | 1260 |
| ccagtacacc tgccacaaag gaggcgagac tctgagccac tcacatctgc tgctccacaa | 1320 |
| gaaggaaaat ggaatttggt ccactgaaat tttaaaaaat ttcaaaaaca agactttcct | 1380 |
| gaagtgtgaa gcaccaaatt actccggacg gttcacgtgc tcatggctgg tgcaaagaaa | 1440 |
| catggacttg aagttcaaca tcaagagcag tagcagttcc cctgactctc gggcagtgac | 1500 |
| atgtggaatg cgtctctgt ctgcagagaa ggtcacactg gaccaaaggg actatgagaa | 1560 |
| gtattcagtg tcctgccagg aggatgtcac ctgcccaact gccgaggaga ccctgcccat | 1620 |
| tgaactggcg ttggaagcac ggcagcagaa taaatatgag aactacagca ccagcttctt | 1680 |
| catcagggac atcatcaaac cagacccgcc caagaacttg cagatgaagc ctttgaagaa | 1740 |
| ctcacaggtg gaggtcagct gggagtaccc tgactcctgg agcactcccc attcctactt | 1800 |
| ctccctcaag ttctttgttc gaatccagcg caagaaagaa aagatgaagg agacagagga | 1860 |
| ggggtgtaac cagaaaggtg cgttcctcgt agagaagaca tctaccgaag tccaatgcaa | 1920 |
| aggcgggaat gtctgcgtgc aagctcagga tcgctattac aattcctcat gcagcaagtg | 1980 |
| ggcatgtgtt ccctgcaggg tccgatccgg tggcggtggc tcgggcggtg gtgggtcggg | 2040 |
| tggcggcgga tctagggtca ttccagtctc tggacctgcc aggtgtcta gccagtcccg | 2100 |
| aaacctgctg aagaccacag atgacatggt gaagacggcc agagaaaagc tgaaacatta | 2160 |
| ttcctgcact gctgaagaca tcgatcatga agacatcaca cgggaccaaa ccagcacatt | 2220 |
| gaagacctgt ttaccactgg aactacacaa gaacgagagt tgcctggcta ctagagagac | 2280 |
| ttcttccaca acaagaggga gctgcctgcc cccacagaag acgtctttga tgatgaccct | 2340 |
| gtgccttggt agcatctatg aggacttgaa gatgtaccag acagagttcc aggccatcaa | 2400 |
| cgcagcactt cagaatcaca accatcagca gatcattcta acaagggca tgctggtggc | 2460 |
| catcgatgag ctgatgcagt ctctgaatca taatggcgag actctgcgcc agaaacctcc | 2520 |

```
tgtgggagaa gcagacccct tacagagtgaa aatgaagctc tgcatcctgc ttcacgcctt    2580
cagcacccgc gtcgtgacca tcaacagggt gatgggctat ctgagctccg cctgagaatt    2640
gatccggatt agtccaattt gttaaagaca ggatgaagct taaaacagct ctggggttgt    2700
acccacccca gaggcccacg tggcggctag tactccggta ttgcggtacc cttgtacgcc    2760
tgttttatac tcccttcccg taacttagac gcacaaaacc aagttcaata gaaggggta    2820 caaaccagta ccaccacgaa caagcacttc tgtttccccg gtgatgtcgt atagactgct    2880
tgcgtggttg aaagcgacgg atccgttatc cgcttatgta cttcgagaag cccagtacca    2940
cctcggaatc ttcgatgcgt tgcgctcagc actcaacccc agagtgtagc ttaggctgat    3000
gagtctggac atccctcacc ggtgacggtg gtccaggctg cgttggcggc ctacctatgg    3060
ctaacgccat gggacgctag ttgtgaacaa ggtgtgaaga gcctattgag ctacataaga    3120
atcctccggc ccctgaatgc ggctaatccc aacctcggag caggtggtca caaaccagtg    3180
attggcctgt cgtaacgcgc aagtccgtgg cggaaccgac tactttgggt gtccgtgttt    3240
ccttttattt tattgtggct gcttatggtg acaatcacag attgttatca taaagcgaat    3300
tggattgcgg ccgcgccacc atggaccagc acacacttga tgtggaggat accgcggatg    3360
ccagacatcc agcaggtact tcgtgcccct cggatgcggc gctcctcaga gataccgggc    3420
tcctcgcgga cgctgcgctc ctctcagata ctgtgcgccc cacaaatgcc gcgctcccca    3480
cggatgctgc ctaccctgcg gttaatgttc gggatcgcga ggccgcgtgg ccgcctgcac    3540
tgaacttctg ttcccgccac ccaaagctct atggcctagt cgctttggtt ttgctgcttc    3600
tgatcgccgc ctgtgttcct atcttcaccc gcaccgagcc tcggccagcg ctcacaatca    3660
ccacctcgcc caacctgggt acccgagaga ataatgcaga ccaggtcacc cctgtttccc    3720
acattggctg ccccaacact acacaacagg gctctcctgt gttcgccaag ctactggcta    3780
aaaaccaagc atcgttgtgc aatacaactc tgaactggca cagccaagat ggagctggga    3840
gctcatacct atctcaaggt ctgaggtacg aagaagacaa aaaggagttg gtggtagaca    3900
gtcccgggct ctactacgta tttttggaac tgaagctcag tccaacattc acaaacacag    3960
gccacaaggt gcagggctgg gtctctcttg ttttgcaagc aaaagcctcag gtagatgact    4020 ttgacaactt ggccctgaca gtggaactgt tcccttgctc catggagaac aagttagtgg    4080
accgttcctg gagtcaactg ttgctcctga aggctggcca ccgcctcagt gtgggtctga    4140
gggcttatct gcatggagcc caggatgcat acagagactg ggagctgtct tatcccaaca    4200
ccaccagctt tggactcttt cttgtgaaac ccgacaaccc atgggaatga aactatcct    4260 tcttgtgact ggcgcgatcc gatccaccgg atctagataa ctgatcataa tcagccatac    4320
cacatttgta gaggttttac ttgctttaaa aaacctccca cacctccccc tgaacctgaa    4380
acataaaatg aatgcaattg ttgttgttaa cttgtttatt gcagcttata atggttacaa    4440
ataaagcaat agcatcacaa atttcacaaa taaagcattt ttttcactgc attctagttg    4500
tggtttgtcc aaactcatca atgtatctta acgcnnnnta agggtgggaa agaatatata    4560
aggtgggggt cttatgtagt tttgtatctg ttttgcagca gccgccgccg ccatgagcac    4620
caactcgttt gatggaagca ttgtgagctc atatttgaca acgcgcatgc ccccatgggc    4680
cggggtgcgt cagaatgtga tgggctccag cattgatggt cgccccgtcc tgcccgcaaa    4740
ctctactacc ttgacctacg agaccgtgtc tggaacgccg ttggagactg cagcctccgc    4800
cgccgcttca gccgctgcag ccaccgcccg cgggattgtg actgactttg ctttcctgag    4860
cccgcttgca agcagtgcag cttcccgttc atccgcccgc gatgacaagt tgacggctct    4920
```

```
tttggcacaa ttggattctt tgacccggga acttaatgtc gtttctcagc agctgttgga    4980
tctgcgccag caggtttctg ccctgaaggc ttcctcccct cccaatgcgg tttaaaacat    5040
aaataaaaaa ccagactctg tttggatttg gatcaagcaa gtgtcttgct gtctttattt    5100
aggggttttg cgcgcgcggt aggcccggga ccagcggtct cggtcgttga gggtcctgtg    5160
tatttttcc aggacgtggt aaaggtgact ctggatgttc agatacatgg gcataagccc    5220
gtctctgggg tggaggtagc accactgcag agcttcatgc tgcggggtgg tgttgtagat    5280
gatccagtcg tagcaggagc gctgggcgtg gtgcctaaaa atgtctttca gtagcaagct    5340
gattgccagg ggcaggccct tggtgtaagt gtttacaaag cggttaagct gggatgggtg    5400
catacgtggg gatatgagat gcatcttgga ctgtattttt aggttggcta tgttcccagc    5460
catatccctc cggggattca tgttgtgcag aaccaccagc acagtgtatc cggtgcactt    5520
gggaaatttg tcatgtagct tagaaggaaa tgcgtggaag aacttggaga cgcccttgtg    5580
acctccaaga ttttccatgc attcgtccat aatgatggca atgggcccac gggcggcggc    5640
ctgggcgaag atatttctgg gatcactaac gtcatagttg tgttccagga tgagatcgtc    5700
ataggccatt tttacaaagc gcgggcgag ggtgccagac tgcggtataa tggttccatc    5760
cggcccaggg gcgtagttac cctcacagat ttgcatttcc cacgctttga gttcagatgg    5820
ggggatcatg tctacctgcg gggcgatgaa gaaaacggtt tccggggtag gggagatcag    5880
ctgggaagaa agcaggttcc tgagcagctg cgacttaccg cagccggtgg gcccgtaaat    5940
cacacctatt accgggtgca actggtagtt aagagagctg cagctgccgt catccctgag    6000
caggggggcc acttcgttaa gcatgtccct gactcgcatg ttttccctga ccaaatccgc    6060
cagaaggcgc tcgccgccca gcgatagcag ttcttgcaag gaagcaaagt ttttcaacgg    6120
tttgagaccg tccgccgtag gcatgctttt gagcgtttga ccaagcagtt ccaggcggtc    6180
ccacagctcg gtcacctgct ctacggcatc tcgatccagc atatctcctc gtttcgcggg    6240
ttggggcggc tttcgctgta cggcagtagt cggtgctcgt ccagacgggc cagggtcatg    6300
tcttccacg ggcgcagggt cctcgtcagc gtagtctggg tcacggtgaa ggggtgcgct    6360
ccgggctgcg cgctggccag ggtgcgcttg aggctggtcc tgctggtgct gaagcgctgc    6420
cggtcttcgc cctgcgcgtc ggccaggtag catttgacca tggtgtcata gtccagcccc    6480
tccgcggcgt ggcccttggc gcgcagcttg cccttggagg aggcgccgca cgaggggcag    6540
tgcagacttt tgagggcgta gagcttgggc gcgagaaata ccgattccgg ggagtaggca    6600
tccgcgccgc aggcccccgca gacggtctcg cattccacga gccaggtgag ctctggccgt    6660
tcggggtcaa aaaccaggtt tcccccatgc tttttgatgc gtttcttacc tctggtttcc    6720
atgagccggt gtccacgctc ggtgacgaaa aggctgtccg tgtccccgta tacagactnn    6780
ngtttaaacg aattcnnnat ataaaatgca aggtgctgct caaaaaatca ggcaaagcct    6840
cgcgcaaaaa agaaagcaca tcgtagtcat gctcatgcag ataaaggcag gtaagctccg    6900
gaaccaccac agaaaaagac accatttttc tctcaaacat gtctgcgggt ttctgcataa    6960
acacaaaata aaataacaaa aaacattta aacattagaa gcctgtctta caacaggaaa    7020
aacaacccttt ataagcataa gacggactac ggccatgccg gcgtgaccgt aaaaaaactg    7080
gtcaccgtga ttaaaagca ccaccgacag ctcctcggtc atgtccggag tcataatgta    7140
agactcggta aacacatcag gttgattcat cggtcagtgc taaaaagcga ccgaaatagc    7200
ccgggggaat acatacccgc aggcgtagag acaacattac agccccata ggaggtataa    7260
caaaattaat aggagagaaa aacacataaa cacctgaaaa accctcctgc ctaggcaaaa    7320
```

```
tagcaccctc ccgctccaga acaacataca gcgcttcaca gcggcagcct aacagtcagc   7380
cttaccagta aaaagaaaaa cctattaaaa aaacaccact cgacacggca ccagctcaat   7440
cagtcacagt gtaaaaaagg gccaagtgca gagcgagtat atataggact aaaaaatgac   7500
gtaacggtta aagtccacaa aaaacaccca gaaaaccgca cgcgaaccta cgcccagaaa   7560
cgaaagccaa aaacccaca acttcctcaa atcgtcactt ccgttttccc acgttacgta    7620
acttcccatt ttaagaaaac tacaattccc aacacataca agttactccg ccctaaaacc   7680
tacgtcaccc gccccgttcc cacgcccgc gccacgtcac aaactccacc ccctcattat    7740
catattggct tcaatccaaa ataaggtata ttattgatga tnnnttaatt aaggatccnn   7800
ncggtgtgaa ataccgcaca gatgcgtaag gagaaaatac cgcatcaggc gctcttccgc   7860
ttcctcgctc actgactcgc tgcgctcggt cgttcggctg cggcgagcgg tatcagctca   7920
ctcaaaggcg gtaatacggt tatccacaga atcagggat aacgcaggaa agaacatgtg    7980
agcaaaaggc cagcaaaagg ccaggaaccg taaaaaggcc gcgttgctgg cgttttccca   8040
taggctccgc cccctgacg agcatcacaa aaatcgacgc tcaagtcaga ggtggcgaaa    8100
cccgacagga ctataaagat accaggcgtt tccccctgga agctccctcg tgcgctctcc   8160
tgttccgacc ctgccgctta ccggatacct gtccgccttt ctcccttcgg gaagcgtggc   8220
gctttctcat agctcacgct gtaggtatct cagttcggtg taggtcgttc gctccaagct   8280
gggctgtgtg cacgaacccc ccgttcagcc cgaccgctgc gccttatccg gtaactatcg   8340
tcttgagtcc aacccggtaa gacacgactt atcgccactg gcagcagcca ctggtaacag   8400
gattagcaga gcgaggtatg taggcggtgc tacagagttc ttgaagtggt ggcctaacta   8460
cggctacact agaaggacag tatttggtat ctgcgctctg ctgaagccag ttaccttcgg   8520
aaaaagagtt ggtagctctt gatccggcaa acaaaccacc gctggtagcg gtggtttttt   8580
tgtttgcaag cagcagatta cgcgcagaaa aaaaggatct caagaagatc ctttgatctt   8640
ttctacgggg tctgacgctc agtggaacga aaactcacgt taagggattt tggtcatgag   8700
attatcaaaa aggatcttca cctagatcct tttaaattaa aaatgaagtt ttaaatcaat   8760
ctaaagtata tatgagtaaa cttggtctga cagttaccaa tgcttaatca gtgaggcacc   8820
tatctcagcg atctgtctat ttcgttcatc catagttgcc tgactccccg tcgtgtagat   8880
aactacgata cgggagggct taccatctgg ccccagtgct gcaatgatac cgcgagaccc   8940
acgctcaccg gctccagatt tatcagcaat aaaccagcca gccggaaggg ccgagcgcag   9000
aagtggtcct gcaactttat ccgcctccat ccagtctatt aattgttgcc gggaagctag   9060
agtaagtagt tcgccagtta atagtttgcg caacgttgtt gnnnnaaaaa ggatcttcac   9120
ctagatcctt ttcacgtaga aagccagtcc gcagaaacgg tgctgacccc ggatgaatgt   9180
cagctactgg gctatctgga caagggaaaa cgcaagcgca aagagaaagc aggtagcttg   9240
cagtgggctt acatggcgat agctagactg ggcggtttta tggacagcaa gcgaaccgga   9300
attgccagct ggggcgccct ctggtaaggt tgggaagccc tgcaaagtaa actggatggc   9360
tttctcgccg ccaaggatct gatggcgcag gggatcaagc tctgatcaag agacaggatg   9420
aggatcgttt cgcatgattg aacaagatgg attgcacgca ggttctccgg ccgcttgggt   9480
ggagaggcta ttcggctatg actgggcaca acagacaatc ggctgctctg atgccgccgt   9540
gttccggctg tcagcgcagg ggcgcccggt tcttttttgtc aagaccgacc tgtccggtgc   9600
cctgaatgaa ctgcaagacg aggcagcgcg gctatcgtgg ctggccacga cgggcgttcc   9660
ttgcgcagct gtgctcgacg ttgtcactga agcgggaagg gactggctgc tattgggcga   9720
```

```
agtgccgggg caggatctcc tgtcatctca ccttgctcct gccgagaaag tatccatcat    9780
ggctgatgca atgcggcggc tgcatacgct tgatccggct acctgcccat tcgaccacca    9840
agcgaaacat cgcatcgagc gagcacgtac tcggatggaa gccggtcttg tcgatcagga    9900
tgatctggac gaagagcatc aggggctcgc gccagccgaa ctgttcgcca ggctcaaggc    9960
gagcatgccc gacggcgagg atctcgtcgt gacccatggc gatgcctgct tgccgaatat   10020
catggtggaa aatggccgct tttctggatt catcgactgt ggccggctgg gtgtggcgga   10080
ccgctatcag gacatagcgt tggctacccg tgatattgct gaagagcttg gcggcgaatg   10140
ggctgaccgc ttcctcgtgc tttacggtat cgccgctccc gattcgcagc gcatcgcctt   10200
ctatcgcctt cttgacgagt tcttctgaat tttgttaaaa ttttgttaa atcagctcat   10260 tttttaacca ataggccgaa atcggcaaca tcccttataa atcaaaagaa tagaccgcga   10320
tagggttgag tgttgttcca gtttggaaca agagtccact attaaagaac gtggactcca   10380
acgtcaaagg gcgaaaaacc gtctatcagg gcgatggccc actacgtgaa ccatcaccca   10440
aatcaagttt tttgcggtcg aggtgccgta aagctctaaa tcggaaccct aaagggagcc   10500
cccgatttag agcttgacgg ggaaagccgg cgaacgtggc gagaaaggaa gggaagaaag   10560
cgaaaggagc gggcgctagg gcgctggcaa gtgtagcggt cacgctgcgc gtaaccacca   10620
cacccgcgcg ctt                                                      10633

<210> SEQ ID NO 10
<211> LENGTH: 9049
<212> TYPE: DNA
<213> ORGANISM: Artificial Sequence
<220> FEATURE:
<223> OTHER INFORMATION: Shuttle for Ad-1
<220> FEATURE:
<221> NAME/KEY: misc_feature
<222> LOCATION: (1)..(9049)
<223> OTHER INFORMATION: "N" = "A", "C", "G" or "T"

<400> SEQUENCE: 10
aatgcgccgn nnnnnnnnn nnnnnnnnnn nnnttaatta annntcccctt ccagctctct      60 gccccttttg gattgaagcc aatatgataa tgaggggggtg gagtttgtga cgtggcgcgg   120
ggcgtgggaa cggggcgggt gacgtagtag tgtggcggaa gtgtgatgtt gcaagtgtgg   180
cggaacacat gtaagcgacg gatgtggcaa aagtgacgtt tttggtgtgc gccggtgtac   240
acaggaagtg acaattttcg cgcggtttta ggcggatgtt gtagtaaatt tgggcgtaac   300
cgagtaagat ttggccatttt tcgcgggaaa actgaataag aggaagtgaa atctgaataa   360
ttttgtgtta ctcatagcgc gtaannnnta atagtaatca attacggggt cattagttca   420
tagcccatat atggagttcc gcgttacata acttacggta aatggcccgc ctggctgacc   480
gcccaacgac ccccgcccat tgacgtcaat aatgacgtat gttcccatag taacgccaat   540
agggactttc cattgacgtc aatgggtgga gtatttacgg taaactgccc acttggcagt   600
acatcaagtg tatcatatgc caagtacgcc ccctattgac gtcaatgacg gtaaatggcc   660
cgcctggcat tatgcccagt acatgacctt atgggacttt cctacttggc agtacatcta   720
cgtattagtc atcgctatta ccatggtgat gcggttttgg cagtacatca atgggcgtgg   780
atagcggttt gactcacggg gatttccaag tctccacccc attgacgtca atgggagttt   840
gttttggcac caaaatcaac gggactttcc aaaatgtcgt aacaactccg ccccattgac   900
gcaaatgggc ggtaggcgtg tacggtggga ggtctatata agcagagctg tttagtgaa   960 ccgtcagatc cgctagagat ctggatccga attcgccgcc accatgggtc ctcagaagct   1020
```

-continued

| | | | | | |
|---|---|---|---|---|---|
| aaccatctcc | tggttttgcca | tcgttttgct | ggtgtctcca | ctcatggcca | tgtgggagct | 1080 |
| ggagaaagac | gtttatgttg | tagaggtgga | ctggactccc | gatgccctg | gagaaacagt | 1140 |
| gaacctcacc | tgtgacacgc | ctgaagaaga | tgacatcacc | tggacctcag | accagagaca | 1200 |
| tggagtcata | ggctctggaa | agaccctgac | catcactgtc | aaagagtttc | tagatgctgg | 1260 |
| ccagtacacc | tgccacaaag | gaggcgagac | tctgagccac | tcacatctgc | tgctccacaa | 1320 |
| gaaggaaaat | ggaatttggt | ccactgaaat | tttaaaaaat | ttcaaaaaca | agactttcct | 1380 |
| gaagtgtgaa | gcaccaaatt | actccggacg | gttcacgtgc | tcatggctgg | tgcaaagaaa | 1440 |
| catggacttg | aagttcaaca | tcaagagcag | tagcagttcc | cctgactctc | gggcagtgac | 1500 |
| atgtggaatg | gcgtctctgt | ctgcagagaa | ggtcacactg | gaccaaaggg | actatgagaa | 1560 |
| gtattcagtg | tcctgccagg | aggatgtcac | ctgcccaact | gccgaggaga | ccctgcccat | 1620 |
| tgaactggcg | ttggaagcac | ggcagcagaa | taaatatgag | aactacagca | ccagcttctt | 1680 |
| catcagggac | atcatcaaac | cagacccgcc | caagaacttg | cagatgaagc | ctttgaagaa | 1740 |
| ctcacaggtg | gaggtcagct | gggagtaccc | tgactcctgg | agcactcccc | attcctactt | 1800 |
| ctccctcaag | ttctttgttc | gaatccagcg | caagaaagaa | aagatgaagg | agacagagga | 1860 |
| ggggtgtaac | cagaaaggtg | cgttcctcgt | agagaagaca | tctaccgaag | tccaatgcaa | 1920 |
| aggcgggaat | gtctgcgtgc | aagctcagga | tcgctattac | aattcctcat | gcagcaagtg | 1980 |
| ggcatgtgtt | ccctgcaggg | tccgatccgg | tggcggtggc | tcgggcggtg | gtgggtcggg | 2040 |
| tggcggcgga | tctagggtca | ttccagtctc | tggacctgcc | aggtgtctta | gccagtcccg | 2100 |
| aaacctgctg | aagaccacag | atgacatggt | gaagacggcc | agagaaaagc | tgaaacatta | 2160 |
| ttcctgcact | gctgaagaca | tcgatcatga | agacatcaca | cgggaccaaa | ccagcacatt | 2220 |
| gaagacctgt | ttaccactgg | aactacacaa | gaacgagagt | tgcctggcta | ctagagagac | 2280 |
| ttcttccaca | acaagaggga | gctgcctgcc | cccacagaag | acgtctttga | tgatgaccct | 2340 |
| gtgccttggt | agcatctatg | aggacttgaa | gatgtaccag | acagagttcc | aggccatcaa | 2400 |
| cgcagcactt | cagaatcaca | accatcagca | gatcattcta | gacaagggca | tgctggtggc | 2460 |
| catcgatgag | ctgatgcagt | ctctgaatca | taatggcgag | actctgcgcc | agaaacctcc | 2520 |
| tgtgggagaa | gcagacccctt | acagagtgaa | aatgaagctc | tgcatcctgc | ttcacgcctt | 2580 |
| cagcacccgc | gtcgtgacca | tcaacagggt | gatgggctat | ctgagctccg | cctgagaatt | 2640 |
| gatccggatt | agtccaattt | gttaaagaca | ggatgaagct | tctagataag | atatccgatc | 2700 |
| caccggatct | agataactga | tcataatcag | ccataccaca | tttgtagagg | ttttacttgc | 2760 |
| tttaaaaaac | ctcccacacc | tccccctgaa | cctgaaacat | aaaatgaatg | caattgttgt | 2820 |
| tgttaacttg | tttattgcag | cttataatgg | ttacaaataa | agcaatagca | tcacaaattt | 2880 |
| cacaaataaa | gcatttttt | cactgcattc | tagttgtggt | ttgtccaaac | tcatcaatgt | 2940 |
| atcttaacgc | nnnntaaggg | tgggaaagaa | tatataaggt | ggggggtctta | tgtagttttg | 3000 |
| tatctgtttt | gcagcagccg | ccgccgccat | gagcaccaac | tcgtttgatg | aagcattgt | 3060 |
| gagctcatat | ttgacaacgc | gcatgccccc | atgggccggg | gtgcgtcaga | atgtgatggg | 3120 |
| ctccagcatt | gatggtcgcc | ccgtcctgcc | cgcaaactct | actaccttga | cctacgagac | 3180 |
| cgtgtctgga | acgccgttgg | agactgcagc | ctccgccgcc | gcttcagccg | ctgcagccac | 3240 |
| cgcccgcggg | attgtgactg | actttgcttt | cctgagcccg | cttgcaagca | gtgcagcttc | 3300 |
| ccgttcatcc | gcccgcgatg | acaagttgac | ggctcttttg | gcacaattgg | attctttgac | 3360 |
| ccgggaactt | aatgtcgttt | ctcagcagct | gttggatctg | cgccagcagg | tttctgccct | 3420 |

```
gaaggcttcc tcccctccca atgcggttta aacataaat aaaaaaccag actctgtttg    3480
gatttggatc aagcaagtgt cttgctgtct ttatttaggg gttttgcgcg cgcggtaggc    3540
ccgggaccag cggtctcggt cgttgagggt cctgtgtatt ttttccagga cgtggtaaag    3600
gtgactctgg atgttcagat acatgggcat aagcccgtct ctggggtgga ggtagcacca    3660
ctgcagagct tcatgctgcg gggtggtgtt gtagatgatc cagtcgtagc aggagcgctg    3720
ggcgtggtgc ctaaaaatgt cttttcagtag caagctgatt gccaggggca ggcccttggt    3780
gtaagtgttt acaaagcggt taagctggga tgggtgcata cgtggggata tgagatgcat    3840
cttggactgt attttttaggt tggctatgtt cccagccata tccctccggg gattcatgtt    3900
gtgcagaacc accagcacag tgtatccggt gcacttggga aatttgtcat gtagcttaga    3960
aggaaatgcg tggaagaact tggagacgcc cttgtgacct ccaagatttt ccatgcattc    4020
gtccataatg atggcaatgg gcccacgggc ggcggcctgg gcgaagatat ttctgggatc    4080
actaacgtca tagttgtgtt ccaggatgag atcgtcatag gccattttta caaagcgcgg    4140
gcggagggtg ccagactgcg gtataatggt tccatccggc ccaggggcgt agttaccctc    4200
acagatttgc atttcccacg ctttgagttc agatgggggg atcatgtcta cctgcggggc    4260
gatgaagaaa acggtttccg gggtagggga gatcagctgg gaagaaagca ggttcctgag    4320
cagctgcgac ttaccgcagc cggtgggccc gtaaatcaca cctattaccg ggtgcaactg    4380
gtagttaaga gagctgcagc tgccgtcatc cctgagcagg ggggccactt cgttaagcat    4440
gtccctgact cgcatgtttt ccctgaccaa atccgccaga aggcgctcgc cgcccagcga    4500
tagcagttct tgcaaggaag caaagttttt caacggtttg agaccgtccg ccgtaggcat    4560
gcttttgagc gtttgaccaa gcagttccag gcggtcccac agctcggtca cctgctctac    4620
ggcatctcga tccagcatat ctcctcgttt cgcgggttgg ggcggctttc gctgtacggc    4680
agtagtcggt gctcgtccag acgggccagg gtcatgtctt ccacgggcg cagggtcctc    4740
gtcagcgtag tctgggtcac ggtgaagggg tgcgctccgg gctgcgcgct ggccagggtg    4800
cgcttgaggc tggtcctgct ggtgctgaag cgctgccggt cttcgccctg cgcgtcggcc    4860
aggtagcatt tgaccatggt gtcatagtcc agccctccg cggcgtggcc cttggcgcgc    4920
agcttgccct tggaggaggc gccgcacgag gggcagtgca gacttttgag ggcgtagagc    4980
ttgggcgcga gaaataccga ttccggggag taggcatccg cgccgcaggc cccgcagacg    5040
gtctcgcatt ccacgagcca ggtgagctct ggccgttcgg ggtcaaaaac caggtttccc    5100
ccatgctttt tgatgcgttt cttacctctg gtttccatga gccggtgtcc acgctcggtg    5160
acgaaaaggc tgtccgtgtc cccgtataca gactnnngtt taaacgaatt cnnnatataa    5220
aatgcaaggt gctgctcaaa aaatcaggca aagcctcgcg caaaaaagaa agcacatcgt    5280
agtcatgctc atgcagataa aggcaggtaa gctccggaac caccacagaa aaagacacca    5340
tttttctctc aaacatgtct gcgggtttct gcataaacac aaaataaaat aacaaaaaaa    5400
catttaaaca ttagaagcct gtcttacaac aggaaaaaca acccttataa gcataagacg    5460
gactacggcc atgccggcgt gaccgtaaaa aaactggtca ccgtgattaa aaagcaccac    5520
cgacagctcc tcggtcatgt ccggagtcat aatgtaagac tcggtaaaca catcaggttg    5580
attcatcggt cagtgctaaa aagcgaccga aatagcccgg gggaatacat acccgcaggc    5640
gtagagacaa cattacagcc cccataggag gtataacaaa attaatagga gagaaaaaca    5700
cataaacacc tgaaaaccc tcctgcctag gcaaaatagc accctcccgc tccagaacaa    5760
catacagcgc ttcacagcgg cagcctaaca gtcagcctta ccagtaaaaa agaaaaccta    5820
```

```
ttaaaaaaac accactcgac acggcaccag ctcaatcagt cacagtgtaa aaaagggcca      5880
agtgcagagc gagtatatat aggactaaaa aatgacgtaa cggttaaagt ccacaaaaaa      5940
cacccagaaa accgcacgcg aacctacgcc cagaaacgaa agccaaaaaa cccacaactt      6000
cctcaaatcg tcacttccgt tttcccacgt tacgtaactt cccatttaa gaaaactaca       6060 attcccaaca catacaagtt actccgccct aaaacctacg tcacccgccc cgttcccacg      6120
ccccgcgcca cgtcacaaac tccacccct cattatcata ttggcttcaa tccaaaataa       6180
ggtatattat tgatgatnnn ttaattaagg atccnnncgg tgtgaaatac cgcacagatg     6240
cgtaaggaga aaataccgca tcaggcgctc ttccgcttcc tcgctcactg actcgctgcg      6300
ctcggtcgtt cggctgcggc gagcggtatc agctcactca aaggcggtaa tacggttatc     6360
cacagaatca ggggataacg caggaaagaa catgtgagca aaaggccagc aaaaggccag     6420
gaaccgtaaa aaggccgcgt tgctggcgtt tttccatagg ctccgccccc ctgacgagca     6480
tcacaaaaat cgacgctcaa gtcagaggtg gcgaaacccg acaggactat aaagatacca     6540
ggcgtttccc cctggaagct ccctcgtgcg ctctcctgtt ccgaccctgc cgcttaccgg     6600 ataccgtgtcc gccttctcc cttcgggaag cgtggcgctt tctcatagct cacgctgtag      6660
gtatctcagt tcggtgtagg tcgttcgctc caagctgggc tgtgtgcacg aaccccccgt      6720
tcagcccgac cgctgcgcct tatccggtaa ctatcgtctt gagtccaacc cggtaagaca      6780
cgacttatcg ccactggcag cagccactgg taacaggatt agcagagcga ggtatgtagg      6840
cggtgctaca gagttcttga agtggtggcc taactacggc tacactagaa ggacagtatt     6900
tggtatctgc gctctgctga agccagttac cttcggaaaa agagttggta gctcttgatc      6960
cggcaaacaa accaccgctg gtagcggtgg tttttttgtt tgcaagcagc agattacgcg     7020
cagaaaaaaa ggatctcaag aagatccttt gatcttttct acggggtctg acgctcagtg     7080
gaacgaaaac tcacgttaag ggattttggt catgagatta tcaaaaagga tcttcaccta     7140 gatccttta aattaaaaat gaagttttaa atcaatctaa agtatatatg agtaaacttg       7200
gtctgacagt taccaatgct taatcagtga ggcacctatc tcagcgatct gtctatttcg     7260
ttcatccata gttgcctgac tccccgtcgt gtagataact acgatacggg agggcttacc     7320
atctggcccc agtgctgcaa tgataccgcg agacccacgc tcaccggctc cagatttatc      7380
agcaataaac cagccagccg aagggccga gcgcagaagt ggtcctgcaa ctttatccgc      7440
ctccatccag tctattaatt gttgccggga agctagagta agtagttcgc cagttaatag     7500
tttgcgcaac gttgttgnnn naaaaaggat cttcacctag atccttttca cgtagaaagc      7560
cagtccgcag aaacggtgct gacccccggat gaatgtcagc tactgggcta tctggacaag      7620
ggaaaacgca agcgcaaaga gaaagcaggt agcttgcagt gggcttacat ggcgatagct     7680
agactgggcg gttttatgga cagcaagcga accggaattg ccagctgggg cgccctctgg      7740
taaggttggg aagccctgca agtaaactg gatggctttc tcgccgccaa ggatctgatg     7800
gcgcagggga tcaagctctg atcaagagac aggatgagga tcgtttcgca tgattgaaca      7860
agatggattg cacgcaggtt ctccggccgc ttgggtggag aggctattcg gctatgactg     7920
ggcacaacag acaatcggct gctctgatgc cgccgtgttc cggctgtcag cgcaggggcg     7980
cccggttctt tttgtcaaga ccgacctgtc cggtgccctg aatgaactgc aagacgaggc     8040
agcgcggcta tcgtggctgg ccacgacggg cgttccttgc gcagctgtgc tcgacgttgt      8100
cactgaagcg ggaagggact ggctgctatt gggcgaagtg ccggggcagg atctcctgtc     8160
atctcacctt gctcctgccg agaaagtatc catcatggct gatgcaatgc ggcggctgca     8220
```

-continued

```
tacgcttgat ccggctacct gcccattcga ccaccaagcg aaacatcgca tcgagcgagc    8280
acgtactcgg atggaagccg tcttgtcga tcaggatgat ctggacgaag agcatcaggg    8340
gctcgcgcca gccgaactgt tcgccaggct caaggcgagc atgcccgacg gcgaggatct    8400
cgtcgtgacc catggcgatg cctgcttgcc gaatatcatg gtggaaaatg gccgcttttc    8460
tggattcatc gactgtggcc ggctgggtgt ggcggaccgc tatcaggaca tagcgttggc    8520
tacccgtgat attgctgaag agcttggcgg cgaatgggct gaccgcttcc tcgtgcttta    8580
cggtatcgcc gctcccgatt cgcagcgcat cgccttctat cgccttcttg acgagttctt    8640
ctgaattttg ttaaaatttt tgttaaatca gctcattttt taaccaatag gccgaaatcg    8700
gcaacatccc ttataaatca aaagaataga ccgcgatagg gttgagtgtt gttccagttt    8760
ggaacaagag tccactatta agaacgtgg actccaacgt caaagggcga aaaccgtct    8820 atcagggcga tggcccacta cgtgaaccat cacccaaatc aagttttttg cggtcgaggt    8880
gccgtaaagc tctaaatcgg aaccctaaag ggagcccccg atttagagct tgacggggaa    8940
agccggcgaa cgtggcgaga aggaaggga agaaagcgaa aggagcgggc gctagggcgc    9000
tggcaagtgt agcggtcacg ctgcgcgtaa ccaccacacc cgcgcgctt                9049
```

```
<210> SEQ ID NO 11
<211> LENGTH: 38246
<212> TYPE: DNA
<213> ORGANISM: Artificial Sequence
<220> FEATURE:
<223> OTHER INFORMATION: Plasmid containing the whole DNA coding for
      Ad-3
<220> FEATURE:
<221> NAME/KEY: misc_feature
<222> LOCATION: (1)..(38246)
<223> OTHER INFORMATION: "N" = "A", "C", "G" or "T"

<400> SEQUENCE: 11
```

```
nnttaattaa ggatccnnnc ggtgtgaaat accgcacaga tgcgtaagga gaaaataccg      60
catcaggcgc tcttccgctt cctcgctcac tgactcgctg cgctcggtcg ttcggctgcg    120
gcgagcggta tcagctcact caaaggcggt aatacggtta tccacagaat caggggataa    180
cgcaggaaag aacatgtgag caaaaggcca gcaaaaggcc aggaaccgta aaaaggccgc    240
gttgctggcg ttttttccata ggctccgccc ccctgacgag catcacaaaa atcgacgctc    300
aagtcagagg tggcgaaacc cgacaggact ataaagatac caggcgtttc ccctggaag    360 ctccctcgtg cgctctcctg ttccgaccct gccgcttacc ggatacctgt ccgcctttct    420
cccttcggga agcgtggcgc tttctcatag ctcacgctgt aggtatctca gttcggtgta    480
ggtcgttcgc tccaagctgg gctgtgtgca cgaaccccc gttcagcccg accgctgcgc    540
cttatccggt aactatcgtc ttgagtccaa cccggtaaga cacgacttat cgccactggc    600
agcagccact ggtaacagga ttagcagagc gaggtatgta ggcggtgcta cagagttctt    660
gaagtggtgg cctaactacg gctacactag aaggacagta tttggtatct gcgctctgct    720
gaagccagtt accttcggaa aaagagttgg tagctcttga tccggcaaac aaaccaccgc    780
tggtagcggt ggtttttttg tttgcaagca gcagattacg cgcagaaaaa aaggatctca    840
agaagatcct ttgatctttt ctacggggtc tgacgctcag tggaacgaaa actcacgtta    900
agggattttg gtcatgagat tatcaaaaag gatcttcacc tagatccttt taaattaaaa    960
atgaagtttt aaatcaatct aaagtatata tgagtaaact tggtctgaca gttaccaatg   1020
cttaatcagt gaggcaccta tctcagcgat ctgtctattt cgttcatcca tagttgcctg   1080
actccccgtc gtgtagataa ctacgatacg ggagggctta ccatctggcc ccagtgctgc   1140
```

```
aatgataccg cgagacccac gctcaccggc tccagattta tcagcaataa accagccagc   1200
cggaagggcc gagcgcagaa gtggtcctgc aactttatcc gcctccatcc agtctattaa   1260
ttgttgccgg gaagctagag taagtagttc gccagttaat agtttgcgca acgttgttgn   1320
nnnaaaaagg atcttcacct agatcctttt cacgtagaaa gccagtccgc agaaacggtg   1380
ctgaccccgg atgaatgtca gctactgggc tatctggaca agggaaaacg caagcgcaaa   1440
gagaaagcag gtagcttgca gtgggcttac atggcgatag ctagactggg cggttttatg   1500
gacagcaagc gaaccggaat tgccagctgg ggcgccctct ggtaaggttg ggaagccctg   1560
caaagtaaac tggatggctt tctcgccgcc aaggatctga tggcgcaggg gatcaagctc   1620
tgatcaagag acaggatgag gatcgtttcg catgattgaa caagatggat tgcacgcagg   1680
ttctccggcc gcttgggtgg agaggctatt cggctatgac tgggcacaac agacaatcgg   1740
ctgctctgat gccgccgtgt tccggctgtc agcgcagggg cgcccggttc ttttttgtcaa   1800 gaccgacctg tccggtgccc tgaatgaact gcaagacgag gcagcgcggc tatcgtggct   1860
ggccacgacg ggcgttcctt gcgcagctgt gctcgacgtt gtcactgaag cgggaaggga   1920
ctggctgcta ttgggcgaag tgccggggca ggatctcctg tcatctcacc ttgctcctgc   1980
cgagaaagta tccatcatgg ctgatgcaat gcggcggctg catacgcttg atccggctac   2040
ctgcccattc gaccaccaag cgaaacatcg catcgagcga gcgtactc ggatggaagc   2100 cggtcttgtc gatcaggatg atctggacga agagcatcag gggctcgcgc cagccgaact   2160
gttcgccagg ctcaaggcga gcatgcccga cggcgaggat ctcgtcgtga cccatggcga   2220
tgcctgcttg ccgaatatca tggtggaaaa tggccgcttt tctggattca tcgactgtgg   2280
ccggctgggt gtggcggacc gctatcagga catagcgttg gctacccgtg atattgctga   2340
agagcttggc ggcgaatggg ctgaccgctt cctcgtgctt tacggtatcg ccgctcccga   2400
ttcgcagcgc atcgccttct atcgccttct tgacgagttc ttctgaattt tgttaaaatt   2460
tttgttaaat cagctcattt tttaaccaat aggccgaaat cggcaacatc ccttataaat   2520
caaaagaata daccgcgata gggttgagtg ttgttccagt ttggaacaag agtccactat   2580
taaagaacgt ggactccaac gtcaaagggc gaaaaaccgt ctatcagggc gatggcccac   2640
tacgtgaacc atcacccaaa tcaagttttt tgcggtcgag gtgccgtaaa gctctaaatc   2700
ggaaccctaa agggagcccc cgatttagag cttgacgggg aaagccggcg aacgtggcga   2760
gaaaggaagg gaagaaagcg aaaggagcgg gcgctagggc gctggcaagt gtagcggtca   2820
cgctgcgcgt aaccaccaca cccgcgcgct taatgcgccg nnnnnnnnnn nnnnnnnnnn   2880
nnnnttaatt aannntccct tccagctctc tgccccttt ggattgaagc caatatgata   2940 atgaggggt ggagtttgtg acgtggcgcg gggcgtggga acgggcggg tgacgtagta   3000 gtgtggcgga agtgtgatgt tgcaagtgtg gcggaacaca tgtaagcgac ggatgtggca   3060
aaagtgacgt ttttggtgtg cgccggtgta cacaggaagt gacaattttc gcgcggtttt   3120
aggcggatgt tgtagtaaat ttgggcgtaa ccgagtaaga tttggccatt ttcgcgggaa   3180
aactgaataa gaggaagtga aatctgaata attttgtgtt actcatagcg cgtaannnnt   3240
aatagtaatc aattacgggg tcattagttc atagcccata tatggagttc cgcgttacat   3300
aacttacggt aaatggcccg cctggctgac cgcccaacga ccccgcccca ttgacgtcaa   3360
taatgacgta tgttcccata gtaacgccaa tagggacttt ccattgacgt caatgggtgg   3420
agtatttacg gtaaactgcc cacttggcag tacatcaagt gtatcatatg ccaagtacgc   3480
cccctattga cgtcaatgac ggtaaatggc ccgcctggca ttatgcccag tacatgacct   3540
```

```
tatgggactt tcctacttgg cagtacatct acgtattagt catcgctatt accatggtga   3600
tgcggttttg gcagtacatc aatgggcgtg gatagcggtt tgactcacgg ggatttccaa   3660
gtctccaccc cattgacgtc aatgggagtt tgttttggca ccaaaatcaa cgggactttc   3720
caaaatgtcg taacaactcc gccccattga cgcaaatggg cggtaggcgt gtacggtggg   3780
aggtctatat aagcagagct ggtttagtga accgtcagat ccgctagaga tctggatccg   3840
aattcgccgc caccatgggt cctcagaagc taaccatctc ctggtttgcc atcgttttgc   3900
tggtgtctcc actcatggcc atgtgggagc tggagaaaga cgtttatgtt gtagaggtgg   3960
actggactcc cgatgcccct ggagaaacag tgaacctcac ctgtgacacg cctgaagaag   4020
atgacatcac ctggacctca gaccagagac atggagtcat aggctctgga aagaccctga   4080
ccatcactgt caaagagttt ctagatgctg gccagtacac ctgccacaaa ggaggcgaga   4140
ctctgagcca ctcacatctg ctgctccaca agaaggaaaa tggaatttgg tccactgaaa   4200
ttttaaaaaa tttcaaaaac aagactttcc tgaagtgtga agcaccaaat tactccggac   4260
ggttcacgtg ctcatggctg gtgcaaagaa acatggactt gaagttcaac atcaagagca   4320
gtagcagttc ccctgactct cgggcagtga catgtggaat ggcgtctctg tctgcagaga   4380
aggtcacact ggaccaaagg gactatgaga agtattcagt gtcctgccag gaggatgtca   4440
cctgcccaac tgccgaggag accctgccca ttgaactggc gttggaagca cggcagcaga   4500
ataaatatga gaactacagc accagcttct tcatcaggga catcatcaaa ccagacccgc   4560
ccaagaactt gcagatgaag cctttgaaga actcacaggt ggaggtcagc tgggagtacc   4620
ctgactcctg gagcactccc cattcctact tctccctcaa gttctttgtt cgaatccagc   4680
gcaagaaaga aaagatgaag gagacagagg aggggtgtaa ccagaaaggt gcgttcctcg   4740
tagagaagac atctaccgaa gtccaatgca aaggcgggaa tgtctgcgtg caagctcagg   4800
atcgctatta caattcctca tgcagcaagt gggcatgtgt tccctgcagg gtccgatccg   4860
gtggcggtgg ctcgggcggt ggtgggtcgg gtggcggcgg atctagggtc attccagtct   4920
ctggacctgc caggtgtctt agccagtccc gaaacctgct gaagaccaca gatgacatgg   4980
tgaagacggc cagagaaaaa ctgaaacatt attcctgcac tgctgaagac atcgatcatg   5040
aagcatcac acgggaccaa accagcacat tgaagacctg tttaccactg gaactacaca   5100
agaacgagag ttgcctggct actagagaga cttcttccac aacaagaggg agctgcctgc   5160
ccccacagaa gacgtctttg atgatgaccc tgtgccttgg tagcatctat gaggacttga   5220
agatgtacca gacagagttc caggccatca acgcagcact tcagaatcac aaccatcagc   5280
agatcattct agacaagggc atgctggtgg ccatcgatga gctgatgcag tctctgaatc   5340
ataatggcga gactctgcgc cagaaacctc tgtgggagag agcagaccct acagagtgaa   5400
aaatgaagct ctgcatcctg cttcacgcct tcagcacccg cgtcgtgacc atcaacaggg   5460
tgatgggcta tctgagctcc gcctgagaat tgatccggat tagtccaatt tgttaaagac   5520
aggatgaagc ttttaaaaca gctctgggggt tgtacccacc ccagaggccc acgtggcggc   5580
tagtactccg gtattgcggt acccttgtac gcctgtttta tactcccttc ccgtaactta   5640
gacgcacaaa accaagttca atagaagggg gtacaaacca gtaccaccac gaacaagcac   5700
ttctgttttcc ccggtgatgt cgtatagact gcttgcgtgg ttgaaagcga cggatccgtt   5760
atccgcttat gtacttcgag aagcccagta ccacctcgga atcttcgatg cgttgcgctc   5820
agcactcaac cccagagtgt agcttaggct gatgagtctg gacatccctc accggtgacg   5880
gtggtccagg ctgcgttggc ggcctaccta tggctaacgc catgggacgc tagttgtgaa   5940
```

```
caaggtgtga agagcctatt gagctacata agaatcctcc ggcccctgaa tgcggctaat    6000
cccaacctcg gagcaggtgg tcacaaacca gtgattggcc tgtcgtaacg cgcaagtccg    6060
tggcggaacc gactactttg ggtgtccgtg tttccttttta ttttattgtg gctgcttatg   6120
gtgacaatca cagattgtta tcataaagcg aattggattg cggccgcatg atcgaccagc   6180
acacacttga tgtggaggat accgcggatg ccagacatcc agcaggtact tcgtgcccct   6240
cggatgcggc gctcctcaga gataccgggc tcctcgcgga cgctgcgctc ctctcagata   6300
ctgtgcgccc cacaaatgcc gcgctcccca cggatgctgc ctaccctgcg gttaatgttc   6360
gggatcgcga ggccgcgtgg ccgcctgcac tgaacttctg ttcccgccac ccaaagctct   6420
atggcctagt cgcttttggtt ttgctgcttc tgatcgccgc ctgtgttcct atcttcaccc   6480
gcaccgagcc tcggccagcg ctcacaatca ccacctcgcc caacctgggt acccgagaga   6540
ataatgcaga ccaggtcacc cctgtttccc acattggctg ccccaacact acacaacagg   6600
gctctcctgt gttcgccaag ctactggcta aaaccaagc atcgttgtgc aatacaactc     6660
tgaactggca cagccaagat ggagctggga gctcatacct atctcaaggt ctgaggtacg   6720
aagaagacaa aaaggagttg gtggtagaca gtcccgggct ctactacgta ttttttggaac  6780
tgaagctcag tccaacattc acaaacacag gccacaaggt gcagggctgg gtctctcttg   6840
ttttgcaagc aaagcctcag gtagatgact ttgacaactt ggccctgaca gtggaactgt   6900
tcccttgctc catggagaac aagttagtgg accgttcctg gagtcaactg ttgctcctga   6960
aggctggcca ccgcctcagt gtgggtctga ggcttatct gcatggagcc caggatgcat    7020
acagagactg ggagctgtct tatcccaaca ccaccagctt tggactcttt cttgtgaaac   7080
ccgacaaccc atgggaatga aactatcct tcttgtgact ggcgcgcctg atcaatcgat     7140
gtttaaacgt tattttccac catattgccg tcttttggca atgtgagggc ccggaaacct   7200
ggccctgtct tcttgacgag cattcctagg ggtctttccc ctctcgccaa aggaatgcaa   7260
ggtctgttga atgtcgtgaa ggaagcagtt cctctggaag cttcttgaag acaaacaacg   7320
tctgtagcga ccctttgcag gcagcggaac ccccacctg cgacaggtg cctctgcggc      7380
caaaagccac gtgtataaga tacacctgca aaggcggcac aaccccagtg ccacgttgtg    7440
agttggatag ttgtggaaag agtcaaatgg ctctcctcaa gcgtattcaa caaggggctg   7500
aaggatgccc agaaggtacc ccattgtatg ggatctgatc tggggcctcg gtgcacatgc   7560
tttacgtgtg tttagtcgag gttaaaaaac gtctaggccc cccgaaccac ggggacgtgg   7620
ttttcctttg aaaaacacga ttctcgagac tagtgccacc atgtacagca tgcagctcgc   7680
atcctgtgtc acattgacac ttgtgctcct tgtcaacagc gcacccactt caagctccac   7740
ttcaagctct acagcggaag cacagcagca gcagcagcag cagcagcagc agcagcagca   7800
cctggagcag ctgttgatgg acctacagga gctcctgagc aggatggaga attacaggaa   7860
cctgaaactc ccaggatgc tcaccttcaa attttacttg cccaagcagg ccacagaatt     7920
gaaagatctt cagtgcctag aagatgaact tggacctctg cggcatgttc tggatttgac    7980
tcaaagcaaa agctttcaat tggaagatgc tgagaatttc atcagcaata tcagagtaac   8040
tgttgtaaaa ctaaagggct ctgacaacac atttgagtgc caattcgatg atgagtcagc   8100
aactgtggtg gactttctga ggagatggat agccttctgt caaagcatca tctcaacaag   8160
ccctcaataa ctatgtaacg cgtgctagca tggccggccg cggccgcggc cgctcgagcc   8220
taagcttcta gataagatat ccgatccacc ggatctagat aactgatcat aatcagccat   8280
accacatttg tagaggtttt acttgcttta aaaaacctcc cacacctccc cctgaacctg   8340
```

```
aaacataaaa tgaatgcaat tgttgttgtt aacttgttta ttgcagctta taatggttac   8400
aaataaagca atagcatcac aaatttcaca aataaagcat ttttttcact gcattctagt   8460
tgtggtttgt ccaaactcat caatgtatct taacgcnnnn taagggtggg aaagaatata   8520
taaggtgggg gtcttatgta gttttgtatc tgttttgcag cagccgccgc cgccatgagc   8580
accaactcgt ttgatggaag cattgtgagc tcatatttga caacgcgcat gcccccatgg   8640
gccggggtgc gtcagaatgt gatgggctcc agcattgatg gtcgcccgt cctgcccgca    8700 aactctacta ccttgaccta cgagaccgtg tctggaacgc cgttggagac tgcagcctcc   8760
gccgccgctt cagccgctgc agccaccgcc cgcgggattg tgactgactt tgcttcctg    8820 agcccgcttg caagcagtgc agcttcccgt tcatccgccc gcgatgacaa gttgacggct   8880
cttttggcac aattggattc tttgacccgg gaacttaatg tcgtttctca gcagctgttg   8940
gatctgcgcc agcaggtttc tgccctgaag gcttcctccc ctcccaatgc ggtttaaaac   9000
ataaataaaa aaccagactc tgtttggatt tggatcaaga aagtgtcttg ctgtctttat   9060 ttagggggttt tgcgcgcgcg gtaggcccgg gaccagcggt ctcggtcgtt gagggtcctg   9120
tgtatttttt ccaggacgtg gtaaaggtga ctctggatgt tcagatacat gggcataagc   9180
ccgtctctgg ggtggaggta gcaccactgc agagcttcat gctgcggggt ggtgttgtag   9240
atgatccagt cgtagcagga gcgctgggcg tggtgcctaa aaatgtcttt cagtagcaag   9300
ctgattgcca ggggcaggcc cttggtgtaa gtgtttacaa agcggttaag ctgggatggg   9360
tgcatacgtg gggatatgag atgcatcttg gactgtattt ttaggttggc tatgttccca   9420
gccatatccc tccggggatt catgttgtgc agaaccacca gcacagtgta tccggtgcac   9480
ttgggaaatt tgtcatgtag cttagaagga aatgcgtgga agaacttgga gacgcccttg   9540
tgacctccaa gattttccat gcattcgtcc ataatgatgg caatgggccc acgggcggcg   9600
gcctgggcga agatatttct gggatcacta acgtcatagt tgtgttccag gatgagatcg   9660
tcataggcca ttttttacaaa gcgcgggcgg agggtgccag actgcggtat aatggttcca   9720
tccggcccag gggcgtagtt accctcacag atttgcattt cccacgcttt gagttcagat   9780 gggggggatca tgtctacctg cggggcgatg aagaaaacgg tttccggggt aggggagatc   9840
agctgggaag aaagcaggtt cctgagcagc tgcgacttac cgcagccggt gggcccgtaa   9900
atcacaccta ttaccgggtg caactggtag ttaagagagc tgcagctgcc gtcatccctg   9960
agcagggggg ccacttcgtt aagcatgtcc ctgactcgca tgttttccct gaccaaatcc  10020
gccagaaggc gctcgccgcc cagcgatagc agttcttgca aggaagcaaa gttttcaac   10080 ggtttgagac cgtccgccgt aggcatgctt ttgagcgttt gaccaagcag ttccaggcgg  10140
tcccacagct cggtcacctg ctctacggca tctcgatcca gcatatctcc tcgtttcgcg  10200
ggttggggcg gctttcgctg tacggcagta gtcggtgctc gtccagacgg gccagggtca  10260 tgtcttttcca cgggcgcagg gtcctcgtca gcgtagtctg ggtcacggtg aagggtgcg   10320 ctccggggctg cgcgctggcc agggtgcgct tgaggctggt cctgctggtg ctgaagcgct  10380
gccggtcttc gccctgcgcg tcggccaggt agcatttgac catggtgtca tagtccagcc  10440
cctccgcggc gtggcccttg gcgcgcagct tgcccttgga ggaggcgccg cacgaggggc  10500
agtgcagact tttgagggcg tagagcttgg gcgcgagaaa taccgattcc ggggagtagg  10560
catccgcgcc gcaggccccg cagacggtct cgcattccac gagccaggtg agctctggcc  10620
gttcggggtc aaaaaccagg tttcccccat gcttttgat gcgttcttta cctctggttt    10680
ccatgagccg gtgtccacgc tcggtgacga aaaggctgtc cgtgtccccg tatacagact  10740
```

```
tgagaggcct gtcctcgagc ggtgttccgc ggtcctcctc gtatagaaac tcggaccact   10800
ctgagacaaa ggctcgcgtc caggccagca cgaaggaggc taagtgggag gggtagcggt   10860
cgttgtccac tagggggtcc actcgctcca gggtgtgaag acacatgtcg ccctcttcgg   10920
catcaaggaa ggtgattggt ttgtaggtgt aggccacgtg accgggtgtt cctgaagggg   10980
ggctataaaa gggggtgggg gcgcgttcgt cctcactctc ttccgcatcg ctgtctgcga   11040
gggccagctg ttggggtgag tactccctct gaaaagcggg catgacttct gcgctaagat   11100
tgtcagtttc caaaaacgag gaggatttga tattcacctg gcccgcggtg atgcctttga   11160
gggtggccgc atccatctgg tcagaaaaga caatcttttt gttgtcaagc ttggtggcaa   11220
acgacccgta gagggcgttg acagcaact tggcgatgga gcgcagggtt tggttttttgt   11280 cgcgatcggc gcgctccttg gccgcgatgt ttagctgcac gtattcgcgc gcaacgcacc   11340
gccattcggg aaagacggtg gtgcgctcgt cgggcaccag gtgcacgcgc caaccgcggt   11400
tgtgcagggt gacaaggtca acgctggtgg ctacctctcc gcgtaggcgc tcgttggtcc   11460
agcagaggcg gccgcccttg cgcgagcaga atggcggtag ggggtctagc tgcgtctcgt   11520 ccgggggtc tgcgtccacg gtaaagaccc cgggcagcag gcgcgcgtcg aagtagtcta   11580
tcttgcatcc ttgcaagtct agcgcctgct gccatgcgcg ggcggcaagc gcgcgctcgt   11640
atgggttgag tgggggaccc catggcatgg ggtgggtgag cgcggaggcg tacatgccgc   11700
aaatgtcgta aacgtagagg ggctctctga gtattccaag atatgtaggg tagcatcttc   11760
caccgcggat gctggcgcgc acgtaatcgt atagttcgtg cgagggagcg aggaggtcgg   11820
gaccgaggtt gctacgggcg ggctgctctg ctcggaagac tatctgcctg aagatggcat   11880
gtgagttgga tgatatggtt ggacgctgga agacgttgaa gctggcgtct gtgagaccta   11940
ccgcgtcacg cacgaaggag gcgtaggagt cgcgcagctt gttgaccagc tcggcggtga   12000
cctgcacgtc tagggcgcag tagtccaggg tttttccttgat gatgtcatac ttatcctgtc   12060
cctttttttt ccacagctcg cggttgagga caaactcttc gcggtctttc cagtactctt   12120
ggatcggaaa cccgtcggcc tccgaacggt aagagcctag catgtagaac tggttgacgg   12180
cctggtaggc gcagcatccc ttttctacgg gtagcgcgta tgcctgcgcg gccttccgga   12240
gcgaggtgtg ggtgagcgca aaggtgtccc tgaccatgac tttgaggtac tggtatttga   12300
agtcagtgtc gtcgcatccg ccctgctccc agagcaaaaa gtccgtgcgc ttttttggaac   12360 gcggatttgg cagggcgaag gtgacatcgt tgaagagtat ctttcccgcg cgaggcataa   12420
agttgcgtgt gatgcggaag ggtcccggca cctcggaacg gttgttaatt acctgggcgg   12480
cgagcacgat ctcgtcaaag ccgttgatgt tgtggcccac aatgtaaagt tccaagaagc   12540
gcgggatgcc cttgatggaa ggcaattttt taagttcctc gtaggtgagc tcttcagggg   12600
agctgagccc gtgctctgaa agggcccagt ctgcaagatg aggggttggaa gcgacgaatg   12660 agctccacag gtcacgggcc attagcattt gcaggtggtc gcgaaaggtc ctaaactggc   12720
gacctatggc cattttttct ggggtgatgc agtagaaggt aagcgggtct tgttcccagc   12780
ggtcccatcc aaggttcgcg gctaggtctc gcgcggcagt cactagaggc tcatctccgc   12840
cgaacttcat gaccagcatg aagggcacga gctgcttccc aaaggccccc atccaagtat   12900
aggtctctac atcgtaggtg acaaagagac gctcggtgcg aggatgcgag ccgatcggga   12960
agaactggat ctcccgccac caattggagg agtggctatt gatgtggtga agtagaagt   13020 ccctgcgacg ggccgaacac tcgtgctggc ttttgtaaaa acgtgcgcag tactggcagc   13080
ggtgcacggg ctgtacatcc tgcacgaggt tgacctgacg accgcgcaca aggaagcaga   13140
```

```
gtgggaattt gagcccctcg cctggcgggt ttggctggtg gtcttctact tcggctgctt    13200
gtccttgacc gtctggctgc tcgaggggag ttacggtgga tcggaccacc acgccgcgcg    13260
agcccaaagt ccagatgtcc gcgcgcgcg gtcggagctt gatgacaaca tcgcgcagat    13320
gggagctgtc catggtctgg agctcccgcg gcgtcaggtc aggcgggagc tcctgcaggt    13380
ttacctcgca tagacgggtc agggcgcggg ctagatccag gtgataccta atttccaggg    13440
gctggttggt ggcggcgtcg atggcttgca agaggccgca tccccgcggc gcgactacgg    13500
taccgcgcgg cgggcggtgg gccgcggggg tgtccttgga tgatgcatct aaaagcggtg    13560
acgcgggcga gccccggag gtagggggg ctccggaccc gccgggagag ggggcagggg    13620
cacgtcggcg ccgcgcgcgg gcaggagctg gtgctgcgcg cgtaggttgc tggcgaacgc    13680
gacgacgcgg cggttgatct cctgaatctg gcgcctctgc gtgaagacga cgggcccggt    13740
gagcttgagc ctgaaagaga gttcgacaga atcaatttcg gtgtcgttga cggcggcctg    13800
gcgcaaaatc tcctgcacgt ctcctgagtt gtcttgatag gcgatctcgg ccatgaactg    13860
ctcgatctct tcctcctgga gatctccgcg tccggctcgc tccacggtgg cggcgaggtc    13920
gttggaaatg cgggccatga gctgcagaa ggcgttgagg cctccctcgt tccagacgcg    13980
gctgtagacc acgccccctt cggcatcgcg ggcgcgcatg accacctgcg cgagattgag    14040
ctccacgtgc cgggcgaaga cggcgtagtt tcgcaggcgc tgaaagaggt agttgagggt    14100
ggtggcggtg tgttctgcca cgaagaagta cataacccag cgtcgcaacg tggattcgtt    14160
gatatccccc aaggcctcaa ggcgctccat ggcctcgtag aagtccacgg cgaagttgaa    14220
aaactgggag ttgcgcgccg acacggttaa ctcctcctcc agaagacgga tgagctcggc    14280
gacagtgtcg cgcacctcgc gctcaaaggc tacaggggcc tcttcttctt cttcaatctc    14340
ctcttccata agggcctccc cttcttcttc ttctggcggc ggtgggggag ggggacacg    14400 gcggcgacga cggcgcaccg ggaggcggtc gacaaagcgc tcgatcatct ccccgcggcg    14460
acggcgcatg gtctcggtga cggcgcggcc gttctcgcgg gggcgcagtt ggaagacgcc    14520
gcccgtcatg tcccggttat gggttggcgg ggggctgcca tgcggcaggg atacggcgct    14580
aacgatgcat ctcaacaatt gttgtgtagg tactccgccg ccgagggacc tgagcgagtc    14640
cgcatcgacc ggatcggaaa acctctcgag aaaggcgtct aaccagtcac agtcgcaagg    14700
taggctgagc accgtggcgg gcggcagcgg gcggcggtcg gggttgtttc tggcggaggt    14760
gctgctgatg atgtaattaa agtaggcggt cttgagacgg cggatggtcg acagaagcac    14820
catgtccttg ggtccggcct gctgaatgcg caggcggtcg gccatgcccc aggcttcgtt    14880
ttgacatcgg cgcaggtctt tgtagtagtc ttgcatgagc ctttctaccg gcacttcttc    14940
ttctccttcc tcttgtcctg catctcttgc atctatcgct gcggcggcgg cggagtttgg    15000
ccgtaggtgg cgccctcttc ctcccatgcg tgtgaccccg aagcccctca tcggctgaag    15060
cagggctagg tcgcgacaa cgcgctcggc taatatggcc tgctgcacct gcgtgagggt    15120
agactggaag tcatccatgt ccacaaagcg gtggtatgcg cccgtgttga tggtgtaagt    15180
gcagttggcc ataacggacc agttaacggt ctggtgaccc ggctgcgaga gctcggtgta    15240
cctgagacgc gagtaagccc tcgagtcaaa tacgtagtcg ttgcaagtcc gcaccaggta    15300
ctggtatccc accaaaaagt gcggcggcgg ctggcggtag aggggccagc gtagggtggc    15360
cggggctccg ggggcgagat cttccaacat aaggcgatga tatccgtaga tgtacctgga    15420
catccaggtg atgccggcgg cggtggtgga ggcgcgcgga aagtcgcgga cgcggttcca    15480
gatgttgcgc agcggcaaaa agtgctccat ggtcgggacg ctctggccgg tcaggcgcgc    15540
```

```
gcaatcgttg acgctctacc gtgcaaaagg agagcctgta agcgggcact cttccgtggt   15600
ctggtggata aattcgcaag ggtatcatgg cggacgaccg gggttcgagc cccgtatccg   15660
gccgtccgcc gtgatccatg cggttaccgc ccgcgtgtcg aacccaggtg tgcgacgtca   15720
gacaacgggg gagtgctcct tttggcttcc ttccaggcgc ggcggctgct gcgctagctt   15780
ttttggccac tggccgcgcg cagcgtaagc ggttaggctg gaaagcgaaa gcattaagtg   15840
gctcgctccc tgtagccgga gggttatttt ccaagggttg agtcgcggga cccccggttc   15900
gagtctcgga ccggccggac tgcggcgaac gggggtttgc ctccccgtca tgcaagaccc   15960
cgcttgcaaa ttcctccgga aacagggacg agccccttt ttgcttttcc cagatgcatc   16020
cggtgctgcg gcagatgcgc ccccctcctc agcagcggca agagcaagag cagcggcaga   16080
catgcagggc accctcccct cctcctaccg cgtcaggagg ggcgacatcc gcggttgacg   16140
cggcagcaga tggtgattac gaaccccccgc ggcgccgggc ccggcactac ctggacttgg   16200
aggagggcga gggcctggcg cggctaggag cgccctctcc tgagcggtac ccaagggtgc   16260
agctgaagcg tgatacgcgt gaggcgtacg tgccgcggca gaacctgttt cgcgaccgcg   16320
agggagagga gcccgaggag atgcgggatc gaaagttcca cgcagggcgc gagctgcggc   16380
atggcctgaa tcgcgagcgg ttgctgcgcg aggaggactt tgagcccgac gcgcgaaccg   16440
ggattagtcc cgcgcgcgca cacgtggcgg ccgccgacct ggtaaccgca tacgagcaga   16500
cggtgaacca ggagattaac tttcaaaaaa gctttaacaa ccacgtgcgt acgcttgtgg   16560
cgcgcgagga ggtggctata ggactgatgc atctgtggga cttgtaagc gcgctggagc   16620
aaaacccaaa tagcaagccg ctcatggcgc agctgttcct tatagtgcag cacagcaggg   16680
acaacgagcg attcagggat gcgctgctaa acatagtaga gcccgagggc cgctggctgc   16740
tcgatttgat aaacatcctg cagagcatag tggtgcagga gcgcagcttg agcctggctg   16800
acaaggtggc cgccatcaac tattccatgc ttagcctggg caagttttac gcccgcaaga   16860
tataccatac cccttacgtt cccatagaca aggaggtaaa gatcgagggg ttctacatgc   16920
gcatggcgct gaaggtgctt accttgagcg acgacctggg cgtttatcgc aacgagcgca   16980
tccacaaggc cgtgagcgtg agccggcggc gcgagctcag cgaccgcgag ctgatgcaca   17040
gcctgcaaag ggccctggct ggcacgggca gcggcgatag agaggccgag tcctactttg   17100
acgcgggcgc tgacctgcgc tgggcccaa gccgacgcgc cctggaggca gctggggccg   17160
gacctgggct ggcggtggca cccgcgcgcg ctggcaacgt cggcggcgtg gaggaatatg   17220
acgaggacga tgagtacgag ccagaggacg gcgagtacta gccggtgatg tttctgatca   17280
gatgatgcaa gacgcaacgg acccggcggt gcggcggcg ctgcagagcc agccgtccgg   17340
ccttaactcc acggacgact ggcgccaggt catggaccgc atcatgtcgc tgactgcgcg   17400
caatcctgac gcgttccggc agcagccgca ggccaaccgg ctctccgcaa ttctggaagc   17460
ggtggtcccg gcgcgcgcaa accccacgca cgagaaggtg ctggcgatcg taaacgcgct   17520
ggccgaaaac agggccatcc ggcccgacga ggccggcctg gtctacgacg cgctgcttca   17580
gcgcgtggct cgttacaaca gcggcaacgt gcagaccaac ctggaccggc tggtgggga   17640
tgtgcgcgag gccgtggcgc agcgtgagcg cgcgcagcag cagggcaacc tgggctccat   17700
ggttgcacta aacgccttcc tgagtacaca gcccgccaac gtgccgcggg acaggagga   17760
ctacaccaac tttgtgagcg cactgcggct aatggtgact gagacaccgc aaagtgaggt   17820
gtaccagtct gggccagact atttttttcca gaccagtaga caaggcctgc agaccgtaaa   17880
cctgagccag gctttcaaaa acttgcaggg gctgtggggg gtgcgggctc ccacaggcga   17940
```

```
ccgcgcgacc gtgtctagct tgctgacgcc caactcgcgc ctgttgctgc tgctaatagc    18000
gcccttcacg gacagtggca gcgtgtcccg ggacacatac ctaggtcact tgctgacact    18060
gtaccgcgag gccataggtc aggcgcatgt ggacgagcat actttccagg agattacaag    18120
tgtcagccgc gcgctggggc aggaggacac gggcagcctg gaggcaaccc taaactacct    18180
gctgaccaac cggcggcaga agatcccctc gttgcacagt ttaaacagcg aggaggagcg    18240
cattttgcgc tacgtgcagc agagcgtgag ccttaacctg atgcgcgacg gggtaacgcc    18300
cagcgtggcg ctggacatga ccgcgcgcaa catggaaccg ggcatgtatg cctcaaaccg    18360
gccgtttatc aaccgcctaa tggactactt gcatcgcgcg gccgccgtga accccgagta    18420
tttcaccaat gccatcttga acccgcactg gctaccgccc cctggtttct acaccggggg    18480
attcgaggtg cccgagggta acgatggatt cctctgggac gacatagacg acagcgtgtt    18540
ttccccgcaa ccgcagaccc tgctagagtt gcaacagcgc gagcaggcag aggcggcgct    18600
gcgaaaggaa agcttccgca ggccaagcag cttgtccgat ctaggcgctg cggccccgcg    18660
gtcagatgct agtagcccat ttccaagctt gatagggtct cttaccagca ctcgcaccac    18720
ccgcccgcgc ctgctgggcg aggaggagta cctaaacaac tcgctgctgc agccgcagcg    18780
cgaaaaaaac ctgcctccgg catttcccaa caacgggata gagagcctag tggacaagat    18840
gagtagatgg aagacgtacg cgcaggagca cagggacgtg ccaggcccgc gcccgcccac    18900
ccgtcgtcaa aggcacgacc gtcagcgggg tctggtgtgg gaggacgatg actcggcaga    18960
cgacagcagc gtcctggatt tgggagggag tggcaacccg tttgcgcacc ttcgccccag    19020
gctggggaga atgtttttaaa aaaaaaaag catgatgcaa aataaaaaac tcaccaaggc    19080
catggcaccg agcgttggtt ttcttgtatt cccttagta tgcggcgcgc ggcgatgtat    19140
gaggaaggtc ctcctccctc ctacgagagt gtggtgagcg cggcgccagt ggcggcggcg    19200
ctgggttctc ccttcgatgc tccctggac ccgccgtttg tgcctccgcg gtacctgcgg    19260
cctaccgggg ggagaaacag catccgttac tctgagttgg caccctatt cgacaccacc    19320 cgtgtgtacc tggtggacaa caagtcaacg gatgtggcat ccctgaacta ccagaacgac    19380
cacagcaact ttctgaccac ggtcattcaa aacaatgact acagcccggg ggaggcaagc    19440
acacagacca tcaatcttga cgaccggtcg cactggggcg gcgacctgaa aaccatcctg    19500
cataccaaca tgccaaatgt gaacgagttc atgtttacca ataagtttaa ggcgcgggtg    19560
atggtgtcgc gcttgcctac taaggacaat caggtggagc tgaaatacga gtgggtggag    19620
ttcacgctgc ccgagggcaa ctactccgag accatgacca tagaccttat gaacaacgcg    19680
atcgtggagc actacttgaa agtgggcaga cagaacgggg ttctggaaag cgacatcggg    19740
gtaaagtttg acaccccgcaa cttcagactg ggtttgacc ccgtcactgg tcttgtcatg    19800
cctggggtat atacaaacga agccttccat ccagacatca ttttgctgcc aggatgcggg    19860
gtggacttca cccacagccg cctgagcaac ttgttgggca tccgcaagcg caacccttc    19920 caggagggct ttaggatcac ctacgatgat ctgagggtg gtaacattcc cgcactgttg    19980
gatgtggacg cctaccaggc gagcttgaaa gatgacaccg aacagggcgg gggtggcgca    20040
ggcggcagca acagcagtgg cagcggcgcg gaagagaact ccaacgcggc agccgcggca    20100
atgcagccgg tggaggacat gaacgatcat gccattcgcg cgacaccttt gccacacgg    20160 gctgaggaga agcgcgctga ggccgaagca gcggccgaag ctgccgcccc cgctgcgcaa    20220
cccgaggtcg agaagcctca gaagaaaccg gtgatcaaac ccctgacaga ggacagcaag    20280
aaacgcagtt acaacctaat aagcaatgac agcaccttca cccagtaccg cagctggtac    20340
```

```
cttgcataca actacggcga ccctcagacc ggaatccgct catggaccct gctttgcact    20400
cctgacgtaa cctgcggctc ggagcaggtc tactggtcgt tgccagacat gatgcaagac    20460
cccgtgacct tccgctccac gcgccagatc agcaactttc cggtggtggg cgccgagctg    20520
ttgcccgtgc actccaagag cttctacaac gaccaggccg tctactccca actcatccgc    20580
cagtttacct ctctgaccca cgtgttcaat cgctttcccg agaaccagat tttggcgcgc    20640
ccgccagccc ccaccatcac caccgtcagt gaaaacgttc ctgctctcac agatcacggg    20700
acgctaccgc tgcgcaacag catcggagga gtccagcgag tgaccattac tgacgccaga    20760
cgccgcacct gcccctacgt ttacaaggcc ctgggcatag tctcgccgcg cgtcctatcg    20820
agccgcactt tttgagcaag catgtccatc cttatatcgc ccagcaataa cacaggctgg    20880
ggcctgcgct tcccaagcaa gatgtttggc ggggccaaga agcgctccga ccaacaccca    20940
gtgcgcgtgc gcgggcacta ccgcgcgccc tgggcgcgc acaaacgcgg ccgcactggg    21000
cgcaccaccg tcgatgacgc catcgacgcg gtggtggagg aggcgcgcaa ctacacgccc    21060
acgccgccac cagtgtccac agtggacgcg gccattcaga ccgtggtgcg cggagcccgg    21120
cgctatgcta aaatgaagag acggcggagg cgcgtagcac gtcgccaccg ccgccgaccc    21180
ggcactgccg cccaacgcgc ggcggcggcc ctgcttaacc gcgcacgtcg caccggccga    21240
cgggcggcca tgcgggccgc tcgaaggctg gccgcgggta ttgtcactgt gcccccagg    21300 tccaggcgac gagcggccgc cgcagcagcc gcggccatta gtgctatgac tcagggtcgc    21360
aggggcaacg tgtattgggt gcgcgactcg gttagcggcc tgcgcgtgcc cgtgcgcacc    21420
cgccccccgc gcaactagat tgcaagaaaa aactacttag actcgtactg ttgtatgtat    21480 ccagcggcg cggcgcgcaa cgaagctatg tccaagcgca aaatcaaaga agagatgctc    21540
caggtcatcg cgccggagat ctatggcccc ccgaagaagg aagagcagga ttacaagccc    21600
cgaaagctaa agcgggtcaa aaagaaaaag aaagatgatg atgatgaact tgacgacgag    21660
gtggaactgc tgcacgctac cgcgcccagg cgacgggtac agtggaaagg tcgacgcgta    21720
aaacgtgttt tgcgacccgg caccaccgta gtctttacgc ccggtgagcg ctccacccgc    21780
acctacaagc gcgtgtatga tgaggtgtac ggcgacgagg acctgcttga gcaggccaac    21840
gagcgcctcg gggagtttgc ctacggaaag cggcataagg acatgctggc gttgccgctg    21900
gacgagggca acccaacacc tagcctaaag cccgtaacac tgcagcaggt gctgcccgcg    21960
cttgcaccgt ccgaagaaaa gcgcggccta aagcgcgagt ctggtgactt ggcacccacc    22020
gtgcagctga tggtacccaa gcgccagcga ctggaagatg tcttggaaaa aatgaccgtg    22080
gaacctgggc tggagcccga ggtccgcgtg cggccaatca gcaggtggc gccgggactg    22140 ggcgtgcaga ccgtggacgt tcagatacc actaccagta gcaccagtat tgccaccgcc    22200
acagagggca tggagacaca aacgtccccg gttgcctcag cggtggcgga tgccgcggtg    22260
caggcggtcg ctgcggccgc gtccaagacc tctacggagg tgcaaacgga cccgtggatg    22320
tttcgcgttt cagcccccg cgcccgcgc ggttcgagga agtacggcgc cgccagcgcg    22380
ctactgcccg aatatgccct acatccttcc attgcgccta cccccggcta tcgtggctac    22440
acctaccgcc ccagaagacg agcaactacc cgacgcgaa ccaccactgg aacccgccgc    22500
cgccgtcgcc gtcgccagcc cgtgctggcc ccgatttccg tgcgcagggt ggctcgcgaa    22560
ggaggcagga ccctggtgct gccaacagcg cgctaccacc ccagcatcgt ttaaaagccg    22620
gtctttgtgg ttcttgcaga tatggccctc acctgccgcc tccgtttccc ggtgccggga    22680
ttccgaggaa gaatgcaccg taggaggggc atggccggcc acggcctgac gggcggcatg    22740
```

```
cgtcgtgcgc accaccggcg gcggcgcgcg tcgcaccgtc gcatgcgcgg cggtatcctg   22800
cccctcctta ttccactgat cgccgcggcg attggcgccg tgcccggaat tgcatccgtg   22860
gccttgcagg cgcagagaca ctgattaaaa acaagttgca tgtggaaaaa tcaaaataaa   22920
aagtctggac tctcacgctc gcttggtcct gtaactattt tgtagaatgg aagacatcaa   22980
cttttgcgtct ctggccccgc gacacggctc gcgcccgttc atgggaaact ggcaagatat  23040
cggcaccagc aatatgagcg gtggcgcctt cagctggggc tcgctgtgga gcggcattaa   23100
aaatttcggt tccaccgtta agaactatgg cagcaaggcc tggaacagca gcacaggcca   23160
gatgctgagg gataagttga agagcaaaa tttccaacaa aaggtggtag atggcctggc    23220
ctctggcatt agcggggtgg tggacctggc caaccaggca gtgcaaaata agattaacag   23280
taagcttgat ccccgccctc ccgtagagga gcctccaccg gccgtggaga cagtgtctcc   23340
agaggggcgt ggcgaaaagc gtccgcgccc cgacagggaa gaaactctgg tgacgcaaat   23400
agacgagcct ccctcgtacg aggaggcact aaagcaaggc ctgcccacca cccgtcccat   23460
cgcgcccatg gctaccggag tgctgggcca gcacacaccc gtaacgctgg acctgcctcc   23520
ccccgccgac acccagcaga aacctgtgct gccaggcccg accgccgttg ttgtaacccg   23580
tcctagccgc gcgtccctgc gccgcgccgc cagcggtccg cgatcgttgc ggcccgtagc   23640
cagtggcaac tggcaaagca cactgaacag catcgtgggt ctggggtgc aatccctgaa    23700
gcgccgacga tgcttctgaa tagctaacgt gtcgtatgtg tgtcatgtat cgtccatgt    23760
cgccgccaga ggagctgctg agccgccgcg cgcccgcttt ccaagatggc tacccttcg    23820
atgatgccgc agtggtctta catgcacatc tcgggccagg acgcctcgga gtacctgagc   23880
cccgggctgg tgcagtttgc ccgcgccacc gagacgtact tcagcctgaa taacaagttt   23940
agaaacccca cggtggcgcc tacgcacgac gtgaccacag accggtccca gcgtttgacg   24000
ctgcggttca tccctgtgga ccgtgaggat actgcgtact cgtacaaggc gcggttcacc   24060
ctagctgtgg gtgataaccg tgtgctggac atggcttcca cgtactttga catccgcggc   24120
gtgctggaca ggggccctac ttttaagccc tactctggca ctgcctacaa cgccctggct   24180
cccaagggtg ccccaaatcc ttgcgaatgg gatgaagctg ctactgctct tgaaataaac   24240
ctagaagaag aggacgatga caacgaagac gaagtagacg agcaagctga gcagcaaaaa   24300
actcacgtat ttgggcaggc gccttattct ggtataaata ttacaaagga gggtattcaa   24360
ataggtgtcg aaggtcaaac acctaaatat gccgataaaa catttcaacc tgaacctcaa   24420
ataggagaat ctcagtggta cgaaactgaa attaatcatg cagctgggag agtccttaaa   24480
aagactaccc caatgaaacc atgttacggt tcatatgcaa aacccacaaa tgaaaatgga   24540
gggcaaggca ttcttgtaaa gcaacaaaat ggaaagctag aaagtcaagt ggaaatgcaa   24600
tttttctcaa ctactgaggc gaccgcaggc aatggtgata acttgactcc taaagtggta   24660
ttgtacagtg aagatgtaga tatagaaacc ccagacactc atatttctta catgcccact   24720
attaaggaag gtaactcacg agaactaatg ggccaacaat ctatgcccaa caggcctaat   24780
tacattgctt ttagggacaa ttttattggt ctaatgtatt acaacagcac gggtaatatg   24840
ggtgttctgg cgggccaagc atcgcagttg aatgctgttg tagatttgca agacagaaac   24900
acagagcttt cataccagct tttgcttgat tccattggtg ataaccag gtacttttct     24960
atgtggaatc aggctgttga cagctatgat ccagatgtta gaattattga aaatcatgga   25020
actgaagatg aacttccaaa ttactgcttt ccactgggag gtgtgattaa tacagagact   25080
cttaccaagg taaaacctaa aacaggtcag gaaaatggat gggaaaaga tgctacagaa   25140
```

```
ttttcagata aaaatgaaat aagagttgga aataattttg ccatggaaat caatctaaat   25200
gccaacctgt ggagaaattt cctgtactcc aacatagcgc tgtatttgcc cgacaagcta   25260
aagtacagtc cttccaacgt aaaaatttct gataacccaa acacctacga ctacatgaac   25320
aagcgagtgg tggctcccgg gttagtggac tgctacatta accttggagc acgctggtcc   25380
cttgactata tggacaacgt caacccattt aaccaccacc gcaatgctgg cctgcgctac   25440
cgctcaatgt tgctgggcaa tggtcgctat gtgcccttcc acatccaggt gcctcagaag   25500
ttctttgcca ttaaaaacct ccttctcctg ccgggctcat acacctacga gtggaacttc   25560
aggaaggatg ttaacatggt tctgcagagc tccctaggaa atgacctaag ggttgacgga   25620
gccagcatta agtttgatag catttgcctt tacgccacct tcttcccat ggcccacaac    25680 accgcctcca cgcttgaggc catgcttaga aacgacacca acgaccagtc ctttaacgac   25740
tatctctccg ccgccaacat gctctaccct atacccgcca acgctaccaa cgtgcccata   25800
tccatcccct cccgcaactg ggcggctttc cgcggctggg ccttcacgcg ccttaagact   25860
aaggaaaccc catcactggg ctcgggctac gaccccttatt acacctactc tggctctata  25920
ccctacctag atggaacctt ttacctcaac cacacctta agaaggtggc cattacctttt  25980 gactcttctg tcagctggcc tggcaatgac cgcctgctta cccccaacga gtttgaaatt   26040
aagcgctcag ttgacgggga gggttacaac gttgcccagt gtaacatgac caaagactgg   26100
ttcctggtac aaatgctagc taactacaac attggctacc agggcttcta tatcccagag   26160
agctacaagg accgcatgta ctccttcttt taagaaacttcc agcccatgag ccgtcaggtg   26220
gtggatgata ctaaatacaa ggactaccaa caggtgggca tcctacacca acacaacaac   26280
tctggatttg ttggctacct tgcccccacc atgcgcgaag acaggccta ccctgctaac    26340 ttcccctatc cgcttatagg caagaccgca gttgacagca ttacccagaa aaagtttctt   26400
tgcgatcgca ccctttggcg catcccattc tccagtaact ttatgtccat gggcgcactc   26460
acagacctgg gccaaaacct tctctacgcc aactccgccc acgcgctaga catgactttt   26520
gaggtggatc ccatggacga gcccacccttt ctttatgttt tgtttgaagt ctttgacgtg   26580
gtccgtgtgc accggccgca ccgcggcgtc atcgaaaccg tgtacctgcg cacgcccttc   26640
tcggccggca acgccacaac ataaagaagc aagcaacatc aacaacagct gccgccatgg   26700
gctccagtga gcaggaactg aaagccattg tcaaagatct tggttgtggg ccatattttt   26760
tgggcaccta tgacaagcgc tttccaggct ttgtttctcc acacaagctc gcctgcgcca   26820
tagtcaatac ggccggtcgc gagactgggg gcgtacactg gatggccttt gcctggaacc   26880
cgcactcaaa aacatgctac ctcttttgagc ccttttggctt ttctgaccag cgactcaagc  26940
aggtttacca gtttgagtac gagtcactcc tgcgccgtag cgccattgct tcttcccccg   27000
accgctgtat aacgctggaa aagtccaccc aaagcgtaca ggggcccaac tcggccgcct   27060
gtggactatt ctgctgcatg tttctccacg cctttgccaa ctggcccaa actcccatgg    27120 atcacaaccc caccatgaac cttattaccg gggtacccaa ctccatgctc aacagtcccc   27180
aggtacagcc caccctgcgt cgcaaccagg aacagctcta cagcttcctg gagcgccact   27240
cgccctactt ccgcagccac agtgcgcaga ttaggagcgc cacttctttt tgtcacttga   27300
aaaacatgta aaaataatgt actagagaca cttcaataa aggcaaatgc ttttatttgt   27360
acactctcgg gtgattattt acccccaccc ttgccgtctg cgccgtttaa aaatcaaagg   27420
ggttctgccg cgcatcgcta tgcgccactg gcagggacac gttgcgatac tggtgtttag   27480
tgctccactt aaactcaggc acaaccatcc gcggcagctc ggtgaagttt tcactccaca   27540
```

```
ggctgcgcac catcaccaac gcgtttagca ggtcgggcgc cgatatcttg aagtcgcagt   27600
tggggcctcc gccctgcgcg cgcgagttgc gatacacagg gttgcagcac tggaacacta   27660
tcagcgccgg gtggtgcacg ctggccagca cgctcttgtc ggagatcaga tccgcgtcca   27720
ggtcctccgc gttgctcagg gcgaacggag tcaactttgg tagctgcctt cccaaaaagg   27780
gcgcgtgccc aggctttgag ttgcactcgc accgtagtgg catcaaaagg tgaccgtgcc   27840
cggtctgggc gttaggatac agccgcctgca taaaagcctt gatctgctta aaagccacct   27900
gagcctttgc gccttcagag aagaacatgc cgcaagactt gccggaaaac tgattggccg   27960
gacaggccgc gtcgtgcacg cagcaccttg cgtcggtgtt ggagatctgc accacatttc   28020
ggccccaccg gttcttcacg atcttggcct tgctagactg ctccttcagc gcgcgctgcc   28080
cgttttcgct cgtcacatcc atttcaatca cgtgctcctt atttatcata atgcttccgt   28140
gtagacactt aagctcgcct tcgatctcag cgcagcggtg cagccacaac gcgcagcccg   28200
tgggctcgtg atgcttgtag gtcacctctg caaacgactg caggtacgcc tgcaggaatc   28260
gccccatcat cgtcacaaag gtcttgttgc tggtgaaggt cagctgcaac ccgcggtgct   28320
cctcgttcag ccaggtcttg catacggccg ccagagcttc cacttggtca ggcagtagtt   28380
tgaagttcgc ctttagatcg ttatccacgt ggtacttgtc catcagcgcg cgcgcagcct   28440
ccatgccctt ctcccacgca gacacgatcg gcacactcag cgggttcatc accgtaattt   28500
cactttccgc ttcgctgggc tcttcctctt cctcttgcgt ccgcatacca cgcgccactg   28560
ggtcgtcttc attcagccgc cgcactgtgc gcttacctcc tttgccatgc ttgattagca   28620
ccggtgggtt gctgaaaccc accatttgta gcgccacatc ttctctttct tcctcgctgt   28680
ccacgattac ctctggtgat ggcgggcgct cgggcttggg agaagggcgc ttctttttct   28740
tcttgggcgc aatggccaaa tccgccgccg aggtcgatgg ccgcgggctg ggtgtgcgcg   28800
gcaccagcgc gtcttgtgat gagtcttcct cgtcctcgga ctcgatacgc cgcctcatcc   28860
gcttttttgg gggcgcccgg ggaggcggcg gcgacgggga cggggacgac acgtcctcca   28920
tggttggggg acgtcgcgcc gcaccgcgtc cgcgctcggg ggtggtttcg cgctgctcct   28980
cttcccgact ggccatttcc ttctcctata ggcagaaaaa gatcatggag tcagtcgaga   29040
agaaggacag cctaaccgcc ccctctgagt tcgccaccac cgcctccacc gatgccgcca   29100
acgcgcctac caccttcccc gtcgaggcac ccccgcttga ggaggaggaa gtgattatcg   29160
agcaggaccc aggttttgta agcgaagacg acgaggaccg ctcagtacca acagaggata   29220
aaaagcaaga ccaggacaac gcagaggcaa acgaggaaca agtcgggcgg ggggacgaaa   29280
ggcatggcga ctacctagat gtgggagacg acgtgctgtt gaagcatctg cagcgccagt   29340
gcgccattat ctgcgacgcg ttgcaagagc gcagcgatgt gccctcgcc atagcggatg    29400 tcagccttgc ctacgaacgc cacctattct caccgcgcgt accccccaaa cgccaagaaa   29460
acggcacatg cgagcccaac ccgcgcctca acttctaccc cgtatttgcc gtgccagagg   29520
tgcttgccac ctatcacatc ttttccaaa actgcaagat acccctatcc tgccgtgcca    29580
accgcagccg agcggacaag cagctggcct tgcggcaggg cgctgtcata cctgatatcg   29640
cctcgctcaa cgaagtgcca aaaatctttg agggtcttgg acgcgacgag aagcgcgcgg   29700
caaacgctct gcaacaggaa aacagcgaaa atgaaagtca ctctggagtg ttggtggaac   29760
tcgagggtga caacgcgcgc ctagccgtac taaaacgcag catcgaggtc acccactttg   29820
cctacccggc acttaaccta ccccccaagg tcatgacac agtcatgagt gagctgatcc    29880
tgcgccgtgc gcagcccctg gagagggatg caaatttgca agaacaaaca gaggagggcc   29940
```

```
tacccgcagt tggcgacgag cagctagcgc gctggcttca aacgcgcgag cctgccgact   30000
tggaggagcg acgcaaacta atgatggccg cagtgctcgt taccgtggag cttgagtgca   30060
tgcagcggtt ctttgctgac ccggagatgc agcgcaagct agaggaaaca ttgcactaca   30120
cctttcgaca gggctacgta cgccaggcct gcaagatctc aacgtggag ctctgcaacc    30180 tggtctccta ccttggaatt ttgcacgaaa accgccttgg gcaaaacgtg cttcattcca   30240
cgctcaaggg cgaggcgcgc cgcgactacg tccgcgactg cgtttactta tttctatgct   30300
acacctggca gacggccatg ggcgtttggc agcagtgctt ggaggagtgc aacctcaagg   30360
agctgcagaa actgctaaag caaaacttga aggacctatg gacggccttc aacgagcgct   30420
ccgtggccgc gcacctggcg gacatcattt tccccgaacg cctgcttaaa accctgcaac   30480
agggtctgcc agacttcacc agtcaaagca tgttgcagaa ctttaggaac tttatcctag   30540
agcgctcagg aatcttgccc gccacctgct gtgcacttcc tagcgactt gtgcccatta    30600 agtaccgcga atgccctccg ccgctttggg gccactgcta ccttctgcag ctagccaact   30660
accttgccta ccactctgac ataatggaag acgtgagcgg tgacggtcta ctggagtgtc   30720
actgtcgctg caacctatgc accccgcacc gctccctggt ttgcaattcg cagctgctta   30780
acgaaagtca aattatcggt accttt gagc tgcagggtcc ctcgcctgac gaaaagtccg   30840
cggctccggg gttgaaactc actccggggc tgtggacgtc ggcttacctt cgcaaatttg   30900
tacctgagga ctaccacgcc cacgagatta ggttctacga agaccaatcc cgcccgccaa   30960
atgcggagct taccgcctgc gtcattaccc agggccacat tcttggccaa ttgcaagcca   31020
tcaacaaagc ccgccaagag tttctgctac gaaagggacg gggggttac ttggacccc     31080 agtccggcga ggagctcaac ccaatccccc cgccgccgca gccctatcag cagcagcgc    31140 gggcccttgc ttcccaggat ggcacccaaa aagaagctgc agctgccgcc gccacccacg   31200
gacgaggagg aatactggga cagtcaggca gaggaggttt tggacgagga ggaggaggac   31260
atgatggaag actgggagag cctagacgag gaagcttccg aggtcgaaga ggtgtcagac   31320
gaaacaccgt cacctcggt cgcattcccc tcgccggcgc cccagaaatc ggcaaccggt    31380
tccagcatgg ctacaacctc cgctcctcag gcgccgccgg cactgcccgt tcgccgaccc   31440
aaccgtagat gggacaccac tggaaccagg gccggtaagt ccaagcagcc gccgccgtta   31500
gcccaagagc aacaacagcg ccaaggctac cgctcatggc gcgggcacaa gaacgccata   31560
gttgcttgct tgcaagactg tggggcaac atctccttcg cccgccgctt tcttctctac    31620
catcacggcg tggccttccc ccgtaacatc ctgcattact accgtcatct ctacagccca   31680
tactgcaccg gcggcagcgg cagcggcagc aacagcagcg gccacacaga agcaaaggcg   31740
accggatagc aagactctga caaagcccaa gaaatccaca gcggcggcag cagcaggagg   31800
aggagcgctg cgtctggcgc ccaacgaacc cgtatcgacc cgcgagctta gaaacaggat   31860
ttttcccact ctgtatgcta tatttcaaca gagcaggggc caagaacaag agctgaaaat   31920
aaaaaacagg tctctgcgat ccctcacccg cagctgcctg tatcacaaaa gcgaagatca   31980
gcttcggcgc acgctggaag acgcggaggc tctcttcagt aaatactgcg cgctgactct   32040
taaggactag tttcgcgccc tttctcaaat ttaagcgcga aaactacgtc atctccagcg   32100
gccacacccg cgccagcac ctgtcgtcag cgccattatg agcaaggaaa ttcccacgcc    32160
ctacatgtgg agttaccagc cacaaatggg acttgcggct ggagctgccc aagactactc   32220
aacccgaata aactacatga gcgcgggacc ccacatgata tcccgggtca acggaatccg   32280
cgcccaccga aaccgaattc tcttggaaca ggcggctatt accaccacac ctcgtaataa   32340
```

```
ccttaatccc cgtagttggc ccgctgccct ggtgtaccag gaaagtcccg ctcccaccac    32400
tgtggtactt cccagagacg cccaggccga agttcagatg actaactcag gggcgcagct    32460
tgcgggcggc tttcgtcaca gggtgcggtc gcccgggcag ggtataactc acctgacaat    32520
cagagggcga ggtattcagc tcaacgacga gtcggtgagc tcctcgcttg gtctccgtcc    32580
ggacgggaca tttcagatcg gcggcgccgg ccgtccttca ttcacgcctc gtcaggcaat    32640
cctaactctg cagacctcgt cctctgagcc gcgctctgga ggcattggaa ctctgcaatt    32700
tattgaggag tttgtgccat cggtctactt taacccttc tcgggacctc ccggccacta     32760
tccggatcaa tttattccta actttgacgc ggtaaaggac tcggcggacg gctacgactg    32820
aatgttaagt ggagaggcag agcaactgcg cctgaaacac ctggtccact gtcgccgcca    32880
caagtgcttt gcccgcgact ccggtgagtt ttgctacttt gaattgcccg aggatcatat    32940
cgagggcccg gcgcacggcg tccggcttac cgcccaggga gagcttgccc gtagcctgat    33000
tcgggagttt acccagcgcc ccctgctagt tgagcggac aggggaccct gtgttctcac     33060
tgtgatttgc aactgtccta accttggatt acatcaagat cctctagtta taactagagt    33120
acccggggat cttattccct ttaactaata aaaaaaata ataaagcatc acttacttaa     33180
aatcagttag caaatttctg tccagttat tcagcagcac ctccttgccc tcctcccagc     33240
tctggtattg cagcttcctc ctggctgcaa actttctcca caatctaaat ggaatgtcag    33300
tttcctcctg ttcctgtcca tccgcaccca ctatcttcat gttgttgcag atgaagcgcg    33360
caagaccgtc tgaagatacc ttcaaccccg tgtatccata tgacacggaa accggtcctc    33420
caactgtgcc ttttcttact cctcccttg tatccccaa tgggtttcaa gagagtcccc      33480
ctggggtact ctctttgcgc ctatccgaac ctctagttac ctccaatggc atgcttgcgc    33540
tcaaaatggg caacggcctc tctctggacg aggccggcaa ccttacctcc caaaatgtaa    33600
ccactgtgag cccacctctc aaaaaaacca agtcaaacat aaacctggaa atatctgcac    33660
ccctcacagt tacctcagaa gccctaactg tggctgccgc cgcacctcta atggtcgcgg    33720
gcaacacact caccatgcaa tcacaggccc cgctaaccgt gcacgactcc aaacttagca    33780
ttgccaccca aggacccctc acagtgtcag aaggaaagct agccctgcaa acatcaggcc    33840
ccctcaccac caccgatagc agtaccctta ctatcactgc ctcacccct ctaactactg     33900 ccactggtag cttgggcatt gacttgaaag agcccattta tacacaaaat ggaaaactag    33960
gactaaagta cggggctcct ttgcatgtaa cagacgacct aaacactttg accgtagcaa    34020
ctggtccagg tgtgactatt aataatactt ccttgcaaac taaagttact ggagccttgg    34080
gttttgattc acaaggcaat atgcaactta atgtagcagg aggactaagg attgattctc    34140
aaaacagacg ccttatactt gatgttagtt atccgtttga tgctcaaaac caactaaatc    34200
taagactagg acagggccct cttttataa actcagccca caactggat attaactaca      34260 acaaaggcct ttacttgttt acagcttcaa acaattccaa aaagcttgag gttaacctaa    34320
gcactgccaa ggggttgatg tttgacgcta cagccatagc cattaatgca ggagatgggc    34380
ttgaatttgg ttcacctaat gcaccaaaca caaatcccct caaaacaaaa attggccatg    34440
gcctagaatt tgattcaaac aaggctatgg ttcctaaact aggaactggc cttagttttg    34500
acagcacagg tgccattaca gtaggaaaca aaaataatga taagctaact ttgtggacca    34560
caccagctcc atctcctaac tgtagactaa atgcagagaa agatgctaaa ctcactttgg    34620
tcttaacaaa atgtggcagt caaatacttg ctacagtttc agtttggct gttaaaggca     34680 gtttggctcc aatatctgga acagttcaaa gtgctcatct tattataaga tttgacgaaa    34740
```

```
atggagtgct actaaacaat tccttcctgg acccagaata ttggaacttt agaaatggag   34800
atcttactga aggcacagcc tatacaaacg ctgttggatt tatgcctaac ctatcagctt   34860
atccaaaatc tcacggtaaa actgccaaaa gtaacattgt cagtcaagtt tacttaaacg   34920
gagacaaaac taaacctgta acactaacca ttacactaaa cggtacacag gaaacaggag   34980
acacaactcc aagtgcatac tctatgtcat tttcatggga ctggtctggc cacaactaca   35040
ttaatgaaat atttgccaca tcctcttaca cttttttcata cattgcccaa gaataaagaa   35100
tcgtttgtgt tatgtttcaa cgtgtttatt tttcaattgc agaaaatttc aagtcatttt   35160
tcattcagta gtatagcccc accaccacat agcttataca gatcaccgta ccttaatcaa   35220
actcacagaa ccctagtatt caacctgcca cctccctccc aacacacaga gtacacagtc   35280 cttctcccc ggctggcctt aaaaagcatc atatcatggg taacagacat attcttaggt   35340
gttatattcc acacggtttc ctgtcgagcc aaacgctcat cagtgatatt aataaactcc   35400
ccgggcagct cacttaagtt catgtcgctg tccagctgct gagccacagg ctgctgtcca   35460
acttgcggtt gcttaacggg cggcgaagga gaagtccacg cctacatggg ggtagagtca   35520
taatcgtgca tcaggatagg gcggtggtgc tgcagcagcg cgcgaataaa ctgctgccgc   35580
cgccgctccg tcctgcagga atacaacatg gcagtggtct cctcagcgat gattcgcacc   35640
gcccgcagca taaggcgcct tgtcctccgg gcacagcagc gcaccctgat ctcacttaaa   35700
tcagcacagt aactgcagca cagcaccaca atattgttca aaatcccaca gtgcaaggcg   35760
ctgtatccaa agctcatggc ggggaccaca gaacccacgt ggccatcata ccacaagcgc   35820
aggtagatta agtggcgacc cctcataaac acgctggaca taaacattac ctcttttggc   35880
atgttgtaat tcaccacctc ccggtaccat ataaacctct gattaaacat ggcgccatcc   35940
accaccatcc taaaccagct ggccaaaacc tgcccgccgg ctatacactg cagggaaccg   36000
ggactggaac aatgacagtg gagagcccag gactcgtaac catggatcat catgctcgtc   36060
atgatatcaa tgttggcaca acacaggcac acgtgcatac acttcctcag gattacaagc   36120
tcctcccgcg ttagaaccat atcccaggga acaacccatt cctgaatcag cgtaaatccc   36180
acactgcagg gaagacctcg cacgtaactc acgttgtgca ttgtcaaagt gttacattcg   36240
ggcagcagcg gatgatcctc cagtatggta gcgcgggttt ctgtctcaaa aggaggtaga   36300
cgatccctac tgtacggagt gcgccgagac aaccgagatc gtgttggtcg tagtgtcatg   36360
ccaaatggaa cgccggacgt agtcatattt cctgaagcaa aaccaggtgc gggcgtgaca   36420
aacagatctg cgtctccggt ctcgccgctt agatcgctct gtgtagtagt tgtagtatat   36480
ccactctctc aaagcatcca ggcgccccct ggcttcgggt tctatgtaaa ctccttcatg   36540
cgccgctgcc ctgataacat ccaccaccgc agaataagcc acacccagcc aacctacaca   36600
ttcgttctgc gagtcacaca cgggaggagc gggaagagct ggaagaacca tgttttttt   36660 tttattccaa aagattatcc aaaacctcaa aatgaagatc tattaagtga acgcgctccc   36720
ctccggtggc gtggtcaaac tctacagcca agaacagat aatggcattt gtaagatgtt   36780
gcacaatggc ttccaaaagg caaacggccc tcacgtccaa gtggacgtaa aggctaaacc   36840
cttcagggtg aatctcctct ataaacattc cagcaccttc aaccatgccc aataattct   36900 catctcgcca ccttctcaat atatctctaa gcaaatcccg aatattaagt ccggccattg   36960
taaaaatctg ctccagagcg ccctccacct tcagcctcaa gcagcgaatc atgattgcaa   37020
aaattcaggt tcctcacaga cctgtataag attcaaaagc ggaacattaa caaaaatacc   37080
gcgatcccgt aggtccccttc gcagggccag ctgaacataa tcgtgcaggt ctgcacggac   37140
```

```
cagcgcggcc acttccccgc caggaacctt gacaaaagaa cccacactga ttatgacacg    37200
catactcgga gctatgctaa ccagcgtagc cccgatgtaa gctttgttgc atgggcggcg    37260
atataaaatg caaggtgctg ctcaaaaaat caggcaaagc ctcgcgcaaa aaagaaagca    37320
catcgtagtc atgctcatgc agataaaggc aggtaagctc cggaaccacc acagaaaaag    37380
acaccatttt tctctcaaac atgtctgcgg gtttctgcat aaacacaaaa taaaataaca    37440
aaaaaacatt taaacattag aagcctgtct tacaacagga aaaacaaccc ttataagcat    37500
aagacggact acggccatgc cggcgtgacc gtaaaaaaac tggtcaccgt gattaaaaag    37560
caccaccgac agctcctcgg tcatgtccgg agtcataatg taagactcgg taaacacatc    37620
aggttgattc atcggtcagt gctaaaaagc gaccgaaata gcccggggga atacataccc    37680
gcaggcgtag agacaacatt acagccccca taggaggtat aacaaaatta ataggagaga    37740
aaaacacata aacacctgaa aaaccctcct gcctaggcaa aatagcaccc tcccgctcca    37800
gaacaacata cagcgcttca cagcggcagc ctaacagtca gccttaccag taaaaaagaa    37860
aacctattaa aaaaacacca ctcgacacgg caccagctca atcagtcaca gtgtaaaaaa    37920
gggccaagtg cagagcgagt atatatagga ctaaaaatg acgtaacggt taaagtccac    37980
aaaaaacacc cagaaaaccg cacgcgaacc tacgcccaga aacgaaagcc aaaaaaccca    38040
caacttcctc aaatcgtcac ttccgttttc ccacgttacg taacttccca ttttaagaaa    38100
actacaattc ccaacacata caagttactc cgccctaaaa cctacgtcac ccgccccgtt    38160
cccacgcccc gcgccacgtc acaaactcca cccctcatt atcatattgg cttcaatcca    38220
aaataaggta tattattgat gatnnn                                        38246
```

VIRAL VECTORS AND THE USE OF THE SAME FOR GENE THERAPY

CROSS-REFERENCE TO RELATED APPLICATIONS

This application is a national phase application under 35 U.S.C. §371 of International Application Number PCT/EP03/011252, filed Oct. 10, 2003, the disclosure of which is hereby incorporated by reference in its entirety, and claims the benefit of German Patent Application Number 102 48 141.5, filed Oct. 11, 2002.

INCORPORATION OF SEQUENCE LISTING

A paper copy of the Sequence Listing is herein incorporated by reference in its entirety.

BACKGROUND OF THE INVENTION

The present invention relates to viral vectors comprising nucleic acid sequences coding for single chain interleukin-12 (single chain IL-12 or scIL-12) and a costimulator protein, and to the use of said vectors for gene therapy, especially for the treatment of tumors.

Tumors are still one of the most common causes of death of human beings living in industrialized countries. For example, the hepatocellular carcinoma (HCC) is a tumor with an average survival rate of 6 months after diagnosis of one or several larger tumors (Llovet J. M. et al., Hepatology, 1999, 29: 62-67). The currently used therapies, comprising radio frequency ablation, chemotherapy and percutaneous ethanol injection (PEI) result in some success, when treating smaller tumors, but they are insufficient to fight large tumors.

In the prior art, therefore it was suggested to treat HCC by means of gene therapy. Gene therapeutic treatments are based on the administration of a nucleic acid that is usually incorporated into the tumor cell, and has a sequence that destroys the tumor cell. To this end, a multitude of different strategies has been developed that will effect a destruction of tumor cells caused by the transferred nucleic acid sequences. An overview of such strategies for the treatment of HCC can be found in Ruiz et al., (Dig. Dis. 2001, 19:324-332). In this publication, the nucleic acids currently used in clinical trials for the treatment of HCC in humans, are categorized into one of the four following groups, according to the treatment strategy:

(1) Transfer of Tumor Suppressor Genes:
   This strategy is based on the fact that the nucleic acid used for gene therapy contains a gene, which encodes a gene product that inhibits growth of the tumor or that induces apoptosis in the tumor cells. Most clinical trials are based on the transfer of the p53 gene.
(2) Therapy Using Immune Genes
   This strategy is based on the fact that the nucleic acids used for gene therapy comprises sequences encoding gene products that stimulate the patient's immune system and induce an immune response directed against the tumor cells. The immune response itself finally results in the destruction of the tumor. Numerous cytokines, costimulator molecules and tumor-specific molecules have been suggested for the use in a therapy using immune genes.
(3) Therapy Using Suicide Genes
   In this procedure, the nucleic acid used for gene therapy encodes a gene product, for example an enzyme, which transforms a non-toxic compound into an agent that is cytotoxic for the tumor cell.
(4) Transfer of Oncolytic Viruses
   In this variation of gene therapy, nucleic acid vectors are used that are based on viral sequences. Vectors with oncolytic viral sequences have a tumor-specific promoter that regulates the replication of the virus, thus enabling selective viral growth in the tumor cells.

During the therapy using immune genes (also called immunotherapy) that is relevant for the current application, nucleic acids are administered that comprise sequences, which activate the immune system and are directed against the tumor. As a general property, the immune system does not only recognize antigens but also tumor-specific structures on tumor cells. Therefore, the activation of the immune system can result in the destruction of the tumor caused by components of the immune system.

According to prior art, numerous molecules are known that stimulate the immune system or modulate an immune reaction, in particular the cytokines. It was recognized very early that cytokines also have anti-tumor activities. For example, it was reported that IL-12 is a stimulator of the cellular immunity and that it exhibits strong anti-tumor activity (Brunda et al., J. Exp. Med. 1993, 178: 1223-1230). However, the administration of the recombinant IL-12 protein itself as an anti-tumor-agent failed due to the toxic side-effects of the cytokine when used in therapeutically relevant doses (Lotze et al., Ann. N.Y. Acad. Sci., 1997, 795: 440-454; and Cohen J., Science, 1995, 270: 908).

Therefore, it was suggested to introduce a nucleic acid encoding a cytokine into the tumor, thus enabling a local activation of the immune system. Hock et al. (Proc. Natl. Acad. Sci. USA, 1993, 90: 2774-2778) for example, describe the transfer of the interleukin-2 (IL-2), interleukin-4 (IL-4), interleukin-7 (IL-7), TNF or IFN-γ gene into tumor cell lines and the use of these tumor cell lines for the induction of tumors in animals. All transgenic tumor cell lines generated a rejection reaction against the tumor cells. Dependent on the cytokine used, different cell types of the immune system of the laboratory animals were involved in this rejection reaction ($CD4^+$, $CD8^+$, $CD3^+$).

Vectors coding for IL-12 were also tested for their suitability in immunotherapy. IL-12, also known as CMLF (cytotoxic lymphocyte maturation factor) or NKSF (natural killer cell stimulatory factor), is a heterodimeric cytokine, which is naturally produced by activated peripheral B-lymphocytes. The protein consists of two subunits with relative molecular weights of 40 and 35 kDa, respectively, that are covalently linked by disulfide bridges. The disulfide bridges are essential for the biological activity. As already indicated by the different names, the protein stimulates the proliferation of activated human lyphoblasts and activates natural killer cells.

Vectors coding for the different subunits of this protein were used for the treatment of tumors (Barajas et al., Hepatology, 2001, 33: 52-61; Mazzolini et al., Cancer Gene Therapy, 1999, 6: 514-522). Furthermore, these vectors were used in combination with other sequences for immunotherapy. In particular, they were used in combination with sequences coding for a costimulator protein, contained within the same or in a different vector, for the treatment of tumors (Gyorffy et al., J. Immunology, 2001, 166: 6212-6217; Martinet et al., Gene Therapy, 2002, 9: 786-792; Martinet et al., Journal of National Cancer Institute, 2000, 92: 931-936; Guinn et al., J. Immunology, 1999, 162: 5003-5010; and Emtage et al., J. Immunology, 1998, 160: 2531-2538).

Further, IL-12 has already been expressed as single chain IL-12, yielding good activity, such as a protein comprising the different subunits linked together in one fusion protein (Lieschke et al., Nature Biotechnology, 1997, 15: 35-40). In a different therapeutic procedure it was suggested to remove tumor cells from the patient and treat these cells in vitro with a plasmid coding for single chain IL-12 or IL-12 and a costimulator (US 2002/0018767). Following this in vitro treatment the tumor cells shall be re-implanted into the patient. This procedure, therefore, comprises several operations on the patient and a re-implantation of tumor cells into the patient, which is likely to prevent many patients from undergoing such a treatment.

None of the previously used nucleic acids could prevail in the treatment of mammals, preferably in the treatment of humans. Although, for example, the publication by Ruiz et al (loc. cit.) described treatment procedures involving a very high dosage of the vector used for therapy ($3 \times 10^9 – 2.5 \times 10^{13}$ plaque forming units, PFU, per dose), it was observed that none or only negative results were obtained in the corresponding clinical trials. However, especially the dose of the nucleic acids is a critical factor in gene therapy, because negative side effects or the release of the vector from the tumor are expected when doses are used that are too high.

SUMMARY OF THE INVENTION

The problem of the present invention, therefore, was to provide vectors that can be used for immunotherapy with improved efficiency.

This problem was surprisingly solved by using viral vectors comprising nucleic acid sequences which code for single chain IL-12 and a costimulator protein, wherein the vector is a viral vector.

BRIEF DESCRIPTION OF THE DRAWINGS

FIG. 2 shows the time course of the expression over 3 days in the rat hepatoma cells McA-RH7777.

Procedure: McA-RH7777 cells were infected at MOIs of 10 with Ad-1, Ad-2 or Ad-3. The supernatants were collected at days 0, 1, 2 and 3 after infection. scIL-12 concentrations were determined by ELISA with an anti-mouse IL-12p70 antibody (Pharmingen).

Figure 3:
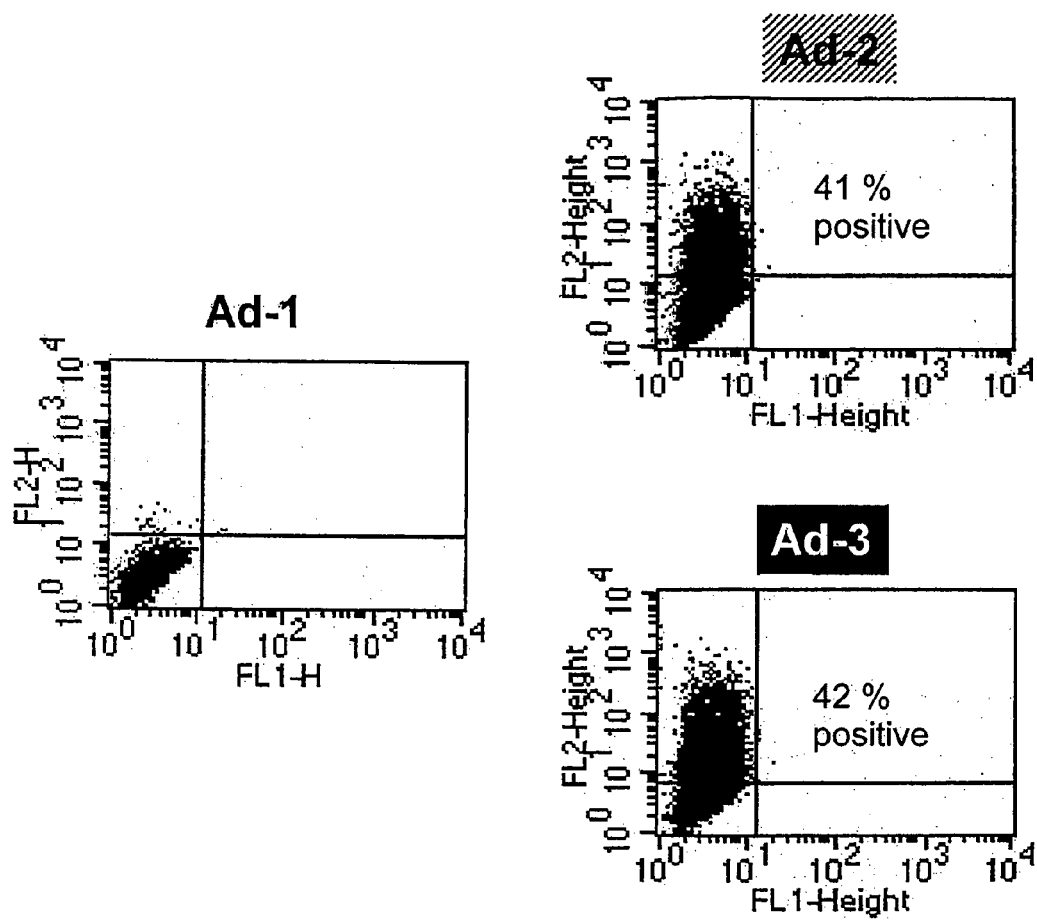

FIG. 3 Detection of 4-1BBL in the McA-RH7777 cell cultures. Flow-through cytometric determination of the 4-1BBL expression. 4-1BBL is expressed by Ad-2 and Ad-3, but not by Ad-1.

Procedure: McA-RH7777 cells were infected with the adjusted virus concentrations at MOI 10 with Ad-1, Ad-2 or Ad-3. The cells were harvested 24 h post-infection and were incubated with a rat anti-mouse 4-1BBL monoclonal antibody (TKS-1, Pharmingen) and stained with R-PE-conjugated goat anti-rat Ig polyclonal antibody (Pharmingen) for detection.

Figure 4:
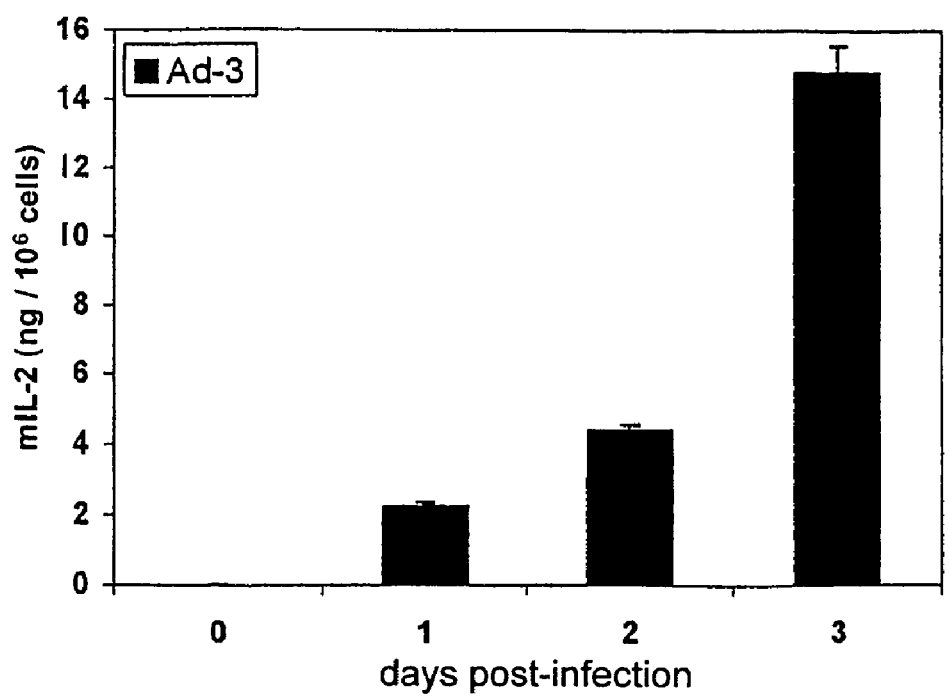

FIG. 4 Expression of IL-2 in the McA-RH7777 cell cultures over 3 days. In molar terms Ad-3 expresses 466-fold more IL-12 than IL-2 (calculated for day 3).

Procedure: McA-RH7777 cells were infected with Ad-3 at MOI 10. The supernatants were collected at days 0, 1, 2 and 3 post-infection. IL-2 concentrations were determined by ELISA using an anti-mouse IL-2 antibody (Pharmingen).

Figure 5:
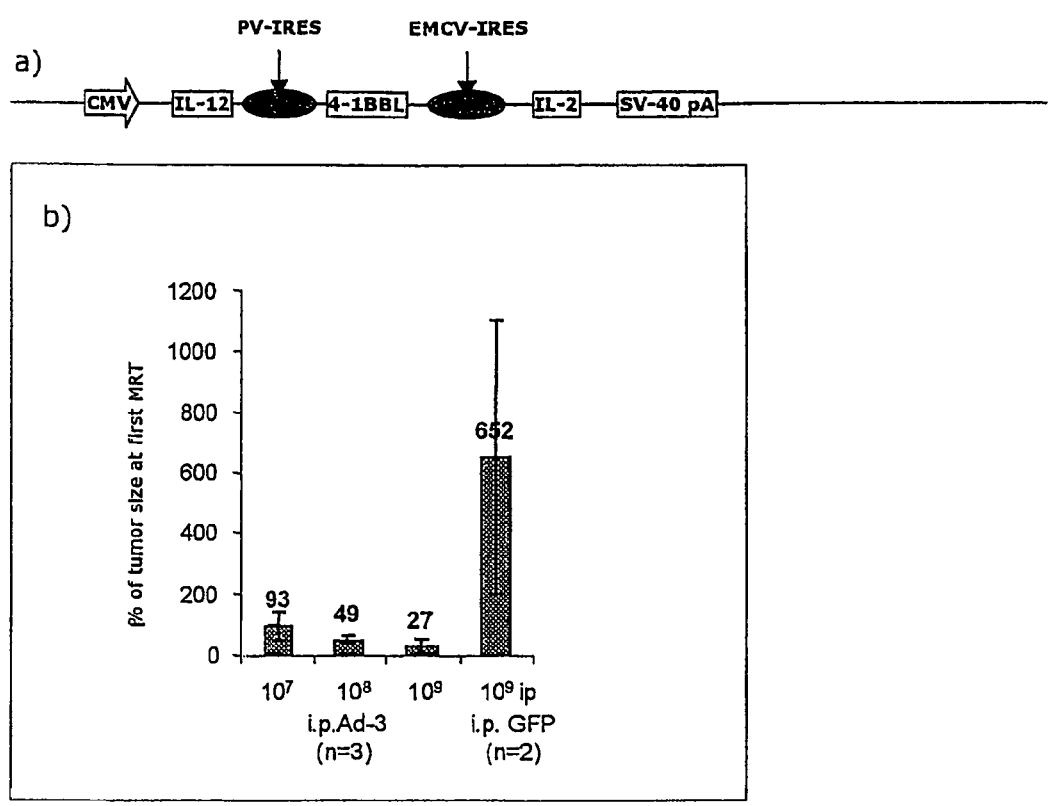

FIG. 5 Dose escalation study. Change of the tumor size within 9 days after treatment with Ad-3.

Procedure: The tumor volumes were measured by magnetic resonance tomography (MRT) within a time interval of 9 days. The reference value of 100% refers to the tumor size at day 3 after virus injection (1. MRT) the final size shown here was measured at day 12 after virus administration (2. MRT). The vector Ad-3 (a) was injected at the indicated doses (i.p.=infectious particles) into tumors of a size between 7 and 11 mm in diameter (b).

Figure 6:
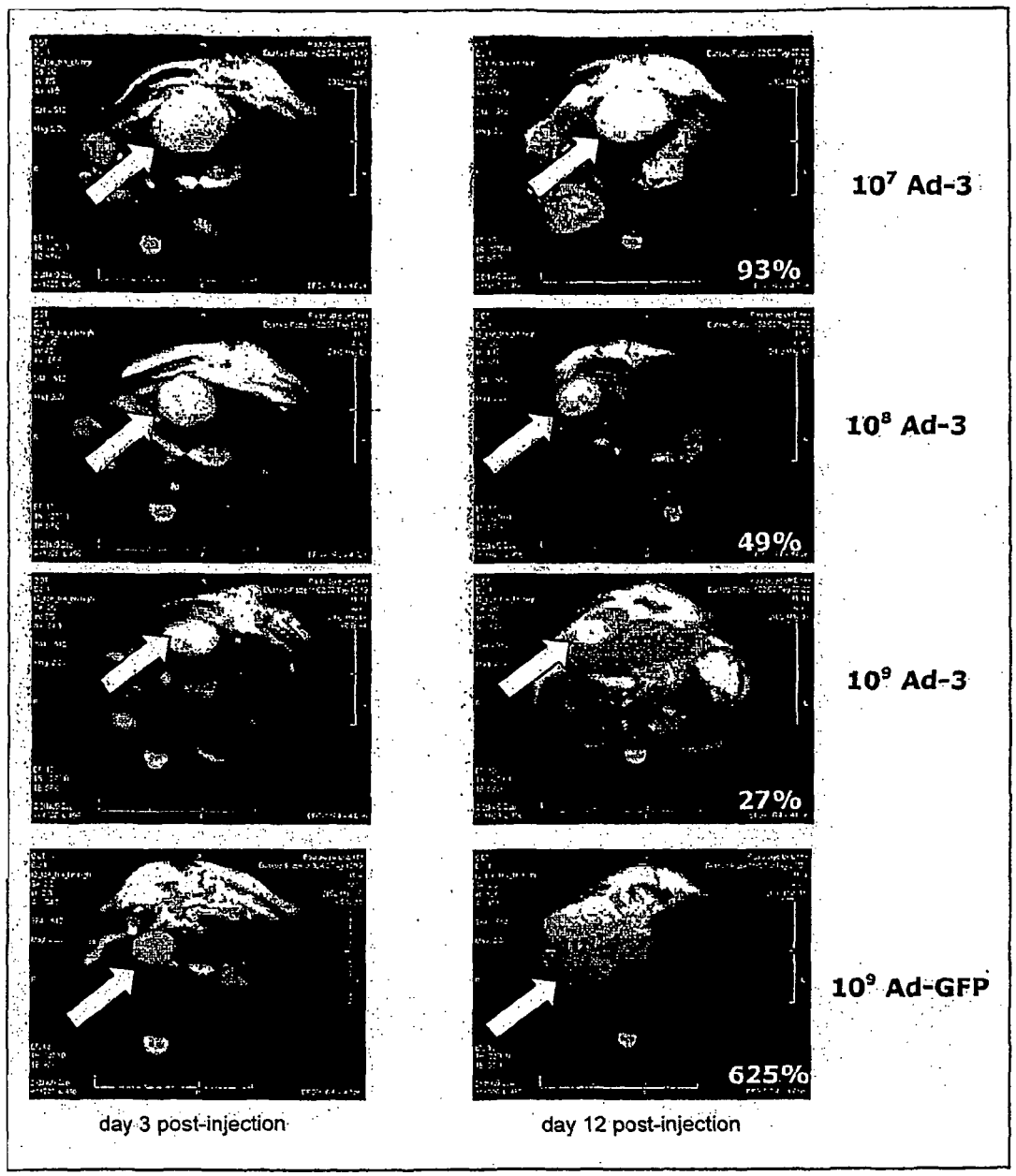

FIG. 6 MRT images of the dose escalation study.

Procedure: Tumors that were treated with $10^7$ to $10^9$ infectious virus particles of Ad-3 or with $10^9$ infectious particles of Ad-GFP (negative control), respectively, were scanned by MRT at day 3 and day 12 post-injection.

Figure 7:
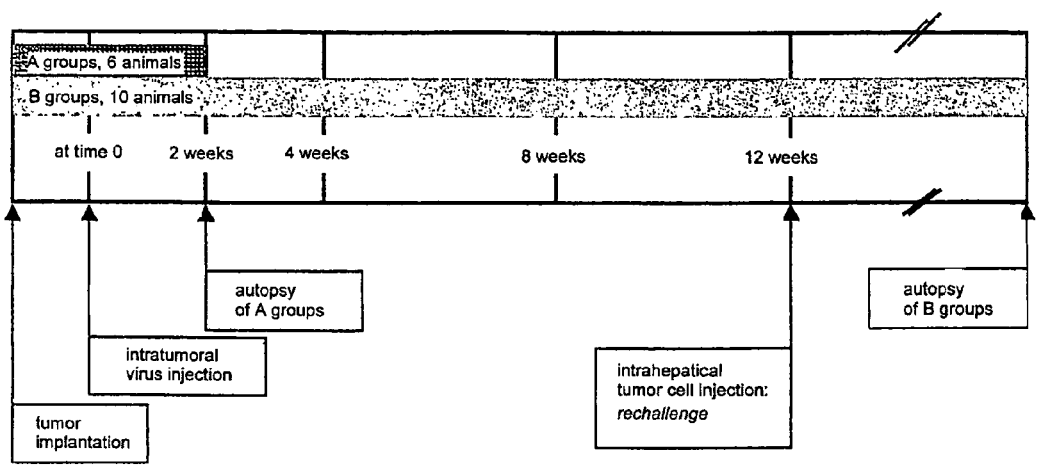

FIG. 7 Schematic illustration of the procedure of the animal experiments using Ad-1, Ad-2 and Ad-3.

Figure 8:
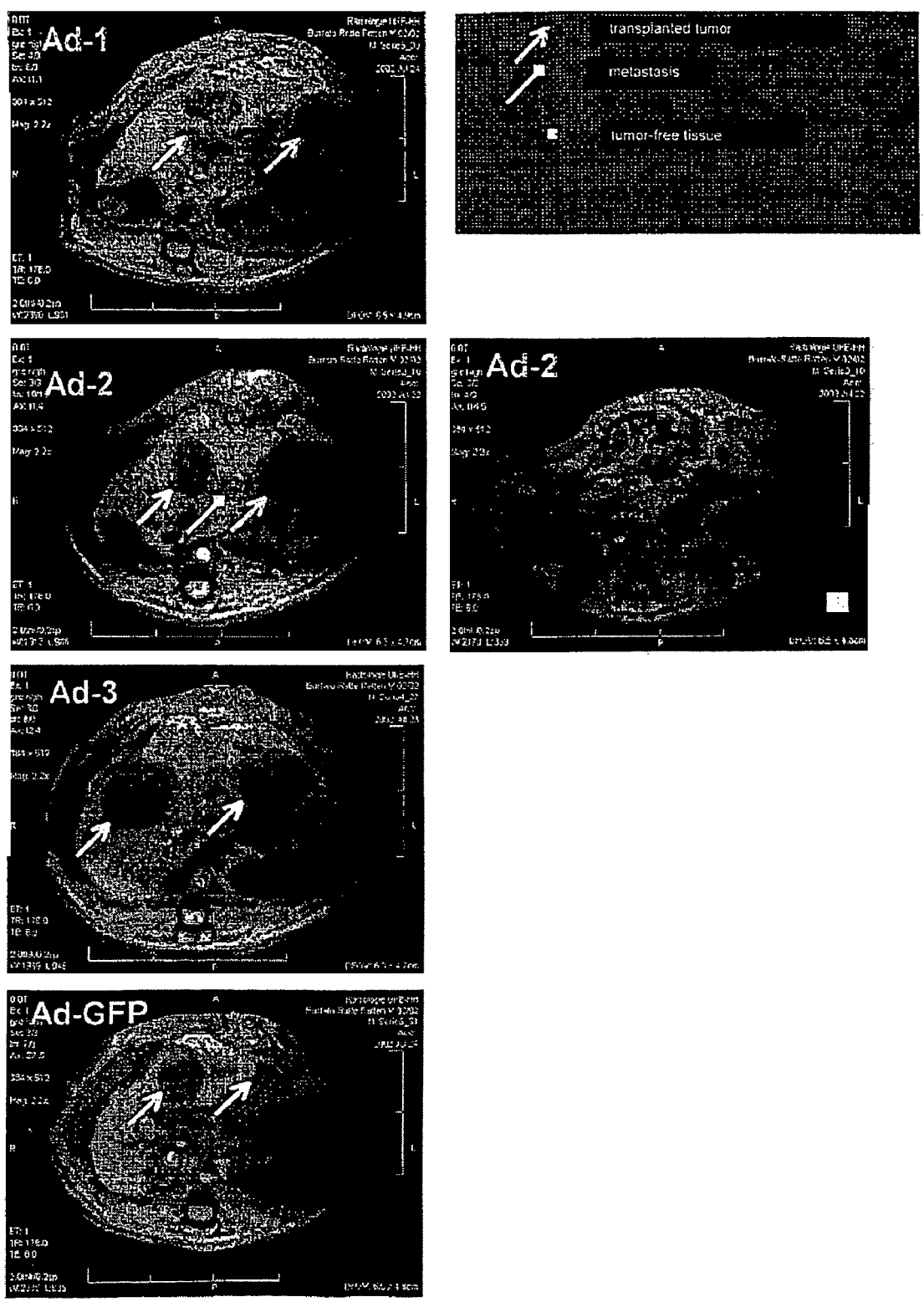

FIG. 8 MRT images of the tumors before the virus injection, week 0.

Figure 9:
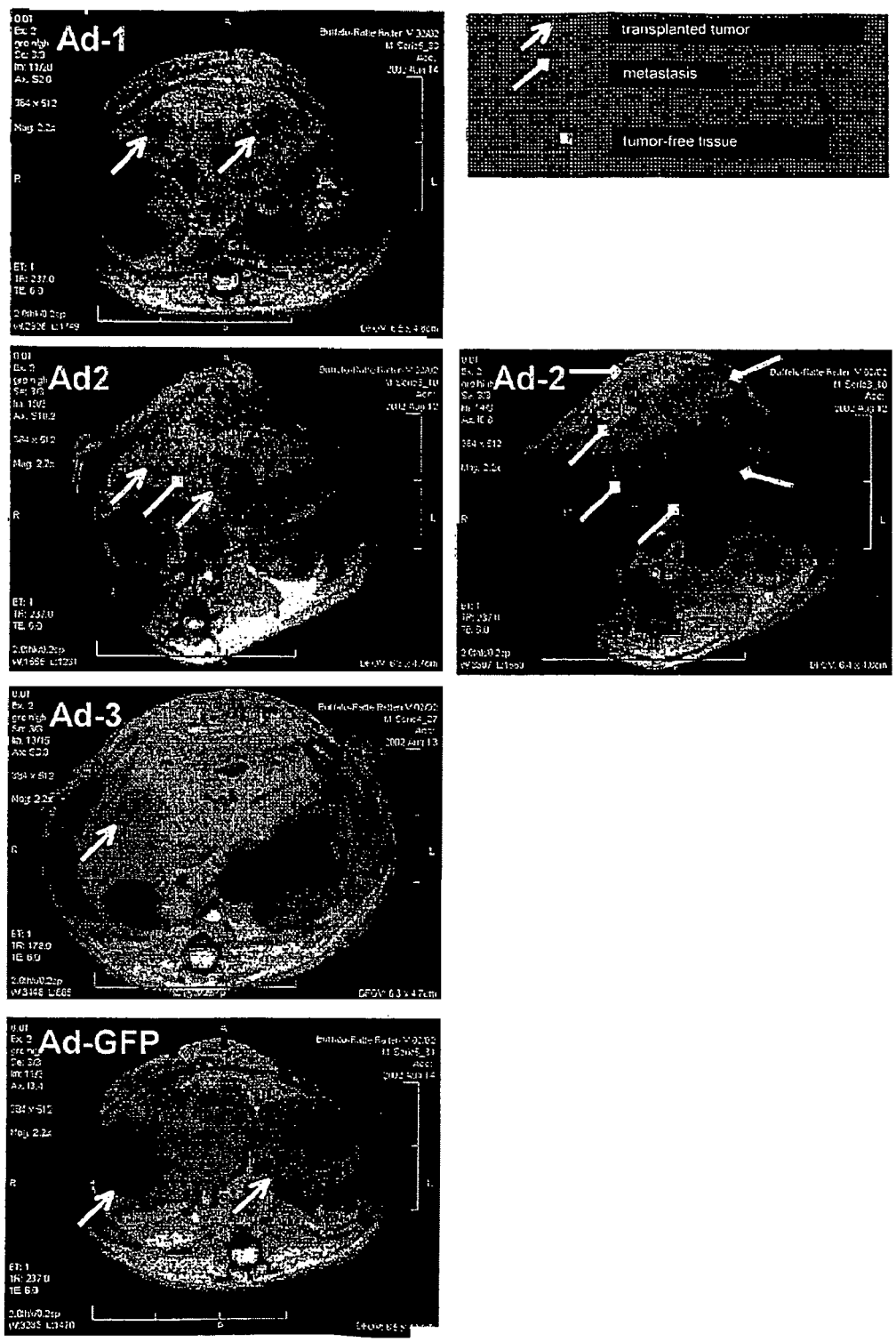

FIG. 9 MRT images of the tumors after the virus injection, week 3.

Figure 10:
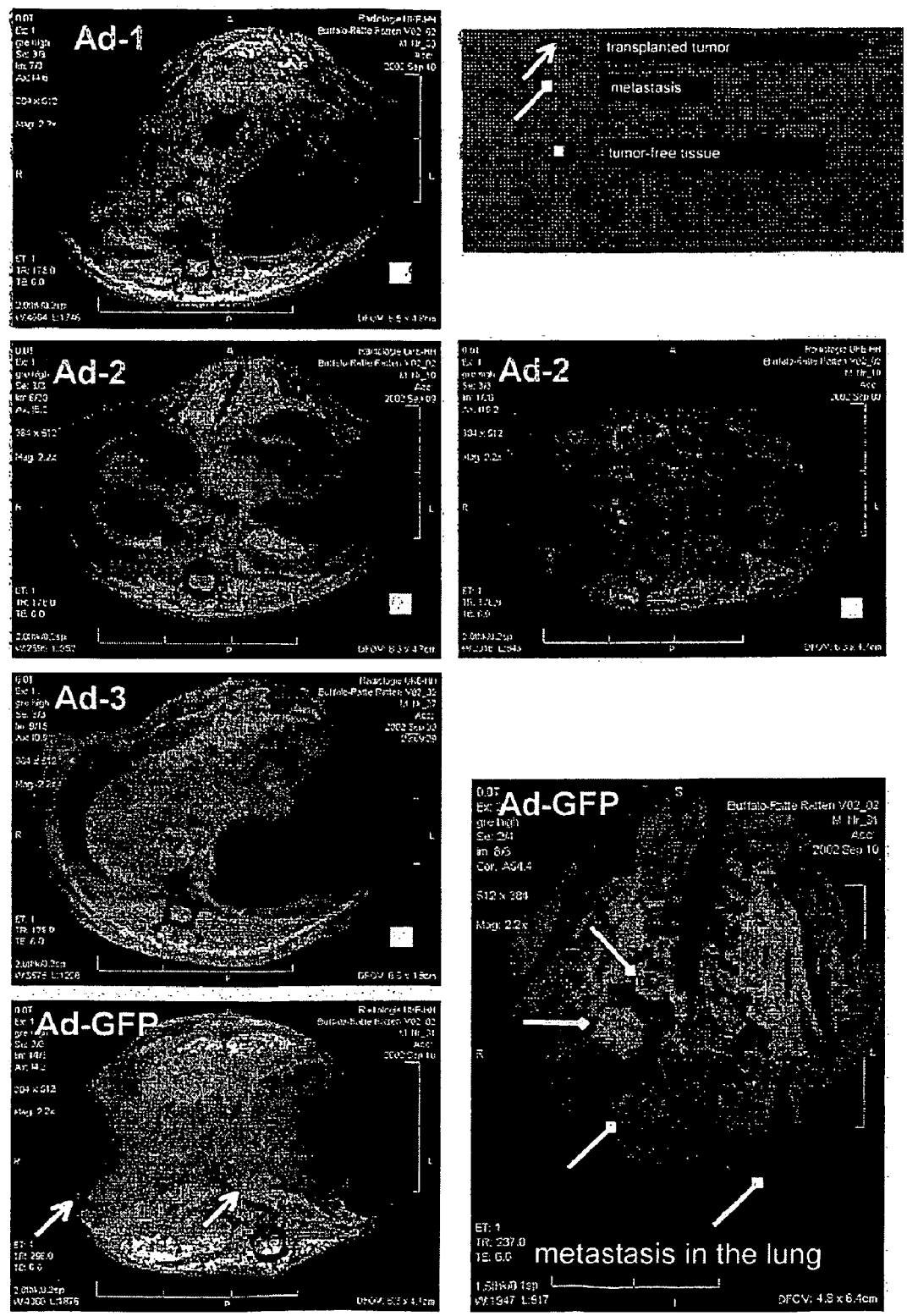

FIG. 10 MRT images of the tumors after the virus injection, week 7.

Figure 11:
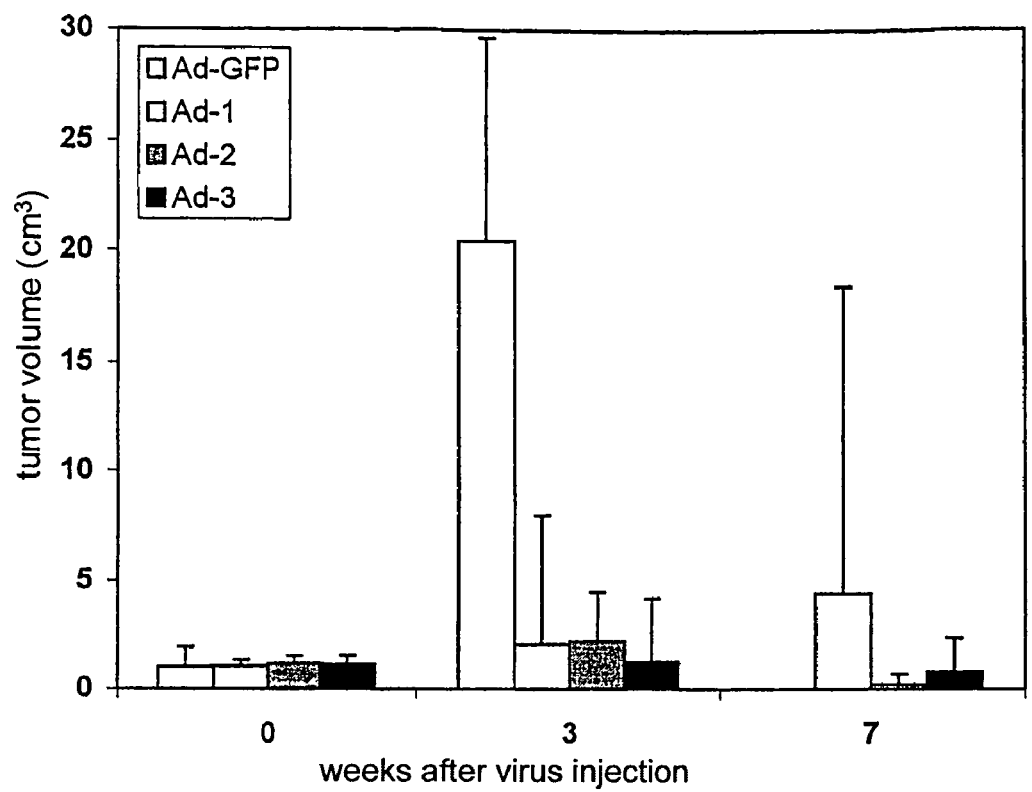

FIG. 11 Course of the changes of the tumor sizes, calculated from the MRT data.

Procedure: The total volumes were monitored by MRT: sizes were determined one day before as well as 3 and 7 weeks after virus administration. Control group Ad-GFP: 9 animals; immune treated group: 10 animals each in the groups Ad-1, Ad-2 and Ad-3. In group Ad-1 only one rat displayed continuous tumor growth. All animals in the control group died within 7 weeks.

Figure 12:
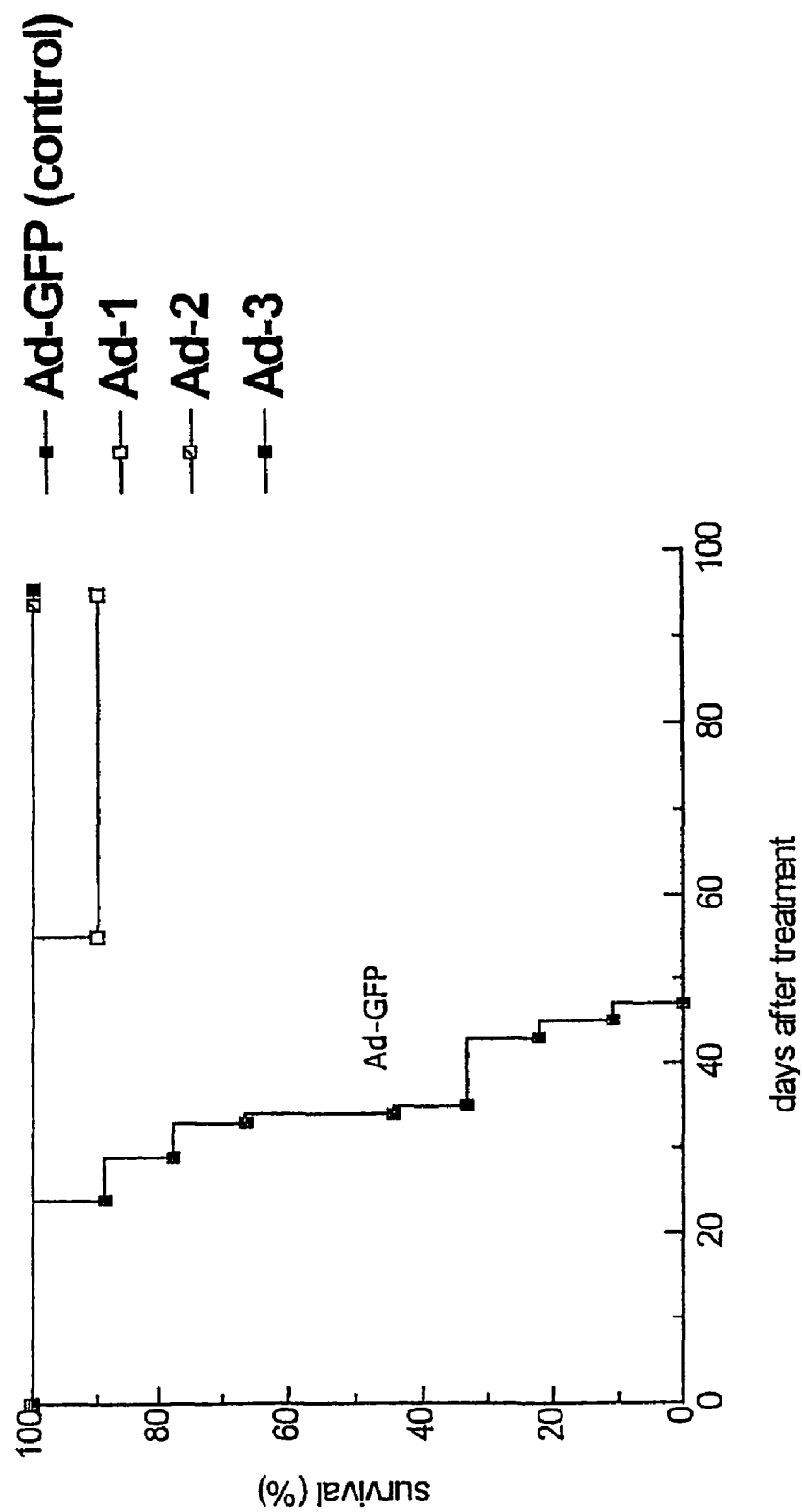

FIG. 12 Long-term survival rate of the experimental animals up to 100 days after virus injection.

Figure 13:
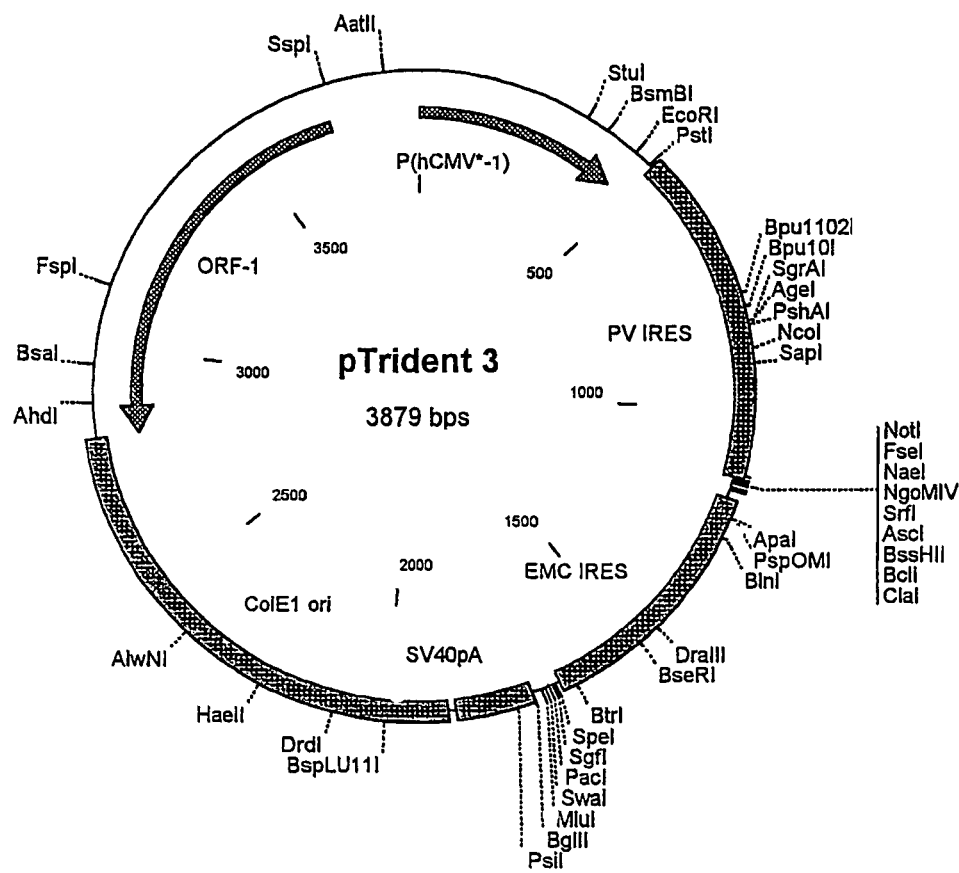

FIG. 13 Map of the vector pTrident3.

Figure 14:
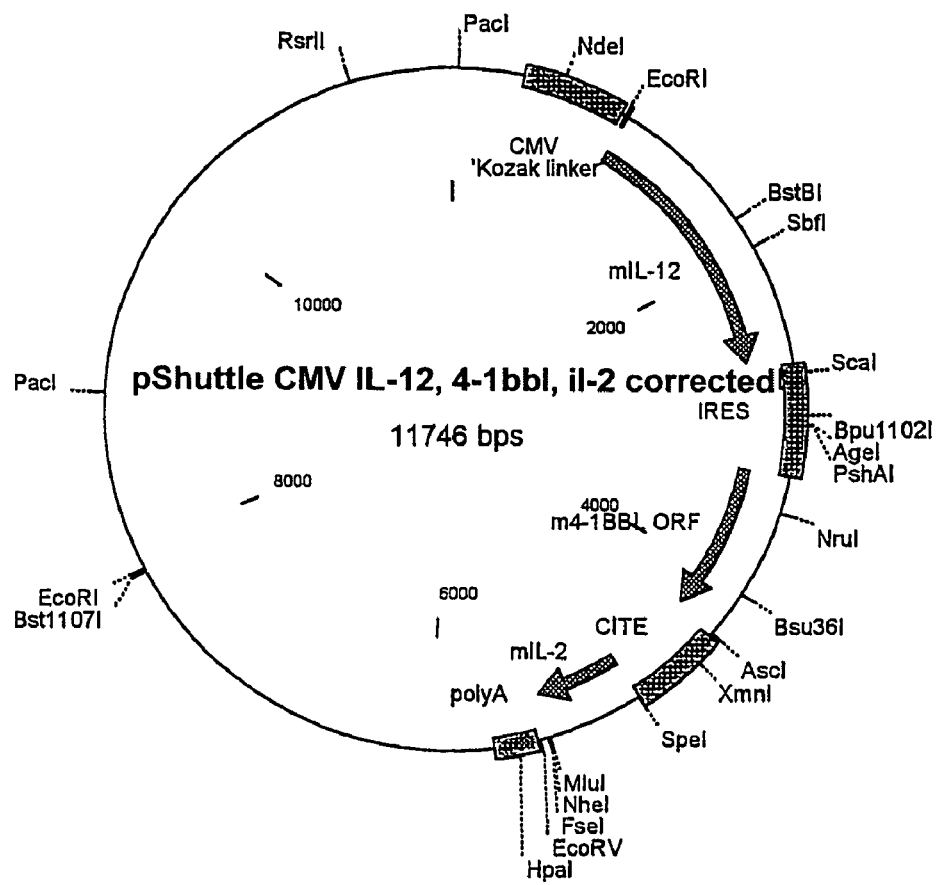

FIG. 14 Map of the vector pShuttle [CMV]IL12[IRES]4-1BBL[IRES] IL2.

Figure 15:
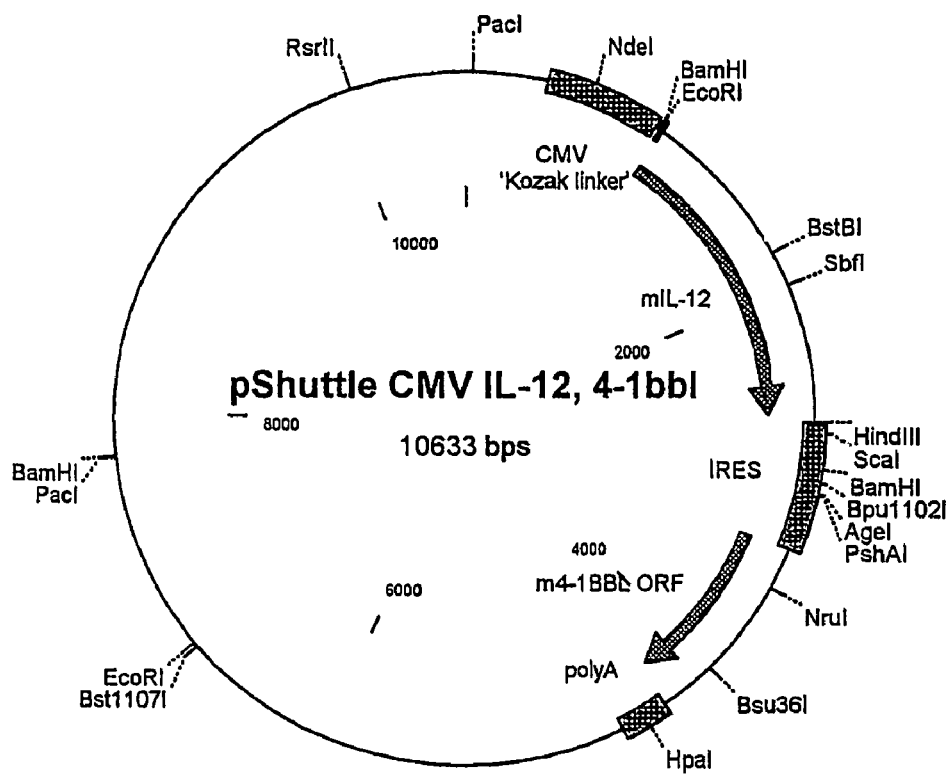

FIG. 15 Map of the vector pShuttle [CMV]IL12[IRES]4-1BBL.

Figure 16:
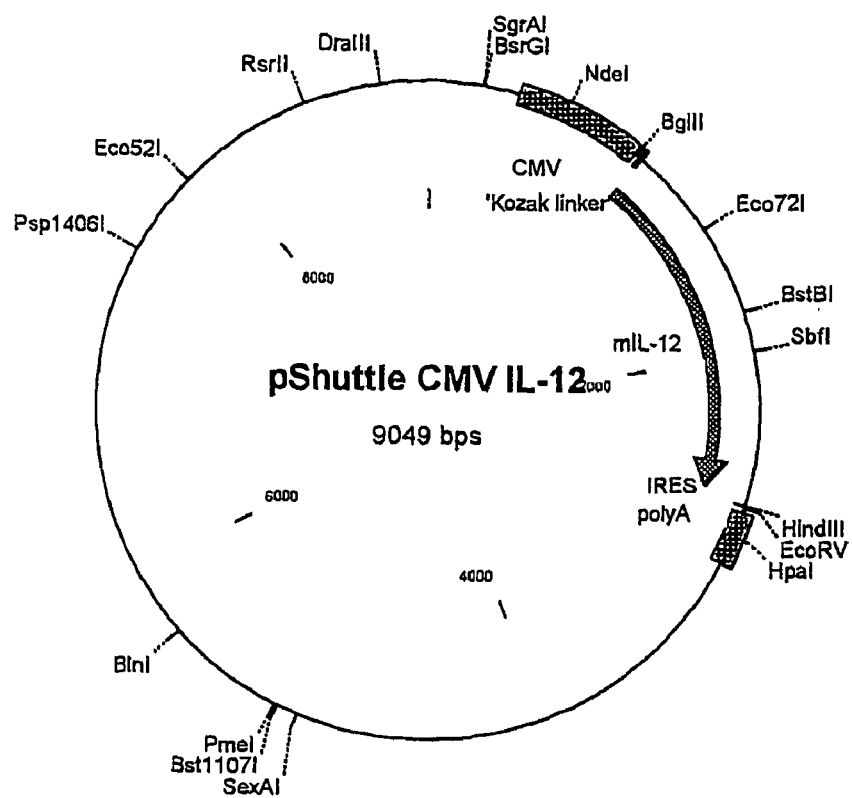

FIG. 16 Map of the vector pShuttle [CMV]IL12.

Figure 17:
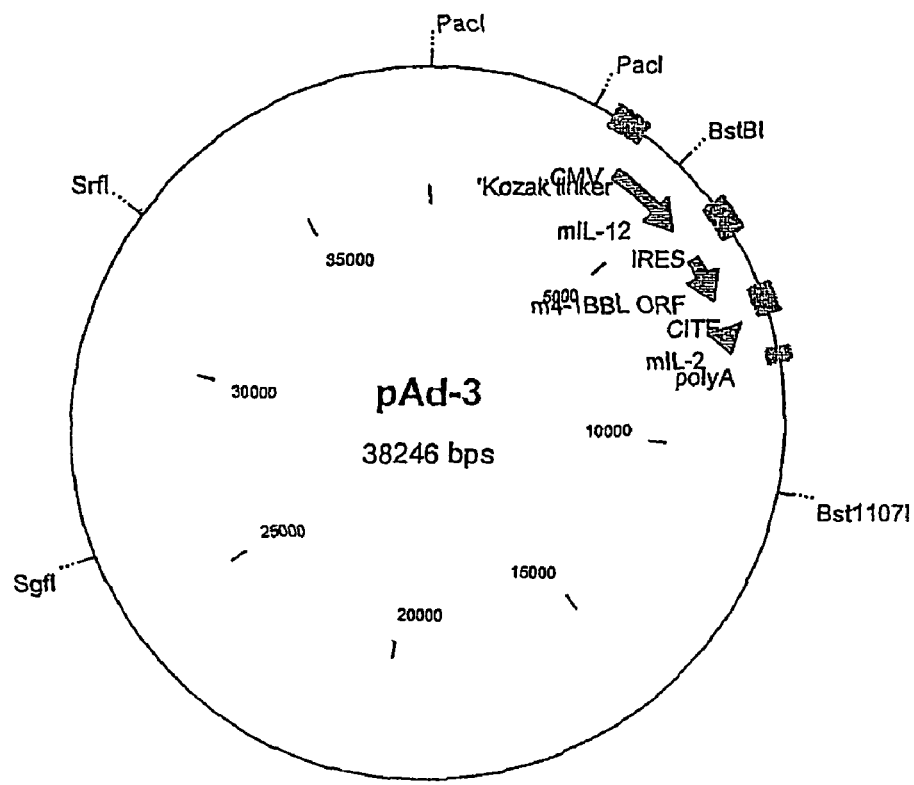

FIG. 17 Map of the vector pAd-3.

Figure 1:
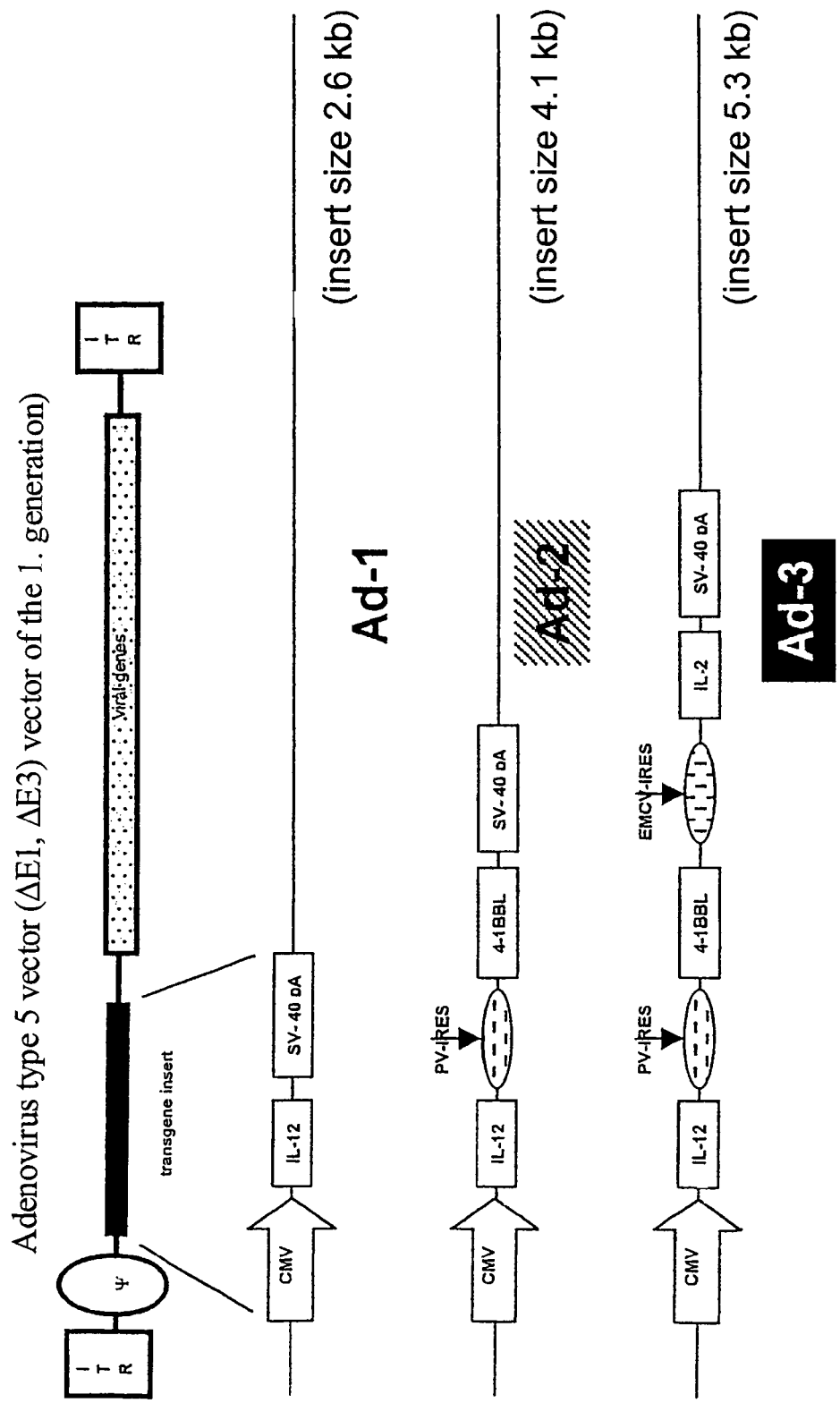
FIG. 1 Schematic overview of vectors Ad-1 to Ad-3.

FIG. 18 Sequence of the tri-cistronic expression cassette containing the murine cDNA; corresponds to insert Ad-3 in FIG. 1 (SEQ ID NO: 1).

FIG. 19 Coding sequence of the human IL-12 40 kDa (SEQ ID NO: 2).

FIG. 20 Coding sequence of the human IL-12 35 kDa (SEQ ID NO. 3).

FIG. 21 Coding sequence of the human 4-1BBL (SEQ ID NO: 4).

FIG. 22 Coding sequence of the human IL-2 (SEQ ID NO: 5).

FIGS. 23A and B Coding sequence of the human B7-1 (SEQ ID NO: 6) and B7-2 (SEQ ID NO: 7).

FIG. 24 Sequence of shuttle vector for Ad-3 (SEQ ID NO: 8).

FIG. 25 Sequence of shuttle vector for Ad-2 (SEQ ID NO: 9).

FIG. 26 Sequence of shuttle vector for Ad-1 (SEQ ID NO: 10).

FIG. 27 Sequence of plasmid containing the whole DNA coding for Ad-3 (SEQ ID NO: 11).

Figure 28:
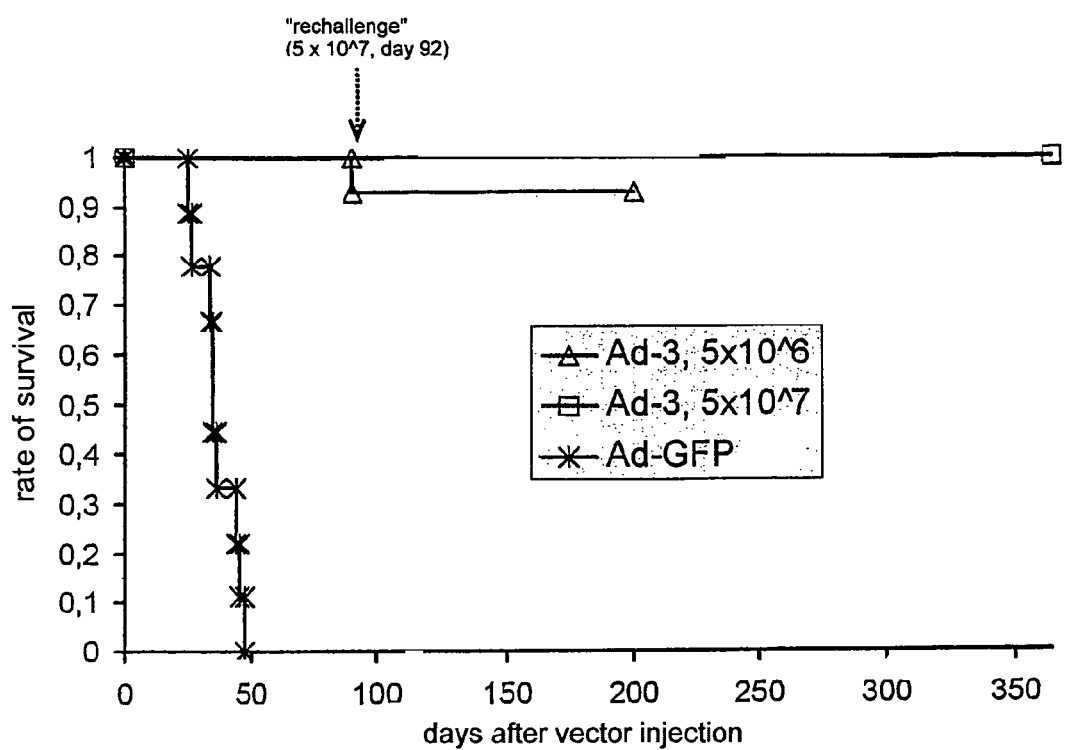

FIG. 28 Illustration of the efficacy within a monitoring period of up to one year. The graph shows the fraction of living rats for each time point (survival rate 1=100% of the animals in one group). Therapy groups: Ad-3, $5 \times 10^6$ (n=12), Ad-3, $5 \times 10^7$ (n=10). Control group: $5 \times 10^8$ Ad-GFP (n=9).

In this long-term study two liver tumors were planted in each animal. 2 weeks later (at day 0 in the Figure) one of the tumors received a single vector injection. At this time point the tumor volume was approximately 1 ml. The figure shows that the control animals (treated with Ad-GFP) died within 47 days after vector injection. In the group treated with $5\times10^6$ i.u. ("infectious units" or infectious particles) of Ad-3 one animal died after 90 days, and in the group treated with $5\times10^7$ i.u. of Ad-3 all animals survived.

Rechallenge: In the group treated with $5\times10^7$ i.u. of Ad-3, tumors were again implanted into the liver of all animals at 92 days (13 weeks) after vector injection. The tumor cell implant disappeared in all 10 animals without further treatment.

Figure 29:
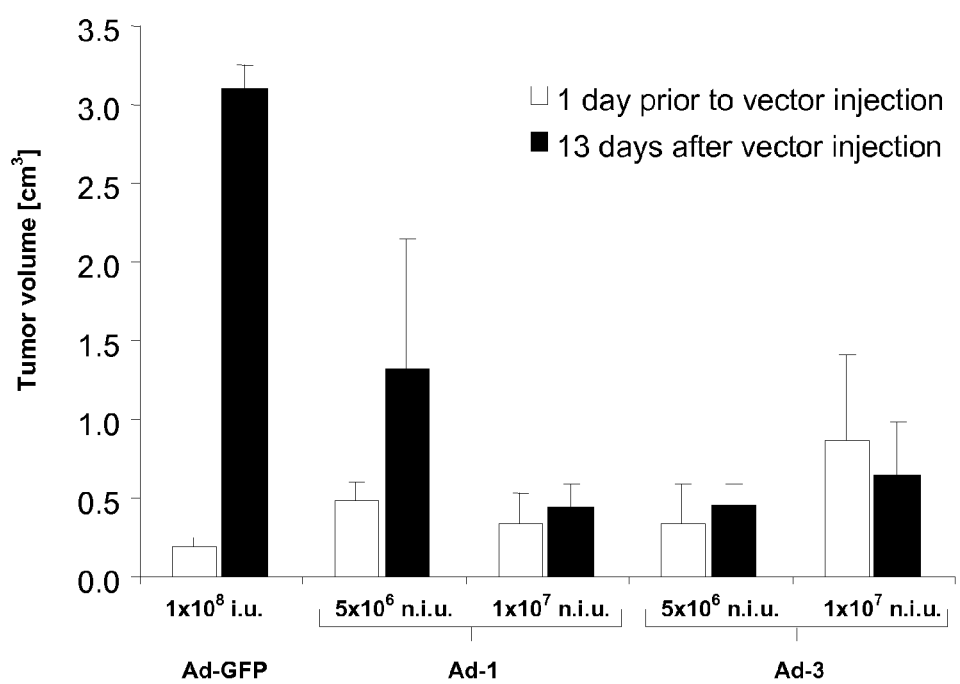

FIG. 29 Illustration of the effects on tumor growth after treatment with Ad-1 and Ad-3 in comparison with a control vector (Ad-GFP).

Here, two different dosage levels of Ad-1 and Ad-3 were administered and tumor sizes were determined 2 weeks post-treatment. Animal number per group: n=3. The figure shows the change of tumor volumes at different vector doses of Ad-1 and Ad-3. $1\times10^6$ McA-RH7777 tumor cells were injected into the right liver lobe and 2 weeks later the vector was injected into the left tumor. MRT scans were performed one day before and 13 days after vector administration. With $5\times10^6$ i.u. of Ad-1 the mean tumor volume increases significantly, whereas it increases only minimally with $1\times10^7$ i.u. of Ad-1. For Ad-3 this only minimal increase is already observed at a dosage of $5\times10^6$ i.u., whereas at $1\times10^7$ i.u. a decrease becomes already obvious. Therefore, Ad-3 proves to be clearly more effective than Ad-1. The values for $1\times10^7$ i.u. of Ad-3 were determined at day 3 and day 12 after vector injection. The controls (Ad-GFP) massively increase within the monitoring period of 2 weeks. Extrahepatic metastases were not included into the calculations in those animals, where they develop.

DETAILED DESCRIPTION OF THE INVENTION

Surprisingly, the process according to the invention revealed that vectors coding for single chain IL-12 and a costimulator protein are notably suitable for the treatment of tumors in the context of an immunotherapy. By means of immunotherapy not only the primary tumor but also the metastases are eliminated.

The synergistic effect of the constructs according to the invention encoding proteins involved in the stimulation of the immune system allows the use of these nucleic acids in lower doses than suggested in the prior art. This lower dosage results in less side effects, as for example in a reduced risk for the patient to develop auto-immune diseases, combined with improved security during clinical use. The probability of propagating the virus is lower than that using known viruses. The low dosage further enables the treatment of larger tumor masses or the simultaneous treatment of several tumors without generating side effects.

Compared to the use of genes coding for both subunits, the use of the single chain IL-12 gene saves space in the vector for the expression of the nucleic acids. Thus, this sequence allows the use of relatively small vectors, for example adenoviral vectors, which nevertheless do not only contain the gene for single chain IL-12, but also two or more additional foreign genes, which intensify the immunotherapy.

The vectors according to the invention are determined for the treatment of mammals, in particular for the treatment of humans. Therefore, the following references to certain gene sequences preferably refer to human sequences. However, the gene sequences can also be derived from other species or can be modified within the limits of the specified homologous areas using known technologies (which, in the context of the present application, have been determined using BLAST software) as long as the specific protein activity (immune stimulating and/or T-cell binding) remains in the area of at least 50%, preferably of at least 70% of the corresponding activity of the human gene product. The quoted areas of homology refer to the area, which in the native gene codes for the biological activity. Provided that nucleic acids are used, which code for fusion proteins, the area of homology refers to the fragment coding for the designated biological activity (IL-12, costimulator). Modifications of the gene sequence are included which result in an enhancement of the activity of the proteins.

In the present invention the term "sequences coding for a costimulator protein" is used to refer to sequences which, upon expression in human cells, produce proteins that are present as cell surface proteins and which are specifically bound by T-cell receptors. Upon binding to a T-cell the costimulator proteins enhance the immune reaction. Corresponding costimulator proteins are known in the art, for example 4-1BB ligand (4-1BBL), B7-1 (also known as CD80) and B7-2.

In an especially preferred embodiment of the invention the vector comprises sequences, which code for the costimulator protein 4-1BB ligand, particularly for sequences having a sequence homology of at least 40%, preferably of at least 70%, of at least 80% or of at least 90% to the sequence shown in FIG. 21, wherein the protein encoded by this sequence has the ability to bind T-cells specifically. Further activity tests 4-1BBL are known in the art (Vinay D S, Kwon B S. Semin. Immunol., 1998, 10: 481-9. Review; Kwon et al., Mol Cells., 2000, 10: 119-26).

In the present invention a protein is referred to as single chain IL-12 if the protein consists of an amino acid sequence comprising both subunits of the native IL-12 as a fusion protein. Nucleic acid sequences coding for single chain IL-12 will usually have a sequence homology of at least 40%, preferably of at least 70%, of at least 80% or of at least 90% in relation to the sequences shown in FIGS. 19 and 20. The sequences shown represent the IL-12 part of the fusion gene. Sequences linking the subunits are known to the skilled person and are not considered during homology analysis. The single chain IL-12 further has an immune stimulating activity, which is not significantly lower than the activity of the native IL-12 in its heterodimeric form. One of the effects of the human IL-12 during the stimulation of the immune system is the initiation of the release of gamma-interferon. The immune stimulating activity of single-chain IL-12 is at least 50%, preferably at least 70% of the corresponding activity of the native IL-12. The activity of the proteins can be compared by means of known in vitro assays (for example, by means of the in vitro tests used to compare the activity of IL-12 as described by Lieschke et al., loc. cit.). In an especially preferred embodiment of the invention, the immune stimulating activity of the single chain IL-12 is even higher or significantly higher than the corresponding activity of the native IL-12.

In another embodiment of the invention, the present invention further comprises vectors, which code for further cytokines, for proteins with cytokine activity and/or for costimulator proteins. Proteins with cytokine activity are proteins which exhibit the immune stimulatory activity of cytokines, but lack any structural relation to cytokines Corresponding cytokine agonists, for example agonistic cytokine receptor antibodies, are known in the prior art.

In addition to the specifically mentioned sequences, which code for single chain IL-12 and a costimulator protein, the vectors according to the invention may also contain sequences encoding one or several other cytokines that activate T- and/or B-cells or encoding one or several other costimulator proteins.

In particular the present invention relates to vectors comprising sequences coding for single chain IL-12, 4-1BB ligand and IL-2. According to the present invention a protein is referred to as IL-2, when it is coded by a sequence having a sequence homology of at least 40%, preferably at least 70%, at least 80% or at least 90% in relation to the sequence presented in FIG. 22. Sequences coding for IL-2 that are used according to the present invention further exhibit essentially the immune stimulatory activity of the native IL-2, i.e., according to the present invention IL-2 coding sequences are used, which exhibit an immune stimulatory activity in vitro corresponding to at least 70% of the activity of the native IL-2. Corresponding in vitro assays for the detection of IL-2 activity are known in the prior art. Preferably, the method described by Gillis et al. (J. Immunol., 1978, 120 (6): 2027-32) is used to determine activity.

In a further embodiment, the vectors according to the invention in addition to single chain IL-12, 4-1BB ligand and IL-2 also comprise sequences coding for the costimulator protein B7-1 and/or B7-2.

In the context of the present invention, a costimulator protein is referred to as B7-1 (or B7-2) if it is coded by a gene with a sequence homology of at least 40%, preferably of at least 70%, of at least 80% or of at least 90% in relation to the sequences presented in FIG. 23 A (or B).

According to an embodiment of the present invention, the vectors further comprise sequences which allow the expression of the coding sequences. The vectors according to the invention may thus contain a promoter and one or more internal ribosome entry sites (IRES). The promoters may exhibit tumor specificity, that means that they are expressed in the tumor only, or they are not active in all cells.

In certain embodiments of the invention, non-specific promoters are preferred, because as a rule such promoters are expressed superiorly and such vectors may be used for the treatment of different tumors.

According to the invention, particularly high expression rates of the immune stimulating genes were obtained using vectors which are at least tri-cistronic and which are further characterized by containing only one promoter per expression cassette, and by containing one IRES sequence for each cistron, which is not located directly after a promoter. It has been shown that the use of several promoters within one expression cassette may lead to cross-inhibitory effects of these promoters. A combination of promoters and IRES sequences resulted in improved expression. The use of different IRES sequences within one vector has the further advantage that the recombination frequency between these sequences may be minimized.

When using tetra-cistronic vectors, it might be advantageous to split the cistrons into several expression cassettes (see examples). In this case, preferably one promoter is present per expression cassette. Due to the split into two expression cassettes that preferably have maximum distance within the vector, the promoters are spatially separated and cross-inhibition is thus reduced.

The sequences according to the invention exhibit the special advantage that the proteins are particularly well expressed in human cells. In this embodiment the advantageous effect of the sequences according to the invention for immunotherapy is thus also based on the high expression of the coding sequences.

In the context of the present invention, the vectors preferably consist of DNA or RNA.

In the context of the present invention, a vector is referred to as "viral vector" if it consists of a nucleic acid sequence that comprises sequences of viral origin which permit packaging of the nucleic acid in viral envelopes.

Dependent on the viral origin of the sequences, the vectors may be present as adenoviral vectors, adeno-associated vectors, lentiviral vectors, HSV vectors, retroviral vectors, baculoviral vectors or Semliki-Forrest-Virus vectors. The adenoviral vectors may be adenoviral vectors of the first (deletions in the regions E1 and E3 of the AdEasy cloning system; e.g., available from QBiogene GmbH, Heidelberg, Germany) or second generation (deletions in E1, E2, E3, E4, etc.) or helper-dependent adenoviral vectors. Corresponding vectors are extensively known in the art (Nicklin S A, Baker A H, Curr Gene Ther., 2002, 2: 273-93; Mah et al., Clin Pharmacokinet., 2002, 41: 901-11).

An especially preferred embodiment of the present invention relates to the invention of an adenoviral vector comprising sequences that encode the single chain IL-12, 4-1BB ligand and IL-2. Adenoviral vectors have the special advantage that corresponding vectors exist which are approved for use in human gene therapy. Therefore, the vectors are safe for certain applications (for example, tumor treatment with local administration). Adenoviral vectors belong to vector systems that are used most frequently in a hospital, and for which most of the data concerning safety of their use are available.

However, only a limited amount of foreign nucleic acid sequences can be incorporated in adenoviral vectors. Until now it was therefore not possible to incorporate more than two genes that encode immune stimulatory proteins into a corresponding vector. This problem is solved for the first time by the subsequent detailed description of the vector development and thus adenoviral vectors are enabled which encode more immune stimulatory proteins as compared with known vectors. Particularly advantageous adenoviral vectors for 3 genes (3-gene-vectors) are thus provided by means of the present invention, that may also be referred to as tri-cistronic vectors. Further, for the first time, adenoviral vectors are provided that express 4 genes, wherein in the presented examples they were split up into two expression cassettes.

The present invention further relates to virus particles that comprise the vectors according to the invention. The term virus particles or virions refers to nucleic acids that are enclosed by the coat proteins of a virus.

According to a further embodiment, the present invention relates to medicaments comprising the vectors or virus particles according to the invention. The vectors or virus particles according to the invention may be mixed with a carrier compound or they can be administered together with further adjuvants. The vectors or virus particles according to the invention may be, for example, incorporated into liposomes or into liposomes with replication-competent adenoviruses (RCAs; see Yoon et al., Curr Cancer Drug Targets, 2001, 1: 85-107), or may be present as polyethylene glycol enclosed adenoviruses, as antibody-linked adenoviruses (i.e., as viruses linked with an antibody that has specificity for the virus and for a cellular marker, preferably a tumor cell marker), admixed with RCAs, as a cassette within an RCA or as an RCA conditioned for replication within the tumor (conditional RCA: RCA with an E1 function under the regulation of a tumor specific promoter; van der Poel et al., J Urol., 2002, 168: 266-72).

The exact dosage of the virus particles depends on the disease to be treated, on the type of administration and on the structure of the used vector, and may be determined by the expert in an individual case using standard procedures. The nucleic acids according to the invention enable a destruction or a significant reduction of the tumor already at an especially low dosage. The medicament preferably has a concentration per unit dose of not more that $1 \times 10^{11}$, preferably of not more than $1 \times 10^{10}$, not more than $1 \times 10^{9}$ or not more than $1 \times 10^{7}$. However, the dosage may be significantly lower than the mentioned ranges and may even be as low as $1 \times 10^{6}$. The dosage numbers given here refer to the number of infectious virus particles. It has been shown in a rat tumor model that all animals survived tumor injection over a period of more than one year when treated with a dosage of $5 \times 10^{7}$ infectious virus particles. Still approximately 90% of the animals survived a treatment with a dosage of $5 \times 10^{6}$ infectious virus particles. However, all animals in the control group died within the first 50 days after the tumor injection. These dosages are several orders of magnitude below the doses suggested in the prior art for corresponding treatments.

The medicament is formulated such that the vectors are transferred sufficiently to the tumor. Preferably, the medicament is used as a solution for the intra-tumoral injection. The production of corresponding solutions is well known in the art. As an alternative, the medicament can be formulated as a carrier compound that releases the vector over a certain time period after implantation into the tumor. Corresponding carrier compounds, e.g., cellulose sulfate or the like, are well known in the art.

Finally, the present invention relates to the use of the vectors or the virus particles for the treatment of tumors, especially for the treatment of solid tumors, like HCC, colon cancer, breast cancer, etc., in humans.

According to an alternative embodiment, the present invention relates to the use of the vectors or virus particles for the treatment of infectious diseases or prionic diseases. An immune stimulating therapy, also in the form of a gene therapy, was already suggested for the treatment of corresponding infectious diseases (see van der Meide et al., Vaccine., 2002, 20: 2296-302).

The immune stimulating effect of the vectors and virus particles according to the invention thus has further therapeutic potential for the treatment of infectious diseases, such as for the treatment of infections caused by the human immunodeficiency virus (HIV), by hepatitis virus types A, B, C (HAV, HBV, HCV), by Cytomegalovirus (CMV), and by human papilloma viruses (HPV), which among others, can cause cervical carcinoma. The viruses or virus particles may also be used advantageously for the therapy of prionic diseases, since unspecific immune stimulation has already resulted in a successful cure in an animal model (Sethi et al., Lancet, 2002, 360: 229-30).

For the medical use according to the invention, the vector is present in a concentration of not more than $1 \times 10^{11}$, preferably of not more than $1 \times 10^{10}$, not more than $1 \times 10^{9}$ or not more than $1 \times 10^{7}$. However, the dosage may be considerably below the mentioned ranges and may be lower than $1 \times 10^{6}$. Again, the dosage numbers given here refer to the number of infectious virus particles.

The following examples illustrate the invention. Detailed information on the production and the use of the vectors mentioned in the examples are further presented in the doctoral thesis (dissertation) of Reinhard Waehler having the title "Adenovirale Immuntherapie solider Tumore am HCC-modell der Ratte (*Rattus norvegicus*, Berkenhout 1769)" of the "Fachbereich Biologie", Hamburg University.

Examples

I. Construction of the Vectors Ad-1, Ad-2, Ad-3 and their Testing In Vitro and In Vivo 1. Production of the Vectors At first, the murine cDNAs of scIL-12, 4-1BBL and IL-2 were cloned into the plasmid pTrident3 (FIG. 1). The result was termed pT3 scIL-12[IRES]4-1BBL[IRES]IL-2 (not shown). Beforehand, the 5'-regions of the reading frames of the three components and their distances to the IRES elements were modified.

Figure 2:
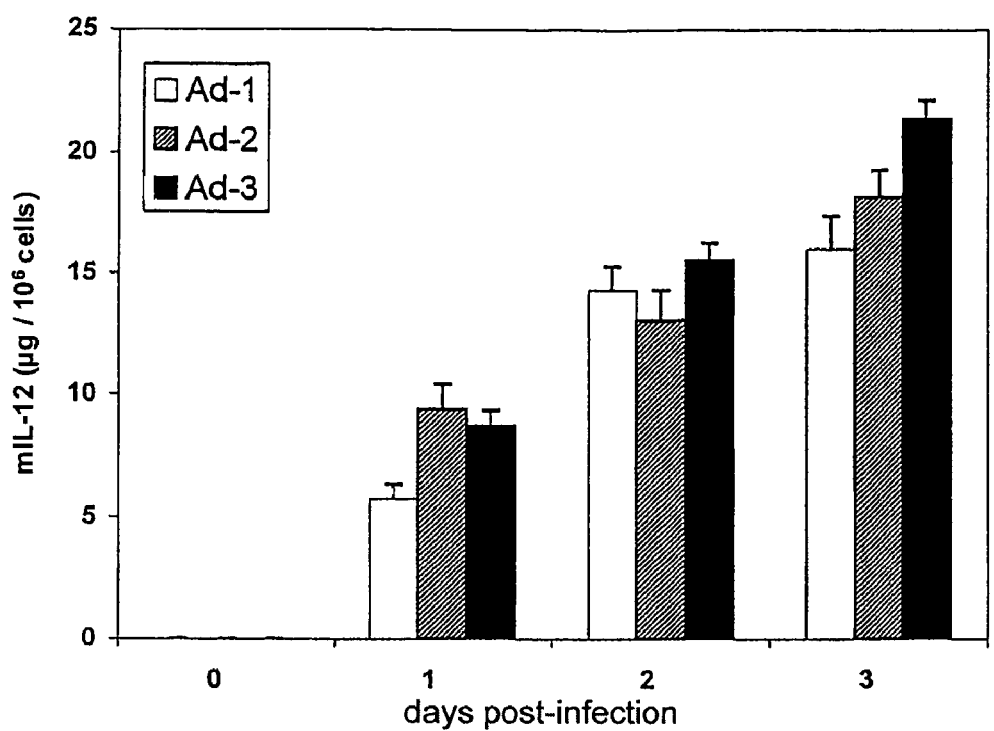
FIG. 2 Determination of the amount of interleukin in the cell culture supernatant of McA-RH7777 cells after transfection with Ad-1, Ad-2 and Ad-3. Vector amounts that should be used for the animal experiments were adjusted with reference to identical IL-12 expression.

The thus constructed tri-cistronic expression cassette was cloned without promoter and without the 3'-non-translated sequences into the pShuttle-CMV plasmid of the AdEasy system (QBiogene GmbH, Heidelberg). The result is the plasmid pShuttle [CMV]scIL12[IRES]4-1BBL[IRES]IL2 (FIG. 2). The correctness of the cassette [CMV]scIL12[IRES]4-1BBL[IRES]IL2 of the last mentioned plasmid was completely verified by DNA sequencing.

Then, after co-transformation with the plasmid pAdEasy1 into the *E. coli* strain Bj5183, this construct was recombined to the plasmid pAd-3 (see FIG. 1) that contains the complete recombinant DNA for Ad-3.

Starting from pShuttle-[CMV]scIL12[IRES]4-1BBL [IRES]IL2, the plasmids for Ad-2, pShuttle-[CMV]scIL12 [IRES]4-1BBL[IRES]1BBL (see Fig.) and for Ad-1, pShuttle-[CMV]scIL12 (see FIG. 1) were cloned, and in an analogous manner the plasmids pAd-2 and pAd-1 were generated for the production of pAd-3.

After their release from the plasmid precursors by PacI-digestion the adenoviruses were transfected into HEK293 cells and the resulting viral plaques were isolated propagated (i.e., as virus particles).

Overview of the express cassettes: FIG. 1.

2. Expression Tests 2.1 IL-12

Rat hepatoma cells, McA-RH7777, were infected with the viruses (virus particles) Ad-1, Ad-2 and Ad-3, and the IL-12 expression was quantified in the cell culture supernatant after different time points using IL-12 p70-ELISA.

Overview: FIG. 2.

2.2 4-1BBL

Rat hepatoma cells, McA-RH7777, were infected with the viruses (virus particles) Ad-1, Ad-2 and Ad-3, and the 4-1BBL expression was determined after different time points by flow-through cytometry after staining of the 4-1BBL with the antibody TKS-1 (BD Pharmingen, Heidelberg). Ad-1 was used as negative control, since no 4-1BBL expression can be expected.

Overview: FIG. 3.

2.3 IL-2

Rat hepatoma cells, McA-RH7777, were infected with the viruses (virus particles) Ad-1, Ad-2 and Ad-3, and the IL-2 expression was quantified in the cell culture supernatant after different time points using IL-2 ELISA. Ad-1 and Ad-2 were used as negative controls, because no IL-2 expression can be expected (not shown).

Overview: FIG. 4.

3. Testing In Vivo 3.1 Dose Escalation 1

The vector Ad-3 (FIG. 5*a*) was tested in our rat model for hepatocellular carcinoma (HCC). The cell line McA-RH7777 (hepatocellular carcinoma of the rat), which is syngenic to the "Buffalo rat", is used for subcapsular hepatic transplantation of tumors.

The tumor growth after implantation of 1 million cells is monitored by magnetic resonance tomography (MRT) in cooperation with Prof. Dr. Gerrit Krupski-Bardien from the radiological clinic of the UKE before and after injection of the virus particles. The development of tumor volumes between day 3 and day 12 after virus injection is shown in FIG. 5b. The very clear effect of the vector within this short time period is dose-dependent and the highest dose yields a reduction of tumor volumes to 27% of the size at the time of virus injection. This result is documented in FIG. 6 with selected MRT images of individual animals to illustrate the tumor size adequately in relation to the animal size.

Based on these data, the dosage for the long-term treatment of larger animal groups was determined at $5 \times 10^7$ infectious particles per tumor. In subsequent studies the effect of the individual vectors (Ad-1 to Ad-3) was now determined at this low dose. As shown in the scheme of FIG. 7, tumors were implanted, then after 14 days 6 animals of the A-groups were treated with the vector and the parameters of the anti-tumor immune response were analyzed after a further 2 weeks. Ten animals each constitute the B-groups (long-term group). Different to the dose escalation study (FIGS. 5 and 6) now two tumors were planted, only one of which was treated with the virus in order to determine the distal effects of the immune stimulation. The B-groups were used to analyze the long-term kinetics of the tumor reduction and the survival rate. According to this scheme the surviving animals received a further intrahepatic tumor implantation after three months to test the immune memory in relation to recognition and combat of tumor recurrence. The survival rate is again determined for another three months.

Our data also show containment of tumor growth within the first 14-day period for the chosen dose of $5 \times 10^7$. The B-groups were already monitored for 100 days. The results of the tumor reduction by our treatment are illustrated in the form of MRT images in FIGS. 8 to 10.

The figures show that with the chosen dose within 7 weeks after virus administration a complete removal was achieved for the injected hepatic tumors but also for the non-injected tumors. The further effect of a complete removal (see Ad-2 series in FIGS. 8 to 10) also of metastases in the liver and in the peritoneum (Ad-2, week 3) is impressive.

The development of the tumor volumes determined from the MRT data is shown and discussed in FIG. 11.

The course of the study expressed as survival rate in % within the treated groups is illustrated in FIG. 12. In the course of the animal experiments IL-12 was detected in the serum of the rats. Additionally, interferon-gamma was determined which is released from immune cells and which is responsible for the majority of anti-tumor effects. Interferon-gamma was also clearly detectable. In addition to these determinations, T-cells which are specifically directed against the tumor were detected in a so-called cytotoxicity test. The immune cell response was actually also characterized with tissue preparations of the treated animals. In treated tumor tissue CD8+ cells, CD4+ cells, macrophages and natural killer cells were detected in increased amounts as compared to tissue treated with control vector.

3.2 Protocol for Performing the Long-Term Study

Two tumors were planted by injection of McA-RH7777 cells. The cells were injected into two different liver lobes. For one of the tumors 1 million cells were used. In this left-side tumor the virus injection was performed later. A further right-side tumor was planted with 650,000 cells. This tumor served as an intrahepatic metastasis model. At this tumor the efficacy of the stimulated immune cells in a distal tumor was checked. The results are shown in FIGS. 9 to 12 and 28 to 30.

II. Construction of Ad-4

Using an insertion system different from homologous recombination in *E. coli* cells, an expression cassette for the B7-1 is inserted at the position of the adenoviral E3 region. This region is functionally inactive, because large segments of this region were deleted in the vectors used here. The expression cassette includes its own promoter of the human phosphoglycerate kinase or a promoter with similar strength.

The production of the viruses was performed in an equivalent manner as described in the preceding protocol.

The invention claimed is:

1. An adenoviral vector comprising
a first nucleic acid sequence having a sequence homology of at least 80% to the full length sequence set forth in SEQ ID NO: 2;
a second nucleic acid sequence having a sequence homology of at least 80% to the full length sequence set forth in SEQ ID NO: 3,
a third nucleic acid sequence having a sequence homology of at least 80% to the full length sequence selected from the group consisting of SEQ ID NOs: 4, 6, and 7; and
a fourth nucleic acid sequence having a sequence homology of at least 80% to the full length sequence set forth in SEQ ID NO: 5;
wherein said first nucleic acid sequence and said second nucleic acid sequence are linked together and when expressed produce a single fusion protein.

2. The adenoviral vector according to claim 1, further comprising one or several promoters and one or several internal ribosome entry sites (IRES).

3. The adenoviral vector according to claim 1, wherein said adenoviral vector is an adenoviral vector of the first or second generation or a helper-dependent adenoviral vector.

4. The adenoviral vector according to claim 1, wherein said one or several promoters is a non-tumor-specific promoter that mediates the expression of said first and said second nucleic acid sequences and said one or several IRES sequences precedes said third nucleic acid sequence and said fourth nucleic acid sequence.

5. A virus particle comprising the adenoviral vector according to claim 1.

6. A medicament comprising virus particles according to claim 5.

7. A medicament comprising the adenoviral vector according to claim 1.

8. A medicament according to claim 7, wherein said medicament is formulated as a solution for intra-tumoral injection or as a carrier compound that releases the adenoviral vector over a certain time period after implantation into the tumor.

9. The adenoviral vector according to claim 1, wherein said third nucleic acid sequence comprises a nucleic acid sequence having a sequence homology of at least 80% to the full length sequence of SEQ ID NO: 4.

10. An adenoviral vector comprising
a first nucleic acid sequence having a sequence homology of at least 80% to the full length sequence set forth in SEQ ID NO: 2;
a second nucleic acid sequence having a sequence homology of at least 80% to the full length sequence set forth in SEQ ID NO: 3, and
a third nucleic acid sequence having a sequence homology of at least 80% to the full length sequence selected from the group consisting of SEQ ID NOs: 4, 6, and 7;
wherein said first nucleic acid sequence and said second nucleic acid sequence are linked together and when expressed produce a single fusion protein.

11. The adenoviral vector according to claim 10, further comprising one or several promoters and one or several internal ribosome entry sites (IRES).

12. The adenoviral vector according to claim 10, wherein said adenoviral vector is an adenoviral vector of the first or second generation or a helper-dependent adenoviral vector.

13. The adenoviral vector according to claim 11, wherein said one or several promoters is a non-tumor-specific promoter that mediates the expression of said first and said second nucleic acid sequences and said one or several IRES sequences precedes said third nucleic acid sequence.

14. The adenoviral vector according to claim 10, wherein said third nucleic acid sequence comprises a nucleic sequence having a sequence homology of at least 80% to the full length sequence of SEQ ID NO: 4.

15. A virus particle comprising the adenoviral vector according to claim 10.

16. A medicament comprising the adenoviral vector according to claim 10.

17. A medicament comprising virus particles according to claim 15.

18. A medicament according to claim 16, wherein said medicament is formulated as a solution for intra-tumoral injection or as a carrier compound that releases the adenoviral vector over a certain time period after implantation into the tumor.

* * * * *